US010323078B2

(12) United States Patent
Dupin et al.

(10) Patent No.: US 10,323,078 B2
(45) Date of Patent: Jun. 18, 2019

(54) ISOLATED PEPTIDES AND FRAGMENTS THEREOF FROM FIBRINOGEN FOR USE AS DRUGS, PARTICULARLY IN SKIN INFLAMMATORY DISEASES

(71) Applicants: Universite Paris Descartes, Paris (FR); Assistance Publique—Hopitaux de Paris, Paris (FR); Universite Paris—SUD, Orsay (FR); Unviversite Pierre et Marie Curie (Paris 6), Paris (FR); Institut National de la Sante et de la Recherche Medicale (INSERM), Paris (FR); Centre National de la Recherche Scientifique (CNRS), Paris (FR); Institut Gustave-Roussy, Villejuif (FR)

(72) Inventors: Nicolas Dupin, Colombes (FR); Philippe Grange, Chennevieres (FR); Vincent Calvez, Paris (FR); Joël Raingeaud, Palaiseau (FR)

(73) Assignees: Universite Paris Descartes, Paris (FR); Assistance Publique—Hopitaux De Paris, Paris (FR); Universite Paris—Sud, Orsay (FR); Universite Pierre et Marie Curie (Paris 6), Paris (FR); Institut National De La Sante et De La Recherche Medicale (INSERM), Paris (FR); Centre National De La Recherche Scientifique (CNRS), Paris (FR); Institut Gustave-Roussy, Villejuif (FR)

( * ) Notice: Subject to any disclaimer, the term of this patent is extended or adjusted under 35 U.S.C. 154(b) by 0 days.

(21) Appl. No.: 15/559,984

(22) PCT Filed: Mar. 21, 2016

(86) PCT No.: PCT/EP2016/056179
§ 371 (c)(1),
(2) Date: Sep. 20, 2017

(87) PCT Pub. No.: WO2016/150926
PCT Pub. Date: Sep. 29, 2016

(65) Prior Publication Data
US 2018/0105574 A1 Apr. 19, 2018

(30) Foreign Application Priority Data
Mar. 20, 2015 (EP) .................................... 15305414

(51) Int. Cl.
C07K 14/75 (2006.01)
A61P 17/10 (2006.01)
A61P 17/06 (2006.01)
A61P 29/00 (2006.01)
A61K 9/00 (2006.01)
C12N 7/00 (2006.01)
A61K 38/00 (2006.01)

(52) U.S. Cl.
CPC ............ C07K 14/75 (2013.01); A61K 9/0014 (2013.01); A61K 9/0019 (2013.01); A61P 17/06 (2018.01); A61P 17/10 (2018.01); A61P 29/00 (2018.01); C12N 7/00 (2013.01); A61K 38/00 (2013.01); C07K 2319/00 (2013.01)

(58) Field of Classification Search
CPC ................................. C07K 14/75; A61P 17/10
See application file for complete search history.

(56) References Cited

U.S. PATENT DOCUMENTS

| 6,783,961 | B1 * | 8/2004 | Edwards | C07K 14/47 435/91.1 |
| 7,745,391 | B2 * | 6/2010 | Mintz | G06F 19/24 514/19.3 |
| 7,807,409 | B2 * | 10/2010 | Kopetzki | A61K 38/162 435/320.1 |
| 8,268,964 | B2 * | 9/2012 | Scholler | A61K 49/1896 424/278.1 |
| 9,632,084 | B2 * | 4/2017 | Trouw | G01N 33/564 |
| 2007/0172471 | A1 * | 7/2007 | Bjorck | A61K 31/00 424/94.63 |
| 2013/0280820 | A1 * | 10/2013 | Beaumont | G01N 33/6881 436/501 |
| 2013/0330335 | A1 * | 12/2013 | Bremel | G06F 19/18 424/134.1 |
| 2014/0206563 | A1 * | 7/2014 | Beaumont | G01N 33/6881 506/9 |

FOREIGN PATENT DOCUMENTS

| EP | 1 033 401 | 9/2000 |
| WO | WO 90/12866 | 11/1990 |
| WO | WO 03/003988 | 1/2003 |
| WO | WO 2010/054195 | 5/2010 |

OTHER PUBLICATIONS

Database Geneseq [Online] Oct. 6, 2000 (Oct. 6, 2000), Human secreted protein, Seq ID No. 4232., retrieved from EBI accession No. GSP:AAG00151 Database accession No. AAG00151.*

(Continued)

Primary Examiner — Amber D Steele
(74) Attorney, Agent, or Firm — Buchanan Ingersoll & Rooney PC

(57) ABSTRACT

A present invention relates to isolated peptides obtained from human fibrinogen for their use as drug, particularly for the prevention and/or the treatment of inflammatory skin diseases, more particularly acne. The present invention also relates to fragments of these polypeptides, nucleic acid molecules encoding them, expression vectors, host cells, a pharmaceutical composition and a combination product containing them, and their use for treating and/or preventing inflammatory skin diseases, particularly acne.

6 Claims, 26 Drawing Sheets
Specification includes a Sequence Listing.

(56) References Cited

OTHER PUBLICATIONS

Brüggemann et al., *The Complete Genome Sequence of Propionibacterium Acnes, a Commensal of Human Skin,* 305 Science 671-673 (Jul. 30, 2004).
Dawson et al., *Acne vulgaris,* 346 BMJ 1-7 (May 8, 2013).
Debeire et al., *Primary structure of two major glycans of bovine fibrinogen,* 151 Eur. J. Biochem. 607-611 (1985).
Graham et al., *Proinflammatory cytokine production by human keratinocytes stimulated with Propionibacterium acnes and P. acnes GroEL,* 150 Br. J. Dermatol. 421-428 (2004).
Grange et al., *Nicotinamide inhibits Propionibacterium acnes-induced IL-8 production in keratinocytes through the NF-κb and MAPK pathways,* 56 J Dermatol. Sci. 106-112 (2009).
Grange et al., *Production of Superoxide Anions by Keratinocytes Initiates P. acnes Induced Inflammation of the Skin,* 5(7) PLoS Pathog 1-14 (Jul. 2009).
Grice et al., *Topographical and Temporal Diversity of the Human Skin Microbiome,* 324 Science 1190-1192 (May 29, 2009).
Gristina et al., *Infections from biomaterials and implants: a race for the surface,* 14 Med. Prog. Technol 205-224 (1988).
Green et al., *Lectin Affinity High-performance Liquid Chromatography. Interactions of N-glycanase-Released Oligosaccharides with Ricinus Communis Agglutinin I and Ricinus Communis Agglutinin II,* 262 J. Biol. Chem 12030-12039 (1987).
Hillier et al., *Generation and annotation of the DNA sequences of human Chromosomes 2 and 4,* 434(7034) Nature 724-731 (Apr. 7, 2005) (abstract only).
Kang et al., *Inflammation and Extracellular Matrix Degradation Mediated by Activated Transcription Factors Nuclear Factor-κB and Activator Protein-1 in Inflammatory Acne Lesions in Vivo,* 166(6) Am. J. Pathol 1691-1699 (Jun. 2005).
Kistowska et al., *IL—1β Drives Inflammatory Responses to Propionibacterium acnes In Vitro and In Vivo,* 134 J. Invest. Dermatol. 677-685 (2014).
L'hôte et al., *O-glycosylation of Fibrinogen from Different Mammalian Species as Revealed by the Binding of Escherichia coli Biotinylated Lectins,* 76 Thromb. Haemost 710-714 (1996).
Nagy et al., *Distinct Strains of Propionibacterium acnes Induce Selective Human β-Defensin-2 and Interleukin-8 Expression in Human Keratinocytes Through Toll-like Receptors,* 124 J. Invest. Dermatol. 931-938 (2005).
Patti et al., *Microbial adhesins recognizing extracellular matrix macromolecules,* 6 Curr. Opin. Cell. Biol. 752-758 (1994).
Peterson, *Determination of Total Protein,* 91 Methods Enzymol. 95-119 (1983).
Qin et al., *Propionibacterium acnes induces IL-1β secretion via the NLRP3 inflammasome in human monocytes,* 134 J. Invest. Dermatol 381-388 (Feb. 2014).
Romero-Steiner et al., *Adherence of Skin Bacteria to Human Epithelial Cells,* 28 J. Clin. Microbiol. 27-31 (Jan. 1990).
Shen et al., *Collagen Binding to Escherichia coli Strain NG7C,* 27 Curr. Microbiol. 311-316 (1993).
Tachibana et al., *Elucidation of binding specificity of Jacalin toward O-glycosylated peptides: quantitative analysis by frontal affinity chromatography,* 16(1) Glycobiology 46-53 (2006).
Townsend et al., *Carbohydrate Structure of Human Fibrinogen. Use of 300-MHz $^1$H-NMR to Characterize Glycosidase-Treated Glycopeptides,* 257(16) J. Biol. Chem 257 9704-9710 (1982).
Trivedi et al., *Gene Array Expression Profiling in Acne Lesions Reveals Marked Upregulation of Genes Involved in Inflammation and Matrix Remodeling,* 126 J. Invest. Dermatol. 1071-1079 (2006).
Vorm et al., *Improved Mass Accuracy in Matrix-Assisted Laser Desorption/Ionization Time-of-Flight Mass Spectrometry of Peptides,* 5 J. Am. Soc. Mass. Spectrom. 955-958 (1994).
Yu et al., *Fibronectin binding by Propionibacterium acnes,* 19 FEMS Immun. Med. Microbiol. 247-253 (1997).

\* cited by examiner

SEQUENCE LISTING

```
<160> NUMBER OF SEQ ID NOS: 47

<210> SEQ ID NO 1
<211> LENGTH: 491
<212> TYPE: PRT
<213> ORGANISM: homo sapiens
<220> FEATURE:
<221> NAME/KEY: misc_feature
<223> OTHER INFORMATION: sub-unit Bbeta of fibrinogen

<400> SEQUENCE: 1

Met Lys Arg Met Val Ser Trp Ser Phe His Lys Leu Lys Thr Met Lys
1               5                   10                  15

His Leu Leu Leu Leu Leu Leu Cys Val Phe Leu Val Lys Ser Gln Gly
            20                  25                  30

Val Asn Asp Asn Glu Glu Gly Phe Phe Ser Ala Arg Gly His Arg Pro
        35                  40                  45

Leu Asp Lys Lys Arg Glu Glu Ala Pro Ser Leu Arg Pro Ala Pro Pro
    50                  55                  60

Pro Ile Ser Gly Gly Gly Tyr Arg Ala Arg Pro Ala Lys Ala Ala Ala
65                  70                  75                  80
```

-continued

Thr Gln Lys Lys Val Glu Arg Lys Ala Pro Asp Ala Gly Gly Cys Leu
            85                  90                  95

His Ala Asp Pro Asp Leu Gly Val Leu Cys Pro Thr Gly Cys Gln Leu
        100                 105                 110

Gln Glu Ala Leu Leu Gln Gln Glu Arg Pro Ile Arg Asn Ser Val Asp
        115                 120                 125

Glu Leu Asn Asn Asn Val Glu Ala Val Ser Gln Thr Ser Ser Ser Ser
        130                 135                 140

Phe Gln Tyr Met Tyr Leu Leu Lys Asp Leu Trp Gln Lys Arg Gln Lys
145                 150                 155                 160

Gln Val Lys Asp Asn Glu Asn Val Val Asn Glu Tyr Ser Ser Glu Leu
            165                 170                 175

Glu Lys His Gln Leu Tyr Ile Asp Glu Thr Val Asn Ser Asn Ile Pro
            180                 185                 190

Thr Asn Leu Arg Val Leu Arg Ser Ile Leu Glu Asn Leu Arg Ser Lys
            195                 200                 205

Ile Gln Lys Leu Glu Ser Asp Val Ser Ala Gln Met Glu Tyr Cys Arg
            210                 215                 220

Thr Pro Cys Thr Val Ser Cys Asn Ile Pro Val Val Ser Gly Lys Glu
225                 230                 235                 240

Cys Glu Glu Ile Ile Arg Lys Gly Gly Glu Thr Ser Glu Met Tyr Leu
                245                 250                 255

Ile Gln Pro Asp Ser Ser Val Lys Pro Tyr Arg Val Tyr Cys Asp Met
                260                 265                 270

Asn Thr Glu Asn Gly Gly Trp Thr Val Ile Gln Asn Arg Gln Asp Gly
            275                 280                 285

Ser Val Asp Phe Gly Arg Lys Trp Asp Pro Tyr Lys Gln Gly Phe Gly
        290                 295                 300

Asn Val Ala Thr Asn Thr Asp Gly Lys Asn Tyr Cys Gly Leu Pro Gly
305                 310                 315                 320

Glu Tyr Trp Leu Gly Asn Asp Lys Ile Ser Gln Leu Thr Arg Met Gly
                325                 330                 335

Pro Thr Glu Leu Leu Ile Glu Met Glu Asp Trp Lys Gly Asp Lys Val
            340                 345                 350

Lys Ala His Tyr Gly Gly Phe Thr Val Gln Asn Glu Ala Asn Lys Tyr
            355                 360                 365

Gln Ile Ser Val Asn Lys Tyr Arg Gly Thr Ala Gly Asn Ala Leu Met
        370                 375                 380

Asp Gly Ala Ser Gln Leu Met Gly Glu Asn Arg Thr Met Thr Ile His
385                 390                 395                 400

Asn Gly Met Phe Phe Ser Thr Tyr Asp Arg Asp Asn Asp Gly Trp Leu
                405                 410                 415

Thr Ser Asp Pro Arg Lys Gln Cys Ser Lys Glu Asp Gly Gly Gly Trp
            420                 425                 430

Trp Tyr Asn Arg Cys His Ala Ala Asn Pro Asn Gly Arg Tyr Tyr Trp
        435                 440                 445

Gly Gly Gln Tyr Thr Trp Asp Met Ala Lys His Gly Thr Asp Asp Gly
    450                 455                 460

Val Val Trp Met Asn Trp Lys Gly Ser Trp Tyr Ser Met Arg Lys Met
465                 470                 475                 480

Ser Met Lys Ile Arg Pro Phe Phe Pro Gln Gln
            485                 490

```
<210> SEQ ID NO 2
<211> LENGTH: 35
<212> TYPE: PRT
<213> ORGANISM: artificial
<220> FEATURE:
<223> OTHER INFORMATION: fragment Fg1.1

<400> SEQUENCE: 2

Met Lys Arg Met Val Ser Trp Ser Phe His Lys Leu Lys Thr Met Lys
1               5                   10                  15

His Leu Leu Leu Leu Leu Leu Cys Val Phe Leu Val Lys Ser Gln Gly
            20                  25                  30

Val Asn Asp
        35

<210> SEQ ID NO 3
<211> LENGTH: 35
<212> TYPE: PRT
<213> ORGANISM: artificial
<220> FEATURE:
<223> OTHER INFORMATION: fragment Fg1.2

<400> SEQUENCE: 3

Asn Glu Glu Gly Phe Phe Ser Ala Arg Gly His Arg Pro Leu Asp Lys
1               5                   10                  15

Lys Arg Glu Glu Ala Pro Ser Leu Arg Pro Ala Pro Pro Pro Ile Ser
            20                  25                  30

Gly Gly Gly
        35

<210> SEQ ID NO 4
<211> LENGTH: 36
<212> TYPE: PRT
<213> ORGANISM: artificial
<220> FEATURE:
<223> OTHER INFORMATION: fragment Fg1.3

<400> SEQUENCE: 4

Tyr Arg Ala Arg Pro Ala Lys Ala Ala Ala Thr Gln Lys Lys Val Glu
1               5                   10                  15

Arg Lys Ala Pro Asp Ala Gly Gly Cys Leu His Ala Asp Pro Asp Leu
            20                  25                  30

Gly Val Leu Cys
        35

<210> SEQ ID NO 5
<211> LENGTH: 30
<212> TYPE: PRT
<213> ORGANISM: artificial
<220> FEATURE:
<223> OTHER INFORMATION: fragment Fg1.4

<400> SEQUENCE: 5

Leu Leu Leu Cys Val Phe Leu Val Lys Ser Gln Gly Val Asn Asp Asn
1               5                   10                  15

Glu Glu Gly Phe Phe Ser Ala Arg Gly His Arg Pro Leu Asp
            20                  25                  30

<210> SEQ ID NO 6
<211> LENGTH: 30
<212> TYPE: PRT
<213> ORGANISM: artificial
<220> FEATURE:
<223> OTHER INFORMATION: fragment Fg1.5
```

```
<400> SEQUENCE: 6

Ala Pro Ser Leu Arg Pro Ala Pro Pro Ile Ser Gly Gly Gly Tyr
1               5                   10                  15

Arg Ala Arg Pro Ala Lys Ala Ala Ala Thr Gln Lys Lys Val
            20                  25                  30

<210> SEQ ID NO 7
<211> LENGTH: 15
<212> TYPE: PRT
<213> ORGANISM: artificial
<220> FEATURE:
<223> OTHER INFORMATION: fragment Fg1.1.1

<400> SEQUENCE: 7

Leu Leu Leu Cys Val Phe Leu Val Lys Ser Gln Gly Val Asn Asp
1               5                   10                  15

<210> SEQ ID NO 8
<211> LENGTH: 5
<212> TYPE: PRT
<213> ORGANISM: artificial
<220> FEATURE:
<223> OTHER INFORMATION: fragment Fg1.1.2

<400> SEQUENCE: 8

Leu Leu Leu Cys Val
1               5

<210> SEQ ID NO 9
<211> LENGTH: 5
<212> TYPE: PRT
<213> ORGANISM: artificial
<220> FEATURE:
<223> OTHER INFORMATION: fragment Fg1.1.3

<400> SEQUENCE: 9

Phe Leu Val Lys Ser
1               5

<210> SEQ ID NO 10
<211> LENGTH: 5
<212> TYPE: PRT
<213> ORGANISM: artificial
<220> FEATURE:
<223> OTHER INFORMATION: fragment Fg1.1.4

<400> SEQUENCE: 10

Gln Gly Val Asn Asp
1               5

<210> SEQ ID NO 11
<211> LENGTH: 8
<212> TYPE: PRT
<213> ORGANISM: artificial
<220> FEATURE:
<223> OTHER INFORMATION: fragment Fg1.1.5

<400> SEQUENCE: 11

Leu Leu Leu Cys Val Phe Leu Val
1               5

<210> SEQ ID NO 12
<211> LENGTH: 7
<212> TYPE: PRT
<213> ORGANISM: artificial
```

```
<220> FEATURE:
<223> OTHER INFORMATION: fragment Fg1.1.6

<400> SEQUENCE: 12

Lys Ser Gln Gly Val Asn Asp
1               5

<210> SEQ ID NO 13
<211> LENGTH: 211
<212> TYPE: PRT
<213> ORGANISM: artificial
<220> FEATURE:
<223> OTHER INFORMATION: fragment Fg1

<400> SEQUENCE: 13

Met Lys Arg Met Val Ser Trp Ser Phe His Lys Leu Lys Thr Met Lys
1               5                   10                  15

His Leu Leu Leu Leu Leu Cys Val Phe Leu Val Lys Ser Gln Gly
                20                  25                  30

Val Asn Asp Asn Glu Glu Gly Phe Phe Ser Ala Arg Gly His Arg Pro
            35                  40                  45

Leu Asp Lys Lys Arg Glu Glu Ala Pro Ser Leu Arg Pro Ala Pro Pro
50                  55                  60

Pro Ile Ser Gly Gly Gly Arg Ala Arg Pro Ala Lys Ala Ala Ala Thr
65                  70                  75                  80

Gln Lys Lys Val Glu Arg Lys Ala Pro Asp Ala Gly Gly Cys Leu His
                85                  90                  95

Ala Asp Pro Asp Leu Gly Val Leu Cys Met Lys Arg Met Val Ser Trp
            100                 105                 110

Ser Phe His Lys Leu Lys Thr Met Lys His Leu Leu Leu Leu Leu Leu
        115                 120                 125

Cys Val Phe Leu Val Lys Ser Gln Gly Val Asn Asp Asn Glu Glu Gly
    130                 135                 140

Phe Phe Ser Ala Arg Gly His Arg Pro Leu Asp Lys Lys Arg Glu Glu
145                 150                 155                 160

Ala Pro Ser Leu Arg Pro Ala Pro Pro Ile Ser Gly Gly Gly Tyr
                165                 170                 175

Arg Ala Arg Pro Ala Lys Ala Ala Thr Gln Lys Lys Val Glu Arg
            180                 185                 190

Lys Ala Pro Asp Ala Gly Gly Cys Leu His Ala Asp Pro Asp Leu Gly
        195                 200                 205

Val Leu Cys
    210

<210> SEQ ID NO 14
<211> LENGTH: 147
<212> TYPE: PRT
<213> ORGANISM: artificial
<220> FEATURE:
<223> OTHER INFORMATION: fragment Fg2

<400> SEQUENCE: 14

Asp Ala Gly Gly Cys Leu His Ala Asp Pro Asp Leu Gly Val Leu Cys
1               5                   10                  15

Pro Thr Gly Cys Gln Leu Gln Glu Ala Leu Leu Gln Gln Glu Arg Pro
                20                  25                  30

Ile Arg Asn Ser Val Asp Glu Leu Asn Asn Asn Val Glu Ala Val Ser
            35                  40                  45
```

```
Gln Thr Ser Ser Ser Phe Gln Tyr Met Tyr Leu Leu Lys Asp Leu
    50                  55                  60

Trp Gln Lys Arg Gln Lys Gln Val Lys Asp Asn Glu Asn Val Val Asn
65                  70                  75                  80

Glu Tyr Ser Ser Glu Leu Glu Lys His Gln Leu Tyr Ile Asp Glu Thr
                85                  90                  95

Val Asn Ser Asn Ile Pro Thr Asn Leu Arg Val Leu Arg Ser Ile Leu
                100                 105                 110

Glu Asn Leu Arg Ser Lys Ile Gln Lys Leu Glu Ser Asp Val Ser Ala
                115                 120                 125

Gln Met Glu Tyr Cys Arg Thr Pro Cys Thr Val Ser Cys Asn Ile Pro
130                 135                 140

Val Val Ser
145

<210> SEQ ID NO 15
<211> LENGTH: 154
<212> TYPE: PRT
<213> ORGANISM: artificial
<220> FEATURE:
<223> OTHER INFORMATION: fragment Fg3

<400> SEQUENCE: 15

Lys Leu Glu Ser Asp Val Ser Ala Gln Met Glu Tyr Cys Arg Thr Pro
1               5                   10                  15

Cys Thr Val Ser Cys Asn Ile Pro Val Val Ser Gly Lys Glu Cys Glu
                20                  25                  30

Glu Ile Ile Arg Lys Gly Gly Glu Thr Ser Glu Met Tyr Leu Ile Gln
                35                  40                  45

Pro Asp Ser Ser Val Lys Pro Tyr Arg Val Tyr Cys Asp Met Asn Thr
    50                  55                  60

Glu Asn Gly Gly Trp Thr Val Ile Gln Asn Arg Gln Asp Gly Ser Val
65                  70                  75                  80

Asp Phe Gly Arg Lys Trp Asp Pro Tyr Lys Gln Gly Phe Gly Asn Val
                85                  90                  95

Ala Thr Asn Thr Asp Gly Lys Asn Tyr Cys Gly Leu Pro Gly Glu Tyr
                100                 105                 110

Trp Leu Gly Asn Asp Lys Ile Ser Gln Leu Thr Arg Met Gly Pro Thr
                115                 120                 125

Glu Leu Leu Ile Glu Met Glu Asp Trp Lys Gly Asp Lys Val Lys Ala
                130                 135                 140

His Tyr Gly Gly Phe Thr Val Gln Asn Glu
145                 150

<210> SEQ ID NO 16
<211> LENGTH: 154
<212> TYPE: PRT
<213> ORGANISM: artificial
<220> FEATURE:
<223> OTHER INFORMATION: fragment Fg4

<400> SEQUENCE: 16

Pro Thr Glu Leu Leu Ile Glu Met Glu Asp Trp Lys Gly Asp Lys Val
1               5                   10                  15

Lys Ala His Tyr Gly Gly Phe Thr Val Gln Asn Glu Ala Asn Lys Tyr
                20                  25                  30

Gln Ile Ser Val Asn Lys Tyr Arg Gly Thr Ala Gly Asn Ala Leu Met
                35                  40                  45
```

Asp Gly Ala Ser Gln Leu Met Gly Glu Asn Arg Thr Met Thr Ile His
     50                  55                  60

Asn Gly Met Phe Phe Ser Thr Tyr Asp Arg Asp Asn Asp Gly Trp Leu
 65                  70                  75                  80

Thr Ser Asp Pro Arg Lys Gln Cys Ser Lys Glu Asp Gly Gly Trp
                 85                  90                  95

Trp Tyr Asn Arg Cys His Ala Ala Asn Pro Asn Gly Arg Tyr Tyr Trp
                100                 105                 110

Gly Gly Gln Tyr Thr Trp Asp Met Ala Lys His Gly Thr Asp Asp Gly
             115                 120                 125

Val Val Trp Met Asn Trp Lys Gly Ser Trp Tyr Ser Met Arg Lys Met
 130                 135                 140

Ser Met Lys Ile Arg Pro Phe Phe Pro Gln
145                 150

<210> SEQ ID NO 17
<211> LENGTH: 33
<212> TYPE: DNA
<213> ORGANISM: artificial
<220> FEATURE:
<223> OTHER INFORMATION: primer

<400> SEQUENCE: 17
gcaggaattc tgatgaaaag gatggtttct tgg        33

<210> SEQ ID NO 18
<211> LENGTH: 33
<212> TYPE: DNA
<213> ORGANISM: artificial
<220> FEATURE:
<223> OTHER INFORMATION: primer

<400> SEQUENCE: 18
ggccgctcga gtacacaaca cccccaggtc tgg        33

<210> SEQ ID NO 19
<211> LENGTH: 33
<212> TYPE: DNA
<213> ORGANISM: artificial
<220> FEATURE:
<223> OTHER INFORMATION: primer

<400> SEQUENCE: 19
gcaggaattc tggatgctgg aggctgtctt cac        33

<210> SEQ ID NO 20
<211> LENGTH: 33
<212> TYPE: DNA
<213> ORGANISM: artificial
<220> FEATURE:
<223> OTHER INFORMATION: primer

<400> SEQUENCE: 20
ggccgctcga ctagacacca caggaatatt gca        33

<210> SEQ ID NO 21
<211> LENGTH: 33
<212> TYPE: DNA
<213> ORGANISM: artificial
<220> FEATURE:
<223> OTHER INFORMATION: primer -continued

<400> SEQUENCE: 21
gcaggaattc tgaagttaga atctgatgtc tca                      33

<210> SEQ ID NO 22
<211> LENGTH: 33
<212> TYPE: DNA
<213> ORGANISM: artificial
<220> FEATURE:
<223> OTHER INFORMATION: primer

<400> SEQUENCE: 22
ggccgctcga gtttcattct gtacagtgaa tcc                      33

<210> SEQ ID NO 23
<211> LENGTH: 33
<212> TYPE: DNA
<213> ORGANISM: artificial
<220> FEATURE:
<223> OTHER INFORMATION: primer

<400> SEQUENCE: 23
gcaggaattc tgcccacaga acttttgata gaa                      33

<210> SEQ ID NO 24
<211> LENGTH: 33
<212> TYPE: DNA
<213> ORGANISM: artificial
<220> FEATURE:
<223> OTHER INFORMATION: primer

<400> SEQUENCE: 24
ggccgctcga gtctgtggga agaagggcct gat                      33

<210> SEQ ID NO 25
<211> LENGTH: 5
<212> TYPE: PRT
<213> ORGANISM: artificial
<220> FEATURE:
<223> OTHER INFORMATION: fragment of P.acnes Pfg protein

<400> SEQUENCE: 25

Ala Gly Ile Asp Lys
1               5

<210> SEQ ID NO 26
<211> LENGTH: 9
<212> TYPE: PRT
<213> ORGANISM: artificial
<220> FEATURE:
<223> OTHER INFORMATION: fragment of P.acnes Pfg protein

<400> SEQUENCE: 26

Ala Ala Ile Ala Gly Ala Leu Val Lys
1               5

<210> SEQ ID NO 27
<211> LENGTH: 7
<212> TYPE: PRT
<213> ORGANISM: artificial
<220> FEATURE:
<223> OTHER INFORMATION: fragment of P.acnes Pfg protein

<400> SEQUENCE: 27

Thr Ala Glu Gln Leu Glu Lys
1               5

```
<210> SEQ ID NO 28
<211> LENGTH: 7
<212> TYPE: PRT
<213> ORGANISM: artificial
<220> FEATURE:
<223> OTHER INFORMATION: fragment of P.acnes Pfg protein

<400> SEQUENCE: 28

Ile Val Thr His Leu Val Arg
1               5

<210> SEQ ID NO 29
<211> LENGTH: 10
<212> TYPE: PRT
<213> ORGANISM: artificial
<220> FEATURE:
<223> OTHER INFORMATION: fragment of P.acnes Pfg protein

<400> SEQUENCE: 29

Ala Ala Ala Ala Val Asp Leu Gly Ile Lys
1               5                   10

<210> SEQ ID NO 30
<211> LENGTH: 9
<212> TYPE: PRT
<213> ORGANISM: artificial
<220> FEATURE:
<223> OTHER INFORMATION: fragment of P.acnes Pfg protein

<400> SEQUENCE: 30

Ser Leu Ala Val Gln Ile Ala Pro Arg
1               5

<210> SEQ ID NO 31
<211> LENGTH: 9
<212> TYPE: PRT
<213> ORGANISM: artificial
<220> FEATURE:
<223> OTHER INFORMATION: fragment of P.acnes Pfg protein

<400> SEQUENCE: 31

Ala Ala Ile Glu His Ile Ile Gly Arg
1               5

<210> SEQ ID NO 32
<211> LENGTH: 10
<212> TYPE: PRT
<213> ORGANISM: artificial
<220> FEATURE:
<223> OTHER INFORMATION: fragment of P.acnes Pfg protein

<400> SEQUENCE: 32

Glu Pro Leu Leu Ala Leu Asn Thr Ala Lys
1               5                   10

<210> SEQ ID NO 33
<211> LENGTH: 10
<212> TYPE: PRT
<213> ORGANISM: artificial
<220> FEATURE:
<223> OTHER INFORMATION: fragment of P.acnes Pfg protein

<400> SEQUENCE: 33

Gln Ile Val Asp Val Ile Thr Ala Asp Lys
1               5                   10
```

```
<210> SEQ ID NO 34
<211> LENGTH: 10
<212> TYPE: PRT
<213> ORGANISM: artificial
<220> FEATURE:
<223> OTHER INFORMATION: fragment of P.acnes Pfg protein

<400> SEQUENCE: 34

Gln Ile Val Asp Val Ile Thr Ala Asp Lys
1               5                   10

<210> SEQ ID NO 35
<211> LENGTH: 10
<212> TYPE: PRT
<213> ORGANISM: artificial
<220> FEATURE:
<223> OTHER INFORMATION: fragment of P.acnes Pfg protein

<400> SEQUENCE: 35

Lys Ala Ala Ile Glu His Ile Ile Gly Arg
1               5                   10

<210> SEQ ID NO 36
<211> LENGTH: 10
<212> TYPE: PRT
<213> ORGANISM: artificial
<220> FEATURE:
<223> OTHER INFORMATION: fragment of P.acnes Pfg protein

<400> SEQUENCE: 36

Glu Leu Pro Ala Leu Asp Asp Leu Val Lys
1               5                   10

<210> SEQ ID NO 37
<211> LENGTH: 10
<212> TYPE: PRT
<213> ORGANISM: artificial
<220> FEATURE:
<223> OTHER INFORMATION: fragment of P.acnes Pfg protein

<400> SEQUENCE: 37

Glu Gly Val Leu Leu Ile Asn His His Lys
1               5                   10

<210> SEQ ID NO 38
<211> LENGTH: 13
<212> TYPE: PRT
<213> ORGANISM: artificial
<220> FEATURE:
<223> OTHER INFORMATION: fragment of P.acnes Pfg protein

<400> SEQUENCE: 38

Ala Glu Ile Ala Ala Gln Ala Ala Leu Leu Val Gly Arg
1               5                   10

<210> SEQ ID NO 39
<211> LENGTH: 14
<212> TYPE: PRT
<213> ORGANISM: artificial
<220> FEATURE:
<223> OTHER INFORMATION: fragment of P.acnes Pfg protein

<400> SEQUENCE: 39

Ala Gly Phe Ser Ser Ala Asp Ala Val Ala Leu Ala Pro Arg
1               5                   10
```

```
<210> SEQ ID NO 40
<211> LENGTH: 14
<212> TYPE: PRT
<213> ORGANISM: artificial
<220> FEATURE:
<223> OTHER INFORMATION: fragment of P.acnes Pfg protein

<400> SEQUENCE: 40

Asp Ala Val Val Ala Asn Leu Val Ala Ala Gly Val Asp Lys
1               5                   10

<210> SEQ ID NO 41
<211> LENGTH: 15
<212> TYPE: PRT
<213> ORGANISM: artificial
<220> FEATURE:
<223> OTHER INFORMATION: fragment of P.acnes Pfg protein

<400> SEQUENCE: 41

Asp Ala Val Val Ala Asn Leu Val Ala Ala Gly Val Asp Lys Lys
1               5                   10                  15

<210> SEQ ID NO 42
<211> LENGTH: 17
<212> TYPE: PRT
<213> ORGANISM: artificial
<220> FEATURE:
<223> OTHER INFORMATION: fragment of P.acnes Pfg protein

<400> SEQUENCE: 42

Ala Gly Phe Ser Ser Ala Asp Ala Val Ala Leu Ala Pro Arg Ile Ala
1               5                   10                  15

Lys

<210> SEQ ID NO 43
<211> LENGTH: 18
<212> TYPE: PRT
<213> ORGANISM: artificial
<220> FEATURE:
<223> OTHER INFORMATION: fragment of P.acnes Pfg protein

<400> SEQUENCE: 43

Ala Thr Leu Ala Ala Thr Ile Ile Pro Asn Ala Leu His Ser Ala Ala
1               5                   10                  15

Phe Lys

<210> SEQ ID NO 44
<211> LENGTH: 20
<212> TYPE: PRT
<213> ORGANISM: artificial
<220> FEATURE:
<223> OTHER INFORMATION: fragment of P.acnes Pfg protein

<400> SEQUENCE: 44

Ala Thr Ala Val Ala Ile Ala Thr Ala Leu Asn Pro Ala Leu Gly
1               5                   10                  15

Pro Ile Ala Lys
            20

<210> SEQ ID NO 45
<211> LENGTH: 19
<212> TYPE: PRT
<213> ORGANISM: artificial
<220> FEATURE:
<223> OTHER INFORMATION: fragment of P.acnes Pfg protein
```

```
<400> SEQUENCE: 45

Ser Phe Asp Ala Ala Val Ala Thr Ala Ile Val Ser Ser Pro Ile Leu
1               5                   10                  15

Asn Ala Arg

<210> SEQ ID NO 46
<211> LENGTH: 33
<212> TYPE: PRT
<213> ORGANISM: artificial
<220> FEATURE:
<223> OTHER INFORMATION: fragment of P.acnes Pfg protein

<400> SEQUENCE: 46

Ser Gly Gly His Ser Gln Gly Ser Gly Thr His Tyr Ile His His
1               5                   10                  15

Gly Val Ala Pro Val Leu Thr His Ser Ser Asp Leu Pro Ser Thr Gly
            20                  25                  30

Phe

<210> SEQ ID NO 47
<211> LENGTH: 106
<212> TYPE: PRT
<213> ORGANISM: artificial
<220> FEATURE:
<223> OTHER INFORMATION: fragment Fg1

<400> SEQUENCE: 47

Met Lys Arg Met Val Ser Trp Ser Phe His Lys Leu Lys Thr Met Lys
1               5                   10                  15

His Leu Leu Leu Leu Leu Leu Cys Val Phe Leu Val Lys Ser Gln Gly
            20                  25                  30

Val Asn Asp Asn Glu Glu Gly Phe Phe Ser Ala Arg Gly His Arg Pro
        35                  40                  45

Leu Asp Lys Lys Arg Glu Glu Ala Pro Ser Leu Arg Pro Ala Pro Pro
    50                  55                  60

Pro Ile Ser Gly Gly Gly Tyr Arg Ala Arg Pro Ala Lys Ala Ala Ala
65                  70                  75                  80

Thr Gln Lys Lys Val Glu Arg Lys Ala Pro Asp Ala Gly Gly Cys Leu
                85                  90                  95

His Ala Asp Pro Asp Leu Gly Val Leu Cys
            100                 105
```

ISOLATED PEPTIDES AND FRAGMENTS THEREOF FROM FIBRINOGEN FOR USE AS DRUGS, PARTICULARLY IN SKIN INFLAMMATORY DISEASES

CROSS-REFERENCE TO RELATED APPLICATIONS

This application is a U.S. National Stage Application pursuant to 35 U.S.C. § 371 of International Patent Application PCT/EP2016/056179, filed on Mar. 21, 2016, and published as WO 2016/150926 on Sep. 29, 2016, which claims priority to European Patent Application 15305414.3, filed on Mar. 20, 2015, all of which are incorporated herein by reference in their entireties for all purposes.

TECHNICAL FIELD OF THE INVENTION

The present invention is in the medical field, particularly in the field of inflammatory skin diseases and more particularly, the present invention relates to isolated peptides obtained from human fibrinogen for their use as drug, particularly for the prevention and/or the treatment of inflammatory skin diseases, more particularly acne. The present invention also relates to fragments of these polypeptides, nucleic acid molecules encoding them, expression vectors, host cells, a pharmaceutical composition and a combination product containing them, and their use for treating and/or preventing inflammatory skin diseases, particularly acne.

BACKGROUND OF THE INVENTION

Inflammatory skin disorders cover a broad category that includes many conditions ranging in severity, from mild itching to serious medical health complications. These disorders are common in people of all ages and races. They are characterized by irritation and inflammation of the skin. These diseases may sometimes be disfiguring and can cause great discomfort to the affected individual. A well-known example of inflammatory skin disorder is acne.

Acne is a multifactorial disease of the skin affecting more than 80% of young adults. This disease is localized to the pilosebaceous follicle and characterized by both inflammatory and non inflammatory lesions. Patients may present a mixture of non inflammatory comedons and inflammatory papules, pustules and nodules. One of the factors promoting the development of inflammatory acne is the bacterial colonization of the pilosebaceus duct by the anaerobic *Proprionibacterium acnes* (*P. acnes*) strain.

Indeed, *P. acnes* is able to induce in vitro production of proinflammatory molecules (interleukins IL-1α/ß, IL-8, IL-12, TNF-α, ß-defensins) by keratinocytes, sebocytes and monocytes but also in vivo in acne lesions. This production involves TLR2 receptor and activation of the NF-κB and MAPK signaling pathways as well as the NLRP3 inflammasome pathway. *P. acnes* also induces a massive production of reactive oxygen species (ROS) by keratinocytes, contributing to the initiation of the inflammatory reaction (Graham 2004; Grange 2009a; Grange 2009b; Kang 2005; Nagy 2005; Trivedi 2006; Qin 2014; Kistowska 2014, Jugeau 2005).

Currently, there are several anti-acne treatments such as retinoid (vitamin A derivatives), azelaic acid, salicylic acid, benzoil peroxide, topical and oral antibiotics etc.

These treatments act differently and have different effects. Generally, antibiotics kill bacteria, retinoid and azalaic acid prevent the development of microcomedones and have antimicrobial and anti-inflammatory properties etc.

Other chemical compounds target specific mechanisms linked to bacterial invasion.

*P. acnes* can adhere to human skin (Grice 2009) but also can cause deeper infections by travelling from its seeded area to the site of infection using non specific interactions and then irreversible adhesion process through specific binding (Gristina 1988). Moreover, previous study has shown the ability of *P. acnes* to bind to extracellular matrix proteins (ECM) as fibronectin (Yu 1997), as well as to human epithelial cell (Romero-Steiner 1990).

Among chemical drug having anti-adhesive agent, Papulex® is well known.

However, the above-cited treatments have many side effects. For example, antibiotic courses should be limited in the time and often, desensitization or loss of response is observed. Moreover, the use of chemical compounds induces several risks for patients, such as hypopigmentation in darker skinned patients or other side effects due to the treatment intolerance. Another drawback of using chemical compound for treating acne is their high cost (Dawson et, 2013).

For these reasons, other means, preferably biological means for treating and preventing acne should be developed allowing good efficiency of treatment without side effects and low production cost.

SUMMARY OF THE INVENTION

In the context of the present invention, the inventors have now identified a *P. acnes* surface protein of 58-kDa specifically recognized by human fibrinogen and named it Pfg. More particularly, the inventors have found that a subunit of human fibrinogen is able to specifically bind the adhesion protein Pfg ant thus to inhibit its adhesion to *P. acnes*.

This finding was not expected since, as well as inventors know, it is the first time that a *P. acnes* surface glycoprotein with the ability to recognize human fibrinogen was characterized.

This finding is very important because it allows developing alternative means for treating acne by inhibiting bacterial adhesion to skin cells and thus preventing and/or treating the skin infection and inflammation induced by bacterial adhesion. In addition, the inventors found that said fibrinogen subunit has more general anti-inflammatory properties and may thus more generally be used for preventing and/or treating other inflammatory skin disorders, preferably psoriasis In a first aspect, the present invention thus relates to an isolated polypeptide comprising an amino acid sequence with at least 80% identity with SEQ ID NO: 1 after optimal global alignment, or a fragment thereof comprising an amino acid sequence with at least 80% identity with anyone of SEQ ID NOs: 2, 5 and 7 to 13 and 47 after optimal global alignment, for use as a medicament.

The SEQ ID NO: 1 corresponds to human Bß sub-unit of fibrinogen, while SEQ ID NOs: 2, 5 and 7 to 13 and 47 correspond to fragments of this sequence.

The polypeptide according to the invention is able to recognize and to bind to *P. acnes*, and also to inhibit the adhesion of *P. acnes* to its ligand fibrinogen and to skin cells.

Thus, the polypeptide for therapeutic use according to the present invention may be used preferably for preventing and/or treating acne.

The inventors have also found that the isolated polypeptide for therapeutic use according to the invention may be used for the treatment and/or the prevention of other inflammatory skin diseases, preferably psoriasis.

The inventors have also isolated fragments of human fibrinogen Bβ sub-unit recognizing and binding to the adhesion protein of P. acnes, and inhibiting the adhesion of P. acnes to its ligand fibrinogen and to skin cells.

In a second aspect, the present invention thus relates to a fragment of a polypeptide comprising an amino acid sequence with at least 80% identity with of SEQ ID NO: 1 after optimal global alignment, said fragment comprising an amino acid sequence with at least 80% identity with anyone of SEQ ID NOs: 2, 5 and 7 to 13 and 47 after optimal global alignment.

In a third aspect, the invention also relates to an isolated nucleic acid molecule encoding the fragments of the invention, to a vector comprising the nucleic acid of the invention, and a host cell comprising the nucleic acid molecule according to the invention or the vector according to the invention.

The fragments of the invention are able to recognize and to bind to P. acnes, and also to inhibit the adhesion of P. acnes to its ligand fibrinogen and to skin cells. Consequently, these fragments may have a great potential as anti-adhesion agent in drug for preventing and/or treating inflammatory diseases, particularly acne.

In a fourth aspect, the invention thus relates to a pharmaceutical composition comprising at least one compound selected from the fragment, the isolated nucleic acid molecule, the vector or the host cell according to the invention, and a pharmaceutically acceptable vehicle.

The present invention also relates to the isolated nucleic acid molecule, the vector, the host cell or the pharmaceutical composition according to the invention, for use as a medicament.

Preferably the isolated nucleic acid molecule, the vector, the host cell or the pharmaceutical composition according to the invention are used for the treatment and/or the prevention of acne.

The inventors have also found that the isolated nucleic acid molecule, the vector, the host cell or the pharmaceutical composition according to the invention may be used for the treatment and/or the prevention of other inflammatory skin diseases, preferably psoriasis.

The fragment, the isolated nucleic acid molecule, the vector, the host cell or the pharmaceutical composition of the present invention may be used alone or in combination with another therapeutic agent involving in acne prevention and/or treatment and/or of the prevention and/or treatment of other inflammatory diseases, preferably psoriasis.

In a fifth aspect, the present invention thus relates to a combination product comprising:
  at least one compound selected from the fragment, the isolated nucleic acid molecule, the vector and the host cell according to the invention; and
  another pharmaceutical agent, preferably used for the treatment and/or the prevention of skin inflammatory diseases selected from psoriasis and/or acne, preferably acne;
  for simultaneous, separate or sequential use as a medicament.

The purpose of the combination product according to the invention is enhancing the therapeutic effect of the fragment according to the invention.

Figure 18:
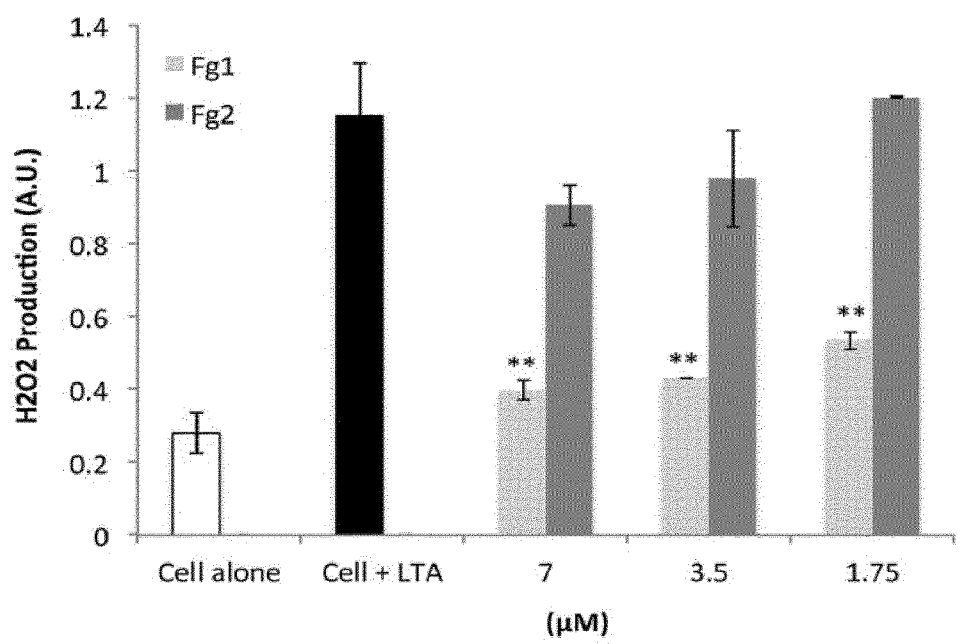

FIG. 18: Dose-dependent inhibition of $H_2O_2$ production by keratinocyte pre-treated by small Fg1-generated peptides and stimulated by lipoteichoic acid (LTA). NHDK cell were incubated for 24 h with recombinant peptide Fg1 (light gray bar) and Fg2 (dark gray bar) at concentrations ranging from 1.75 to 7 µM. Measurement of hydrogen peroxide production was realized by spectrofluorometry as described in Materials and Methods. Controls experiments were done with unstimulated NHDK cell (white bar) and HDF stimulated with LTA at 10 µg/ml (black bar). Data are means±S.D. of three separate experiments. Statistical significance is indicated by * (P<0.05),  (P<0.01), * (P<0.001), and **** (P<0.0001), respectively.

Figure 19:
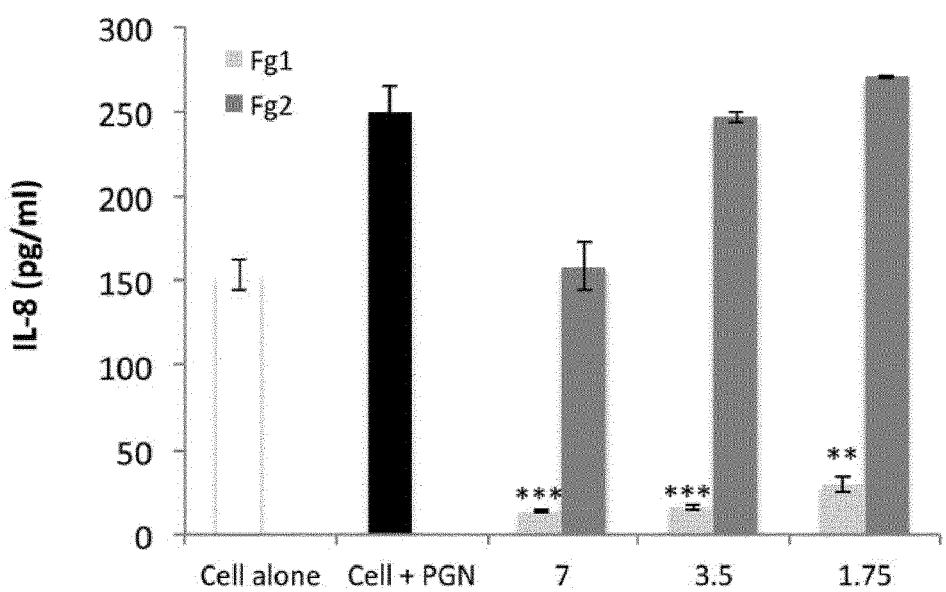

FIG. 19: Dose-dependent inhibition of IL-8 production by keratinocyte pre-treated by small Fg1-generated peptides and stimulated by peptidoglycanne (PGN). NHDK cell were incubated for 24 h with recombinant peptide Fg1 (light gray bar) and Fg2 (dark gray bar) at concentrations ranging from 1.75 to 7 µM. Measurement of IL-8 production was realized by ELISA as described in Materials and Methods. Controls experiments were done with unstimulated NHDK cell (white bar) and HDF stimulated with PGN at 10 µg/ml (black bar). Data are means±S.D. of three separate experiments. Statistical significance is indicated by * (P<0.05),  (P<0.01), * (P<0.001), and **** (P<0.0001), respectively.

Figure 20:
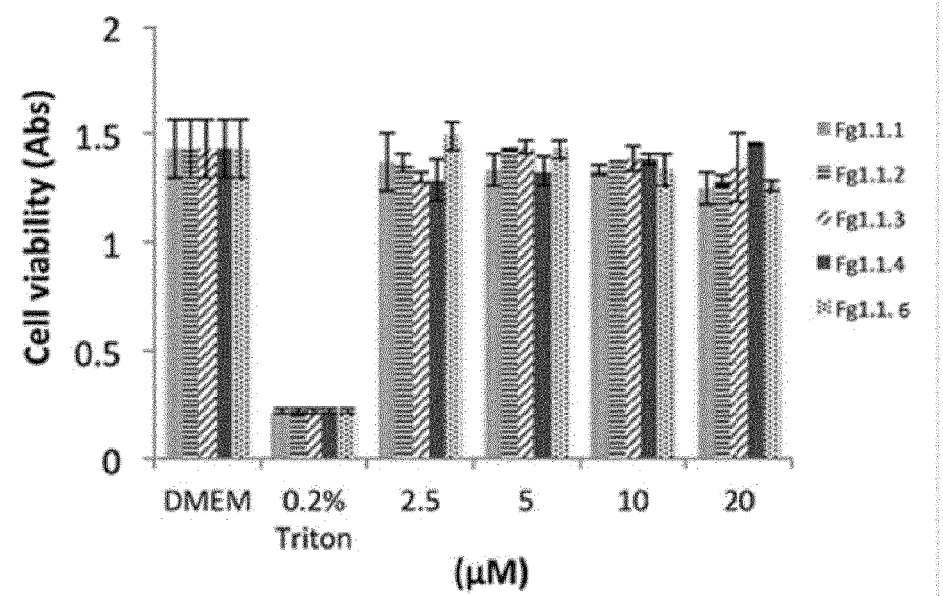

FIG. 20: Evaluation of cell viability after treatment with small Fg1.1-generated peptides on keratinocytes. HaCaT cell were incubated for 24 h with small peptides Fg1.1.1 (light gray bar), Fg1.1.2 (horizontal line bar), Fg1.1.3 (hatched bar), Fg1.1.4 (dark gray bar), Fg1.1.6 (dotted bar) at concentrations ranging from 2.5 to 20 µM. Measurement of cytotoxicity was determined by the MTT assay as described in Materials and Methods. Controls experiments were done with HaCaT cell incubated with PBS (corresponding to viable cells); and with 0.2% triton X100 (corresponding to dead cells). Data are means±S.D. of three separate experiments.

Figure 21:
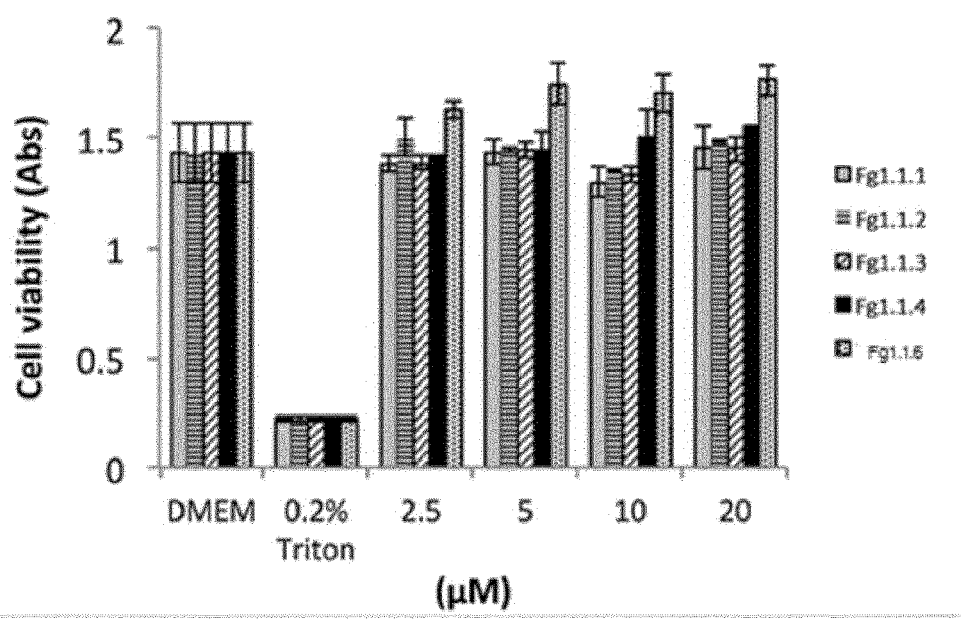

FIG. 21: Evaluation of cell viability after treatment with vehicle used to prepare Fg1.1-generated peptides solution on keratinocytes. HaCaT cell were incubated for 24 h with vehicle diluted solutions corresponding to the conditions used with Fg1.1.1 (light gray bar), Fg1.1.2 (horizontal line bar), Fg1.1.3 (hatched bar), Fg1.1.4 (dark gray bar), Fg1.1.6 (dotted bar). Measurement of cytotoxicity was determined by the MTT assay as described in Materials and Methods. Controls experiments were done with HaCaT cell incubated with PBS (corresponding to viable cells); and with 0.2% triton X100 (corresponding to dead cells). Data are means±S.D. of three separate experiments.

Figure 22:
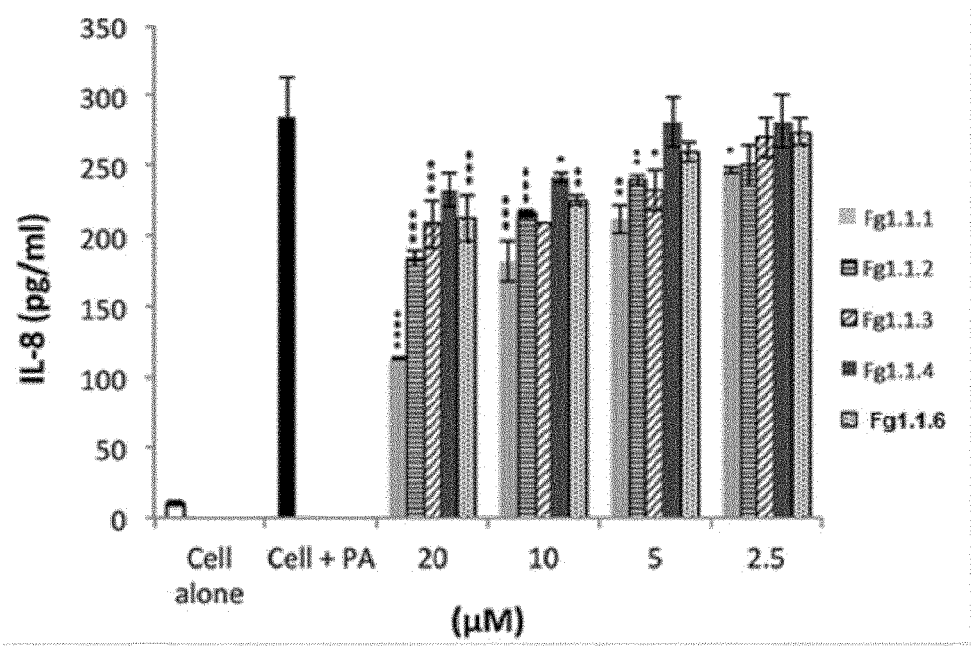

FIG. 22: Dose-dependent inhibition of IL-8 production by keratinocytes stimulated by *P. acnes* pre-treated with small Fg1.1-generated peptides. HaCaT cell were incubated for 24 h with small peptides Fg1.1.1 (light gray bar), Fg1.1.2 (horizontal line bar), Fg1.1.3 (hatched bar), Fg1.1.4 (dark gray bar), Fg1.1.6 (dotted bar) at concentrations ranging from 2.5 to 20 µM. Measurement of IL-8 production was realized by ELISA as described in Materials and Methods. Controls experiments were done with unstimulated HaCaT cell (white bar) and HaCaT stimulated with *P. acnes* (black bar). Data are means±S.D. of three separate experiments. Statistical significance is indicated by * (P<0.05),  (P<0.01), * (P<0.001), and **** (P<0.0001), respectively.

Figure 23:
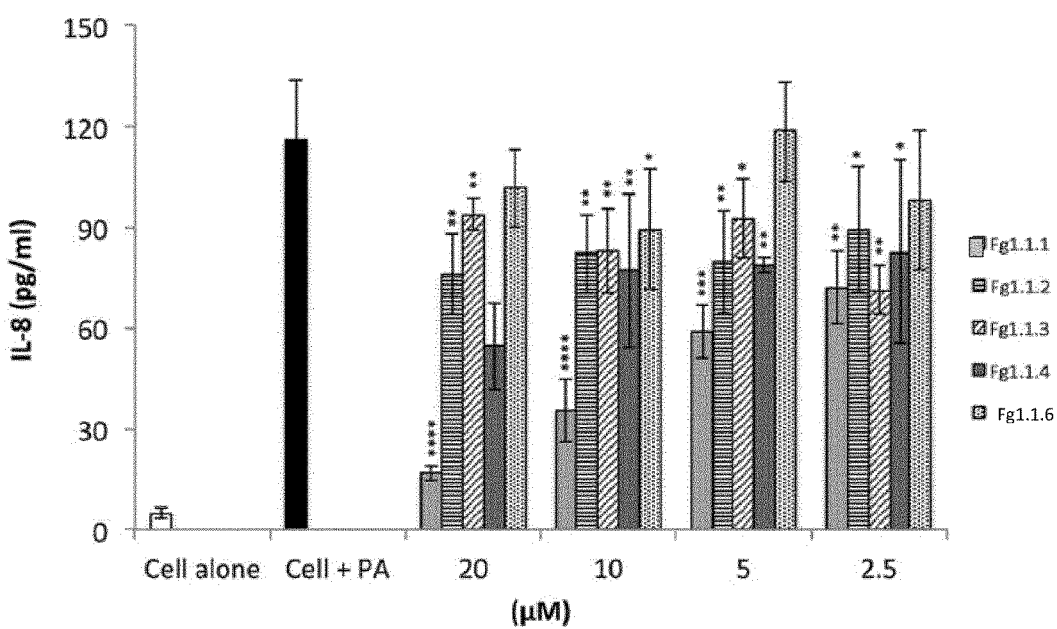

FIG. 23: Dose-dependent inhibition of IL-8 production by fibroblasts pre-treated by small Fg1.1-generated peptides and stimulated by *P. acnes*. MCR5 cell were incubated for 24 h with small peptides Fg1.1.1 (light gray bar), Fg1.1.2 (horizontal line bar), Fg1.1.3 (hatched bar), Fg1.1.4 (dark gray bar), Fg1.1.6 (dotted bar) at concentrations ranging from 2.5 to 20 µM. Measurement of IL-8 production was realized by ELISA as described in Materials and Methods. Controls experiments were done with unstimulated MCR5 cell (white bar) and MCR5 stimulated with *P. acnes* (black bar). Data are means±S.D. of three separate experiments. Statistical significance is indicated by * (P<0.05),  (P<0.01), * (P<0.001), and **** (P<0.0001), respectively.

Figure 24:
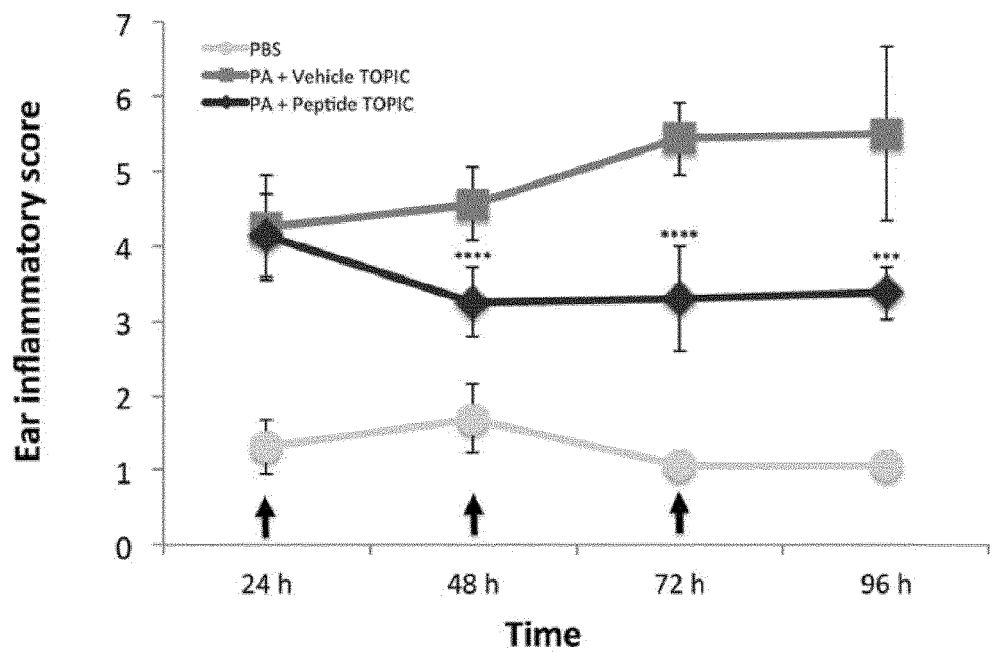

FIG. 24: Effect of 5% Fg1.1.1 peptide gel on *P. acnes*-induced inflammation in vivo. Ears of mice were intradermally injected with *P. acnes* ($OD_{620nm}$=1.0 corresponding to $2.10^7$ CFU/20 µl in PBS) to induce inflammation. Subsequently, 5% Fg1.1.1 peptide gel was applied on the ear skin surface of mice each day for 3 days (arrows). The score corresponding to the ear thickness, the peeling and the redness, was measured every day for a period of 96 h. Data are means±S.D. of eight individual experiments. PBS corresponds to the non-treated group injected with PBS. PA+Vehicle TOPIC corresponds to *P. acnes* injected in ears treated with vaseline alone. PA+Peptide TOPIC corresponds to *P. acnes* injected in ears treated with 5% Fg1.1.1 peptide mixed in vaseline. Statistical significance is indicated by * (P<0.05),  (P<0.01), * (P<0.001), and **** (P<0.0001), respectively.

Figure 25:
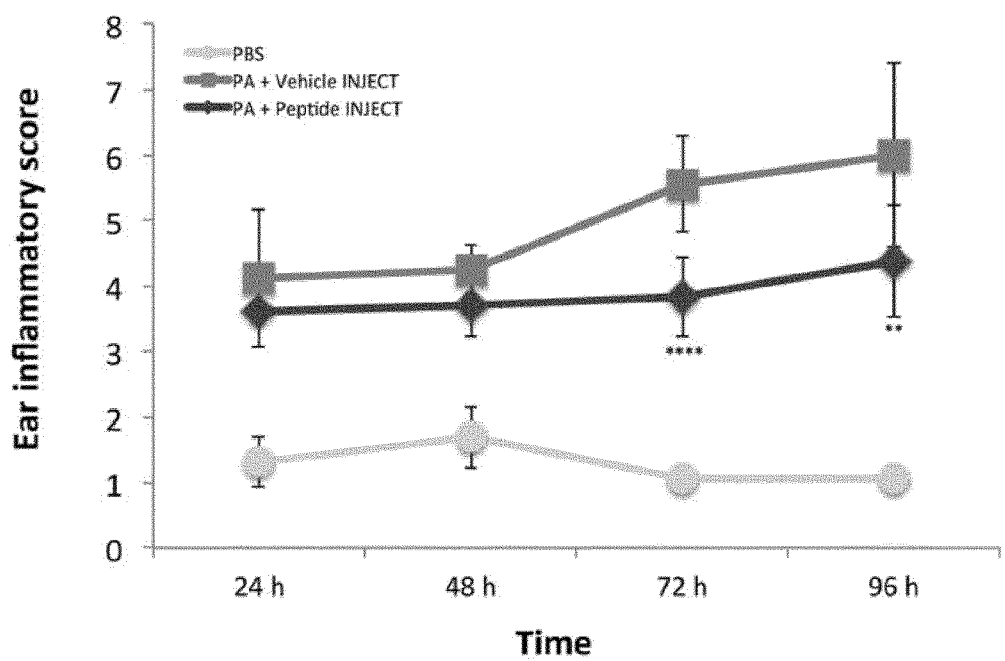

FIG. 25: Effect of Fg1.1.1 peptide on *P. acnes*-induced inflammation in vivo, wherein *P. acnes* was pre-treated with Fg1.1.1. *P. acnes* strain ($OD_{620nm}$=1.5) was pre-treated for 1 h at 37° C. with Fg1.1.1 peptide (140 µM) (PA+Peptide INJECT) or with the vehicle (1% DMSO final in PBS) (PA+Vehicle INJECT) and then intradermally injected in ears of mice (approximately $2.0^7$ CFU/20 µl) to induce inflammation. Control group was injected with PBS alone. The score corresponding to the ear thickness, the peeling and the redness, was measured every day for a period of 96 h. Data are means±S.D. of eight individual experiments. Statistical significance is indicated by * (P<0.05),  (P<0.01), * (P<0.001), and **** (P<0.0001), respectively.

Figure 26:
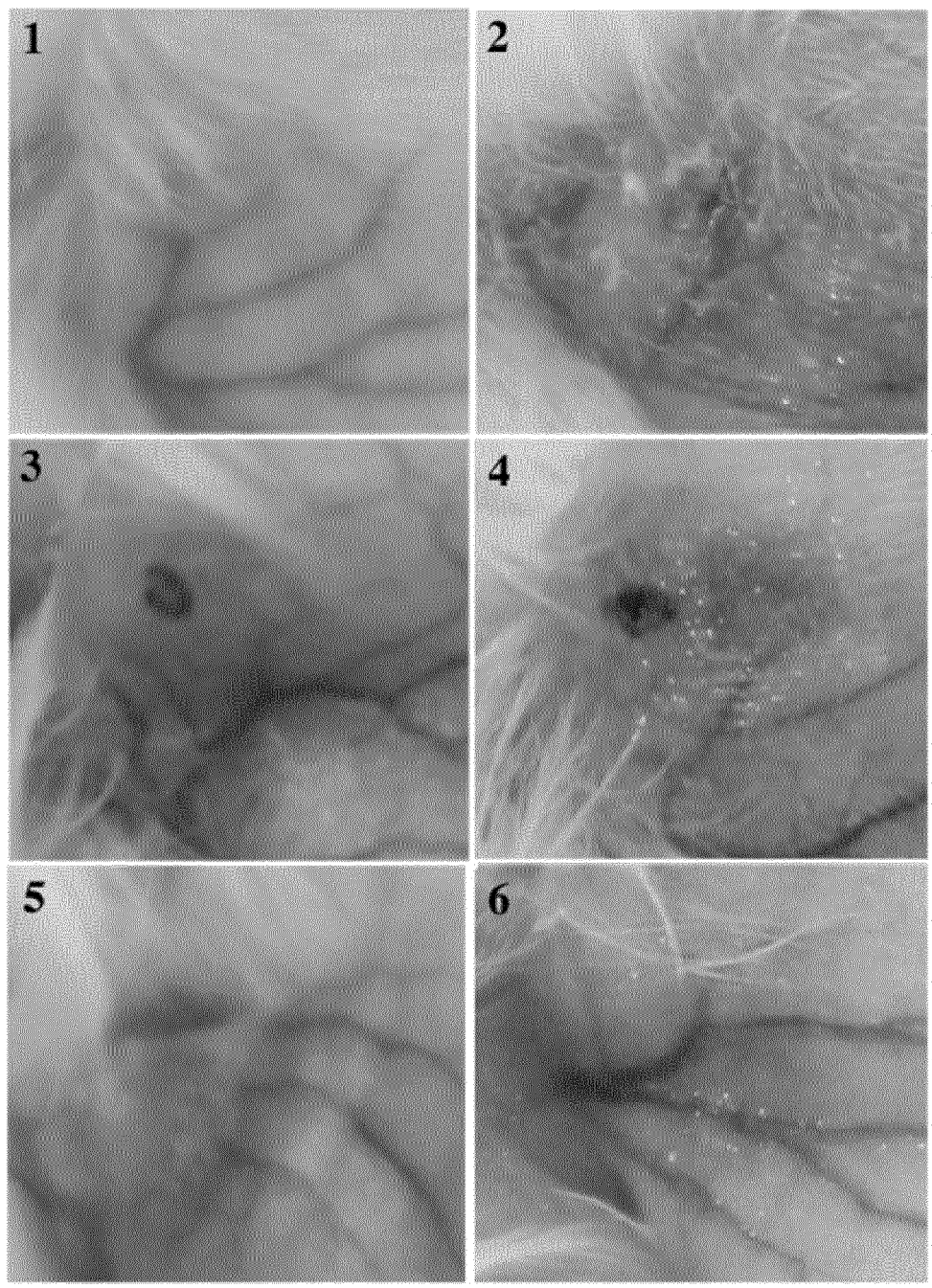

FIG. 26: Effects of intradermal injection and topical application of Fg1.1.1 peptide on *P. acnes*-induced inflammation in mice. (1) Ear injected with only PBS. (2) After 96 h of *P. acnes* challenge ($2.10^7$ CFU/20 µl in PBS). (3) After 96 h of *P. acnes* mixed with 1% DMSO final. (4) After 96 h of *P. acnes* challenge with vaseline topical application. (5) After 96 h of *P. acnes* mixed with Fg1.1.1 peptide. (6) After 96 h of *P. acnes* challenge with Fg1.1.1 peptide topical application.

Figure 27:
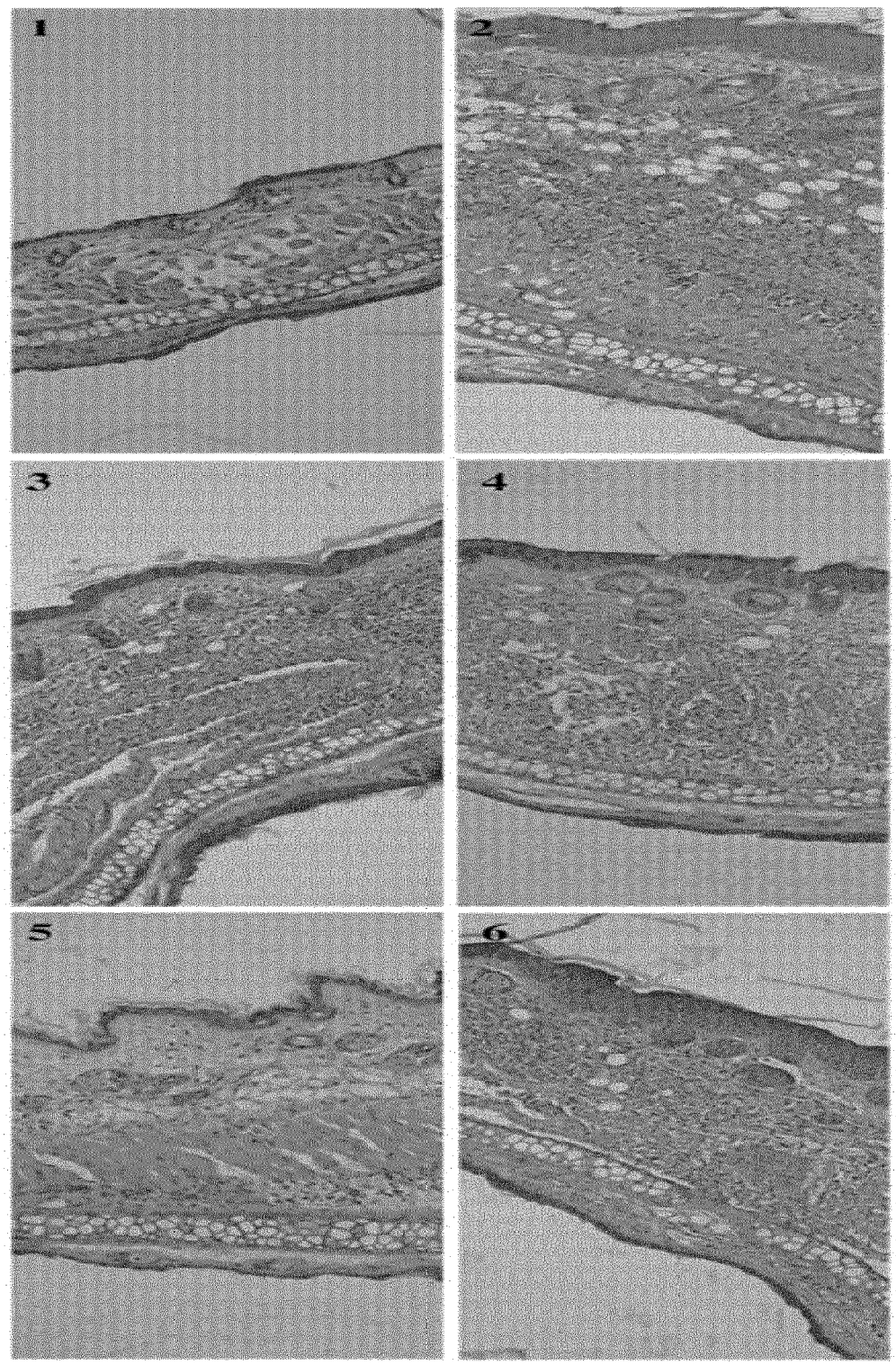

FIG. 27: Histopathological analysis of mouse ears. (1) Ear injected with only PBS. (2) After 96 h of *P. acnes* challenge ($2.10^7$ CFU/20 µl in PBS), ear swelling and infiltrated inflammatory cells. (3 and 4) Ear swelling and mostly infiltrated inflammatory cells has not been changed by vehicle injection and application, respectively. (5 and 6) Ear swelling and infiltrated inflammatory cells have been reduced by Fg1.1.1 peptide injection and topical application, respectively. Data are representative of eight individual experiments with similar results.

Figure 28:
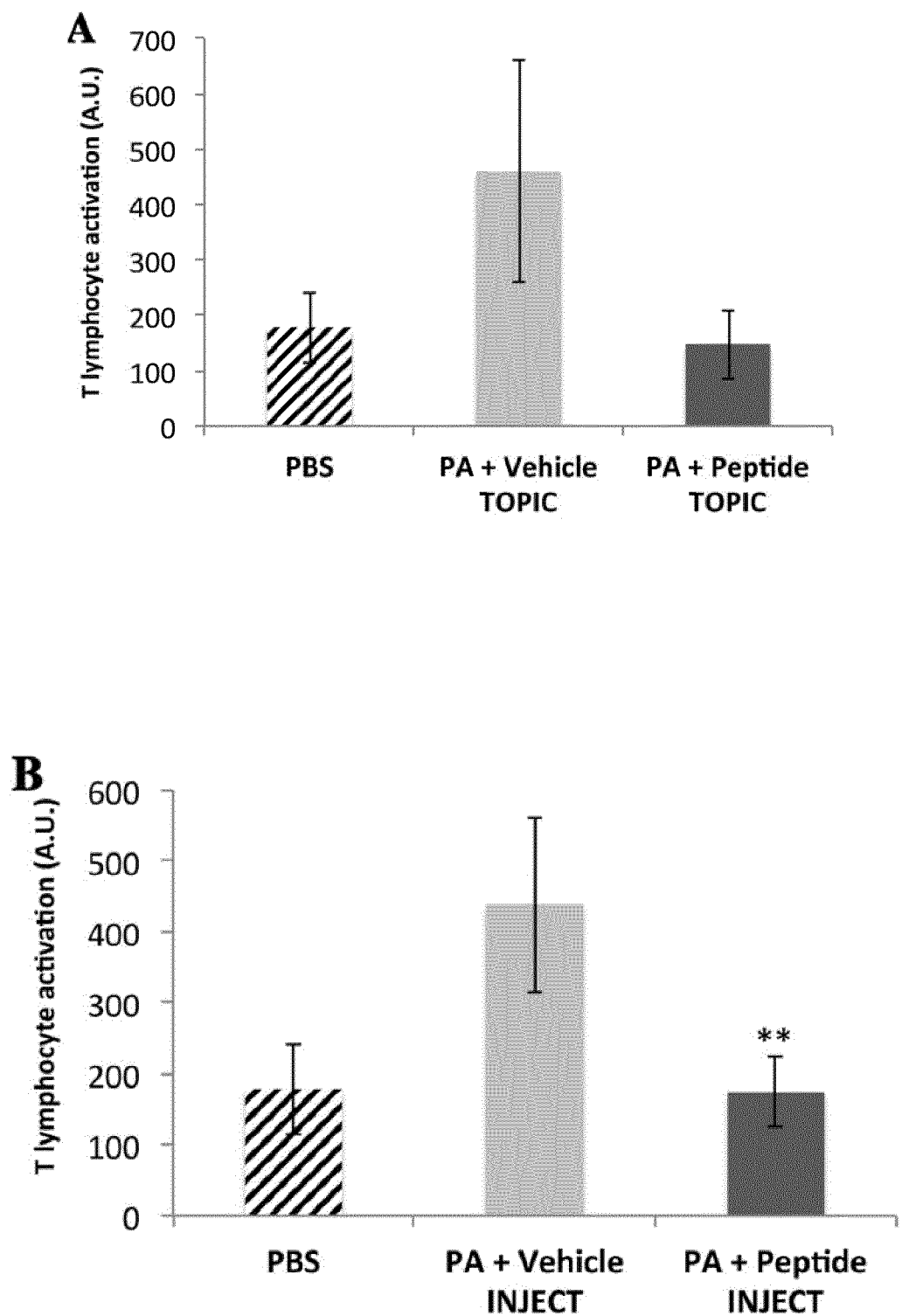

FIG. 28: Effects of intradermal injection and topical application of Fg1.1.1 peptide on *P. acnes*-induced lymphocyte activation in mice. (A) Ears of mice were intradermally injected with *P. acnes* ($OD_{620nm}$=1.0 corresponding to $2.10^7$ CFU/20 µl in PBS) to induce inflammation. Subsequently, 5% Fg1.1.1 peptide gel was applied on the ear skin surface of mice each day for 3 days (arrows). PA+Vehicle TOPIC corresponds to *P. acnes* injected in ears treated with vaseline alone. PA+Peptide TOPIC corresponds to *P. acnes* injected in ears treated with 5% Fg1.1.1 peptide mixed in vaseline. PBS corresponds to the non-treated group injected with PBS. (B) *P. acnes* strain (OD$_{620nm}$=1.5) was pre-treated for 1 h at 37° C. with Fg1.1.1 peptide (140 µM) (PA+Peptide INJECT) or with the vehicle (1% DMSO final in PBS) (PA+Vehicle INJECT) and then intradermally injected in ears of mice (approximately 2.0$^7$ CFU/20 µl) to induce inflammation. Control group was injected with PBS alone. At 96 h post infection, mice were euthanized and the ear ganglions were removed to test their ability to proliferate after 72 h growth in presence of anti-CD3 and anti-CD28 antibodies. Proliferation measurements were done with the Uptiblue reagent. Data are means±S.D. of eight individual experiments. Statistical significance is indicated by * (P< 0.05),  (P<0.01), * (P<0.001), and **** (P<0.0001), respectively.

Figure 29:
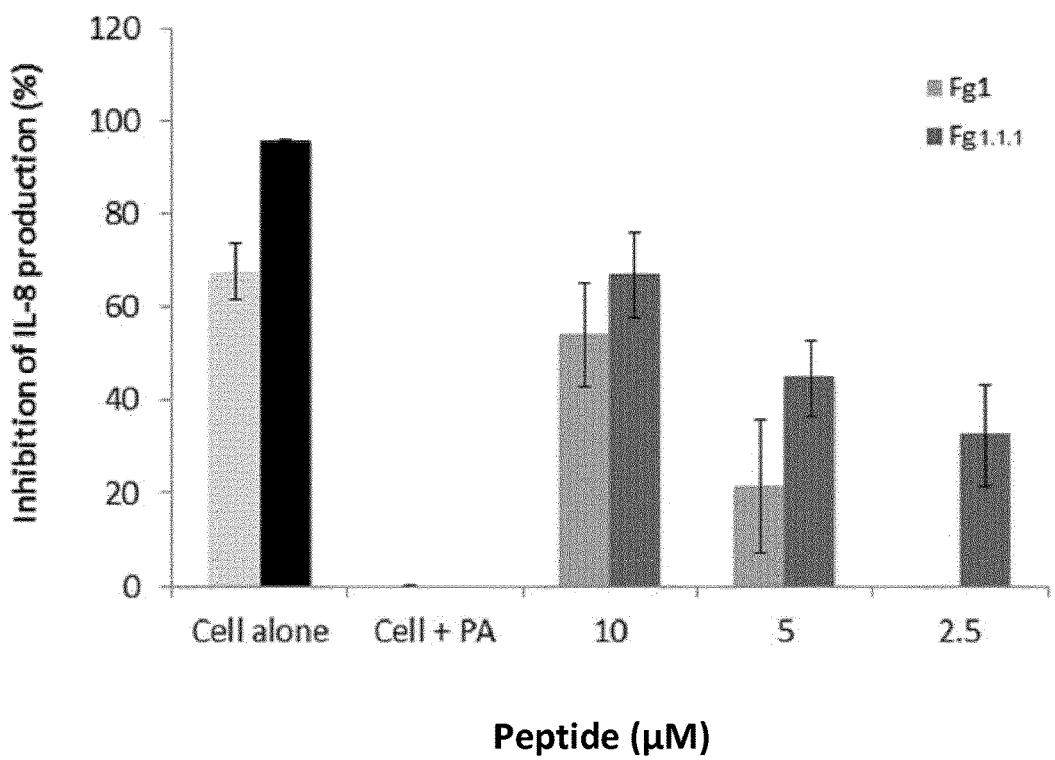

FIG. 29: Dose-dependent inhibition of IL-8 production by keratinocytes stimulated by *P. acnes* pre-treated with Fg1 or with Fg1.1.1 peptides. HaCaT cell were incubated for 24 h at 37° C. with *P. acnes* pre-treated for 1 h at 37° C. with the Fg1 peptide (light gray bar) and the Fg1.1.1 peptide (dark gray bar), at concentrations ranging from 2.5 to 10 µM. Controls experiments were done with unstimulated HaCaT cells (cell alone) and with HaCaT cell stimulated with non pre-treated *P. acnes* (Cell+PA). Measurement of IL-8 production was realized by ELISA as described in Materials and Methods. Data are means±S.D. of three separate experiments.

Figure 30:
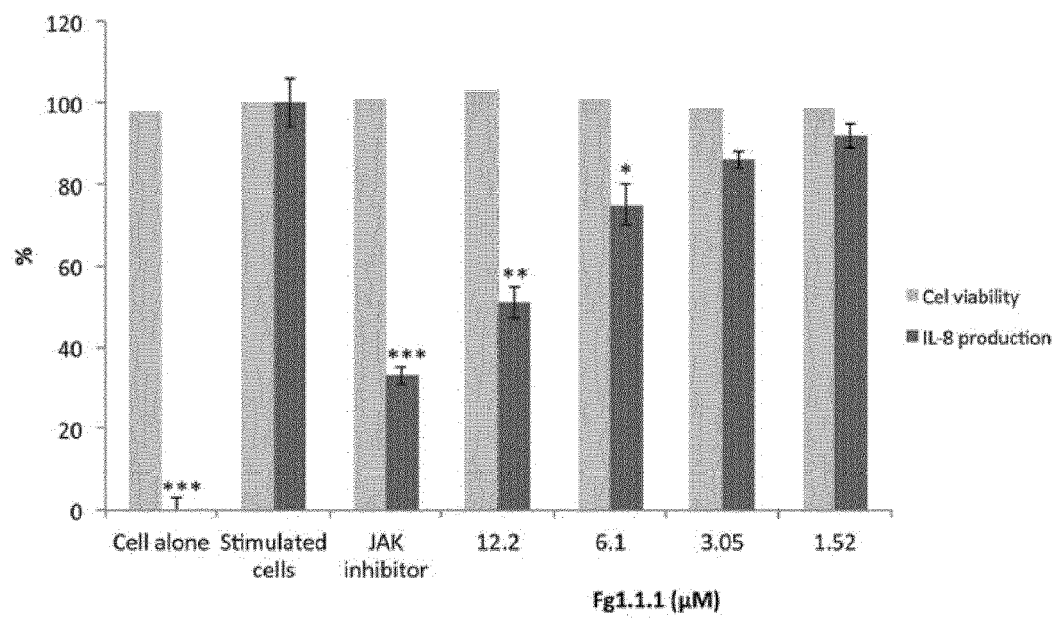

FIG. 30: Inhibition of Il-8 production by keratinocytes stimulated by Il-17, OSM and TNF-α. NHEK cells were stimulated by a combination of Il-17, OSM and TNF-α (3 ng/ml each) and treated with JAK inhibitor at 10 µM (positive control) or Fg1.1.1 at concentrations ranging from 1.52 to 12.2 µM for 48 h. Measurement of IL-8 production was realized by ELISA and cytotoxicity was determined by the MTT assay as described in Materials and Methods Control experiments were done with untreated and unstimulated NHEK cells (cell alone) and with untreated NHEK stimulated by the combination of Il-17, OSM and TNF-α. Data are means±S.D. of three individual experiments. Statistical significance is indicated by * (P<0.05),  (P<0.01), and * (P<0.001), respectively.

Figure 31:
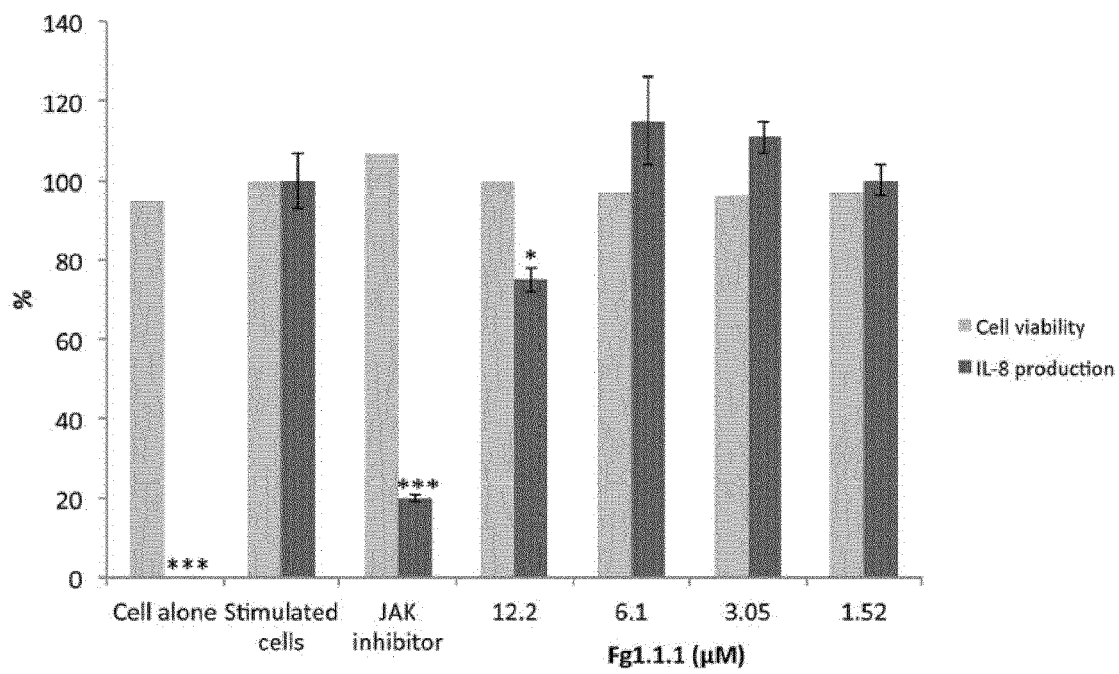

FIG. 31: Inhibition of hBD-2 production by keratinocytes stimulated by Il-17, OSM and TNF-α. NHEK cells were stimulated by a combination of Il-17, OSM and TNF-α (5 ng/ml each) and treated with JAK inhibitor at 10 µM (positive control) or Fg1.1.1 at concentrations ranging from 1.52 to 12.2 µM for 72 h. Measurement of hBD-2 production was realized by ELISA and cytotoxicity was determined by the MTT assay as described in Materials and Methods Control experiments were done with untreated and unstimulated NHEK cells (cell alone) and with untreated NHEK stimulated by the combination of Il-17, OSM and TNF-α. Data are means±S.D. of three individual experiments. Statistical significance is indicated by * (P<0.05),  (P<0.01), and * (P<0.001), respectively.

DETAILED DESCRIPTIONS

Definitions

Unless defined otherwise, all technical and scientific terms used herein have the same meaning as commonly understood by one of ordinary skill in the art to which this invention belongs.

In the present description the term "polypeptide" refers to a linear polymer of amino acids connected by peptide bonds. Proteins are large polypeptides, and the two terms are commonly used interchangeably.

In the present description the terms "nucleic acid", "nucleic sequence", "nucleic acid sequence", "polynucleotide", "oligonucleotide", "polynucleotide sequence" and "nucleotide sequence", used interchangeably, mean a precise sequence of nucleotides, modified or not, defining a fragment or a region of a nucleic acid, containing unnatural nucleotides or not, and being either a double-strand DNA, a single-strand DNA or transcription products of said DNAs.

It should also be included here that the present invention does not relate to nucleotide sequences or amino acid sequence in their natural chromosomal environment, i.e., in a natural state. The sequences of the present invention have been isolated and/or purified, i.e., they were sampled directly or indirectly, for example by a copy, their environment having been at least partially modified. Isolated nucleic acids or amino acid sequences obtained by recombinant genetics, by means, for example, of host cells, or obtained by chemical synthesis should also be mentioned here.

In the present description the term "bacterial strain" or "strain" means a subset of a bacterial species differing from other bacteria of the same species by some minor but identifiable difference. For example, according to the present invention, the *P. acnes* strains may be *P. acnes* 6919, RON and/or PIE strains.

In the present application the term "fragment" refers to a part of sequence, preferably amino acid sequence.

In the present description the term "fibrinogen" or "Fg" refers to a glycoprotein involved in the formation of blood clots, which is a hexamer, containing two sets of three different chains (Aα, Bβ, and γ), linked to each other by disulfide bonds. The N-terminal sections of these three chains contain the cysteine that participates in the cross-linking of the chains. The C-terminal parts of Aα, Bβ and γ chains contain a domain of about 225 amino-acid residues, which can function as a molecular recognition unit. This domain is implicated in protein-protein interactions.

In the present description the term "acne" or "acne vulgaris" refers to a common disorder having a multifactorial pathogenesis, including hormonal, immunological and microbiological mechanisms. This disease is localized to the pilosebaceous follicle that results in both inflammatory and noninflammatory clinical lesions. Most patients have a mixture of noninflammatory comedons and inflammatory papules, pustules and nodules. One of the major factors implicated in acne formation is the microbiological colonization of the sebaceous gland. Several lines of evidence have implicated an important role of *Propionibacterium acnes* (*P. acnes*) as the etiological agent in acne and orthopaedic infections (Antti-poika 1990).

Isolated Polypeptide for Therapeutic Use According to the Invention

For many pathogenic bacteria, the invasion of host cells is mediated by bacterial surface proteins or adhesins that recognize specific ligands. Skin-related bacteria, such as *Staphylococcus* and *Streptococcus*, express numerous cell surface adhesins called MSCRAMMs (microbial surface components recognizing adhesive matrix molecules) which specifically bind to host extracellular matrix components (ECM) to promote their adhesion to the target cells and subsequently to initiate colonization and infection (Patti 1994). Host ECM components represent ideal microbial adhesion targets that many pathogens use for colonization of tissues and the initiation of infection.

Thus, in the present invention, the inventors firstly investigated the interaction of *P. acnes* surface proteins with the ECM components. Using a direct binding assay, the inventors demonstrated for the first time that a 58-kDa glycoprotein is specifically recognized by human fibrinogen. This protein has been named Pfg. Endoglycosidase digestion study showed that the interaction between Pfg and fibrinogen involved the non-glycosylated part of human fibrinogen. Further experiences demonstrated that the N-terminal-part of fibrinogen is recognized by Pfg and is able to inhibit Pfg binding to fibrinogen.

This property of fibrinogen, particularly of its sub-unit Bß, to inhibit the adhesion of bacterial protein to their hosts may be used in therapy.

In one aspect, the present invention thus relates to an isolated polypeptide comprising an amino acid sequence with at least 80% identity with SEQ ID NO: 1 after optimal global alignment, or a fragment thereof comprising an amino acid sequence with at least 80% identity with anyone of SEQ ID NOs: 2, 5 and 7 to 13 and 47 after optimal global alignment, for use as a medicament.

SEQ ID NO: 1 corresponds to sub-unit Bß of human fibrinogen and SEQ ID NO: 2, 5 and 7 to 13 and 47 correspond to fragments of this sequence.

Chain Bß of fibrinogen is encoded by FGB gene, which is a gene found in humans and most other vertebrates with a similar system of blood coagulation. The amino acid sequence is about 450 amino acids long.

According to one embodiment, the polypeptide for therapeutic use of the invention comprises an amino acid sequence with at least 80%, at least 85%, preferably at least 90%, at least 95%, more preferably at least 96%, at least 97%, at least 98% or at least 99% identity with SEQ ID NO:1 after optimal global alignment, or an amino acid sequence with at least 80%, at least 85%, preferably at least 90%, at least 95%, more preferably at least 96%, at least 97%, at least 98% or at least 99% identity with SEQ ID NOs: 2, 5 and 7 to 13 and 47 after optimal global alignment.

In another embodiment the isolated polypeptide for therapeutic use according to the invention, is selected from SEQ ID NOs: 2, 5 and 7 to 13 and 47 or a polypeptide with at least at least 80%, at least 85%, preferably at least 90%, at least 95%, more preferably at least 96%, at least 97%, at least 98% or at least 99% identity with one of SEQ ID NOs: 2, 5 and 7 to 13 and 47 after optimal global alignment.

SEQ ID NO: 13 and SEQ ID NO: 47 correspond to the amino acid sequence of a particular fragment of Bß chain of human fibrinogen having 106 amino acids and named Fg1.

As used herein, the "percentage identity" between two sequences of nucleic acids or amino acids means the percentage of identical nucleotides or amino acid residues between the two sequences to be compared, obtained after optimal global alignment, this percentage being purely statistical and the differences between the two sequences being distributed randomly along their length. The comparison of two nucleic acid or amino acid sequences is traditionally carried out by comparing the sequences after having optimally aligned them in their entirety over their whole length, said comparison being made by any software well-known to those skilled in the art, such as needle software using «Gap open» parameter equal to 10.0, «Gap extend» parameter equal to 0.5 et a «Blosum 62» matrix. Needle software is for instance available from website ebi.ac.uk worldwide under denomination «Align».

The percentage identity between two nucleic acid or amino acid sequences is then determined by comparing the two globally and optimally-aligned sequences, in which the nucleic acid or amino acid sequences to compare can have substitutions, additions or deletions compared to the reference sequence for optimal global alignment between the two sequences. Percentage identity is calculated by determining the number of positions at which the amino acid or nucleotide is identical between the two sequences, dividing the number of identical positions by the total number of positions in the optimla global alignment, and multiplying the result by 100 to obtain the percentage identity between the two sequences. When using suitable software for optimal global alignment, such a needle software, the percentage identity between the two sequences to compare is calculated directly by the software.

For an amino acid sequence exhibiting at least 60% at least 70%, at least, 75%, at least 80%, preferably at least 85%, at least 90%, at least 95%, more preferably at least 96%, at least 97%, at least 98% or at least 99% identity with a reference amino acid sequence, preferred examples include those containing certain modifications in the reference sequence, notably deletion, addition or substitution of at least one amino acid, truncation or extension. In the case of substitution of one or more consecutive or non-consecutive amino acids, preferred substitutions are those in which the substituted amino acids are replaced by "equivalent" amino acids. Here, the expression "equivalent amino acid" is meant to indicate any amino acid likely to be substituted for one of the structural amino acids without however modifying the biological activities of the polypeptide of interest, and notably include the specific examples defined below.

Equivalent amino acids can be determined either on their structural homology with the amino acids for which they are substituted or based on the results of comparative tests of biological activity between the various antibodies likely to be generated.

As non-limiting examples, Table 1 below summarizes possible substitutions likely to be carried out without resulting in a significant modification of the biological activity of polypeptide of interest; inverse substitutions are naturally possible under the same conditions.

TABLE 1

| Original residue | Substitution(s) |
|---|---|
| Ala (A) | Val, Gly, Pro |
| Arg (R) | Lys, His |
| Asn (N) | Gln |
| Asp (D) | Glu |
| Cys (C) | Ser |
| Gln (Q) | Asn |
| Glu (G) | Asp |
| Gly (G) | Ala |
| His (H) | Arg |
| Ile (I) | Leu |
| Leu (L) | Ile, Val, Met |
| Lys (K) | Arg |
| Met (M) | Leu |
| Phe (F) | Tyr |
| Pro (P) | Ala |
| Ser (S) | Thr, Cys |
| Thr (T) | Ser |
| Trp (W) | Tyr |
| Tyr (Y) | Phe, Trp |
| Val (V) | Leu, Ala |

The polypeptides and fragments thereof as described above recognize *P. acnes* surface protein (Pfg) characterized by the inventors, bind to it, and inhibit adhesion of *P. acnes* to skin cells.

In the present invention, the inventors surprisingly identified a *P. acnes* surface protein (Pfg) of 58-kDa specifically recognized by human fibrinogen by using a biotinylated ligand binding assay. Pfg was further characterized by 2-D electrophoresis and MALDI-ToF analysis as a putative adhesion surface protein containing a LPXTG motif in its C-terminus. Pfg is mostly expressed during the stationary phase of culture and appears to be highly glycosylated containing GalNAc residues. Purified Pfg strongly recognize the Aα and Bβ subunits of Fg. Specific enzymatic deglycosylation of Fg showed that the protein backbone was involved in the recognition process.

The inventors also demonstrated that Bβ subunit of Fg and fragments thereof are able to inhibit the interaction of adhesion protein Pfg with its target ligand (Fg) or target cells (skin cells). Particularly, the polypeptides and fragments thereof as described above allow competing with this interaction, and thus participating in the prevention of bacterial adhesion to host cells.

Further to this capacity, the polypeptides and fragments thereof as described above may be used as drug, particularly for treating and/or preventing acne.

The inventors also found that the polypeptides and fragments thereof as described above have were general anti-inflammatory proprieties, indecently of the presence of *P. acnes*, and may thus be used as drug, particularly for treating and/or preventing other inflammatory skin diseases, preferably psoriasis.

As used herein "inflammatory skin diseases" are diseases coming in many forms, from occasional rashes accompanied by skin itching and redness, to chronic conditions such as dermatitis (eczema), rosacea, seborrheic dermatitis, and psoriasis. Skin inflammation can be characterized as acute or chronic. Acute inflammation can result from exposure to UV radiation (UVR), ionizing radiation, allergens, or to contact with chemical irritants (soaps, hair dyes, etc.). This type of inflammation is typically resolved within 1 to 2 weeks with little accompanying tissue destruction. In contrast, chronic inflammation results from a sustained immune cell mediated inflammatory response within the skin itself. This inflammation is long lasting and can cause significant and serious tissue destruction.

As used herein "psoriasis" means a common, chronic, relapsing/remitting, immune-mediated systemic disease characterized by skin lesions including red, scaly patches, papules, and plaques, which usually itch. The skin lesions seen in psoriasis may vary in severity from minor localized patches to complete body coverage. The five main types of psoriasis are plaque, guttate, inverse, pustular, and erythrodermic.

Specific Fragments of the Invention

Starting from the sequence of sub-unit Bβ of fibrinogen, the inventors identified specific fragments able to bind adhesion protein Pfg of *P. acnes* and thus to inhibit the adhesion of *P. acnes* to its target protein (fibrinogen) and to host skin cells.

In another aspect, the present invention thus relates to a fragment of a polypeptide comprising an amino acid sequence with at least 80% identity with of SEQ ID NO: 1 after optimal global alignment, said fragment comprising an amino acid sequence with at least 80% identity with anyone of SEQ ID NOs: 2, 5 and 7 to 13 and 47 after optimal global alignment.

To obtain these specific fragments, the sub-unit Bβ of human fibrinogen was divided into four segments having the same length (named Fg1, Fg2, Fg3 and Fg4) and were cloned and produced in bacterial vectors. The amino acid sequences of sub-unit Bβ of fibrinogen and of these fragments are shown in Table 2a below.

TABLE 2a

Amino acid sequences of sub-unit Bβ of fibrinogen and of fragments Fg1, Fq2, Fq3 and Fq4.

| Name of fragment | Amino acid sequence | SEQ ID NO: |
|---|---|---|
| Fibrinogen sub-unit Bβ | MKRMVSWSFH KLKTMKHLLL LLLCVFLVKS QGVNDNEEGF FSARGHRPLD KKREEAPSLR PAPPPISGGG YRARPAKAAA TQKKVERKAP DAGGCLHADP DLGVLCPTGC QLQEALLQQE RPIRNSVDEL NNNVEAVSQT SSSSFQYMYL LKDLWQKRQK QVKDNENVVN EYSSELEKHQ LYIDETVNSN IPTNLRVLRS ILENLRSKIQ KLESDVSAQM EYCRTPCTVS CNIPVVSGKE CEEIIRKGGE TSEMYLIQPD SSVKPYRVYC DMNTENGGWT VIQNRQDGSV DFGRKWDPYK QGFGNVATNT DGKNYCGLPG EYWLGNDKIS QLTRMGPTEL LIEMEDWKGD KVKAHYGGFT VQNEANKYQI SVNKYRGTAG NALMDGASQL MGENRTMTIH NGMFFSTYDR DNDGWLTSDPRKQCSKEDGG GWWYNRCHAA NPNGRYYWGG QYTWDMAKHG TDDGVVWMNW KGSWYSMRKM SMKIRPFFPQ Q | SEQ ID NO: 1 |
| Fg1 | MKRMVSWSFHKLKTMKHLLLLLLCVFLVKSQGVNDNEEGFFSARGHRPLDK KREEAPSLRPAPPPISGGGRARPAKAAATQKKVERKAPDAGGCLHADPDLGV LCMKRMVSWSFHKLKTMKHLLLLLLCVFLVKSQGVNDNEEGFFSARGHRPLDKK REEAPSLRPAPPPISGGGYRARPAKAAATQKKVERKAPDAGGCLHADPDLGVLC | SEQ ID NO: 13 |
| Fg1 | MKRMVSWSFHKLKTMKHLLLLLLCVFLVKSQGVNDNEEGFFSARGHRPLDKK REEAPSLRPAPPPISGGGYRARPAKAAATQKKVERKAPDAGGCLHADPDLGVLC | SEQ ID NO: 47 |
| Fg2 | DAGGCLHADP DLGVLCPTGC QLQEALLQQE RPIRNSVDEL NNNVEAVSQT SSSSFQYMYL LKDLWQKRQK QVKDNENVVN EYSSELEKHQ LYIDETVNSN IPTNLRVLRS ILENLRSKIQ KLESDVSAQM EYCRTPCTVS CNIPVVS | SEQ ID NO: 14 |
| Fg3 | KLESDVSAQM EYCRTPCTVS CNIPVVSGKE CEEIIRKGGE TSEMYLIQPD SSVKPYRVYC DMNTENGGWT VIQNRQDGSV DFGRKWDPYK QGFGNVATNT DGKNYCGLPG EYWLGNDKIS QLTRMGPTEL LIEMEDWKGD KVKAHYGGFT VQNE | SEQ ID NO: 15 |
| Fg4 | PTELLIEMED WKGDKVKAHY GGFTVQNEAN KYQISVNKYR GTAGNALMDG ASQLMGENRT MTIHNGMFFS TYDRDNDGWL TSDPRKQCSK EDGGGWWYNR CHAANPNGRY YWGGQYTWDM AKHGTDDGVV WMNWKGSWYS MRKMSMKIRP FFPQ | SEQ ID NO: 16 |

After testing, it appears that among the fragments Fg1, Fg2, Fg3 and Fg4 the active fragment is Fg1.

Moreover, the fragment Fg1 was firstly divided into three non-overlapping fragments (Fg1.1, Fg1.2 and Fg1.3, shown in table 2b) having approximately the same length (35, of 35 and 36 amino acids respectively) and after that each cutting area was surrounded by 15 amino acid allowing obtaining two other fragments (Fg1.4 and Fg1.5, shown in table 2b) having the same length of 30 amino acids and overlapping with the fragments Fg1.1, Fg1.2 and Fg1.3.

After testing, it appears that among the fragments Fg1.1, Fg1.2, Fg1.3, Fg1.4 and Fg1.5 the active fragment are Fg1.1 and Fg1.4.

The fragment Fg1.1 was further divided to six other fragments (Fg1.1.1, Fg1.1.2, Fg1.1.3, Fg1.1.4, Fg1.1.5 and Fg1.1.6, shown in Table 2b).

TABLE 2b

Amino acid sequences of fragments derived from Fq1 and Fq1.1.

| Name of fragments | Amino acid sequence | SEQ ID NO: |
|---|---|---|
| Fg1.1 | MKRMVSWSFHKLKTMKHLLLLLLCVFLVKSQGVND | SEQ ID NO: 2 |
| Fg1.2 | NEEGFFSARGHRPLDKKREEAPSLRPAPPPISGGG | SEQ ID NO: 3 |
| Fg1.3 | YRARPAKAAATQKKVERKAPDAGGCLHADPDLGVLC | SEQ ID NO: 4 |
| Fg1.4 | LLLCVFLVKSQGVNDNEEGFFSARGHRPLD | SEQ ID NO: 5 |
| Fg1.5 | APSLRPAPPPISGGGYRARPAKAAATQKKV | SEQ ID NO: 6 |
| Fg1.1.1 | LLLCVFLVKSQGVND | SEQ ID NO: 7 |
| Fg1.1.2 | LLLCV | SEQ ID NO: 8 |
| Fg1.1.3 | FLVKS | SEQ ID NO: 9 |
| Fg1.1.4 | QGVND | SEQ ID NO: 10 |
| Fg1.1.5 | LLLCVFLV | SEQ ID NO: 11 |
| Fg1.1.6 | KSQGVND | SEQ ID NO: 12 |

In order to adapt the fragment of the invention for more efficient use in therapy and enhancing its synthesis at minimal cost, the inventors provide fragments having reduced length.

Thus according to one embodiment of the invention, these fragments have a length of no more than 150, no more than 130, preferably no more than 110 amino acid or no more than 90 amino acids.

More preferably, the fragment of the invention has a length of 106 amino acid corresponding to SEQ ID NO: 13 and SEQ ID NO: 47 (fragment Fg1).

Even more preferably, the fragments of the inventions have a length comprised between 5 and 50 amino acids, preferably between 5 and 40, more preferably between 5 and 35. According to one embodiment, the fragments according to the invention may have a length comprised between 25 and 40 amino acids, preferably between 30 and 35 amino acids.

According to another embodiment, the fragments according to the invention may have a length comprised between 5 and 20 amino acids, preferably between 5 and 15 and more preferably between 5 and 10 amino acids.

Preferably, the fragments according to the invention have sequences corresponding to the SEQ ID NOs: 2, 5 and 7 to 12, more preferably SED ID NOs: 2 and 5

Isolated Nucleic Acids, Vectors and Host Cells According to the Invention

In another aspect, the present invention relates to an isolated nucleic acid molecule encoding the fragment according to the invention.

Nucleic acid sequences may also exhibit a percentage identity of at least 60% at least 70%, at least, 75%, at least 80%, preferably at least 85%, at least 90%, at least 95%, more preferably at least 96%, at least 97%, at least 98% or at least 99%, after optimal global alignment with a preferred sequence. It means that the nucleic sequences exhibit, with respect to the reference nucleic sequence, certain modifications such as, in particular, a deletion, a truncation, an extension, a chimeric fusion and/or a substitution, notably punctual. Preferably, these are sequences which code for the same amino acid sequence as the reference sequence, this being related to the degeneration of the genetic code, or complementarity sequences that are likely to hybridize specifically with the reference sequences, preferably under highly stringent conditions.

The invention also provides a vector comprising the nucleic acid molecule of the invention.

The term "vector", as used herein, is intended to refer to a nucleic acid molecule capable of transporting another nucleic acid to which it has been linked. One type of vector is a "plasmid" vector, which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e. g., bacterial vectors having a bacterial origin of replication and episomal mammalian vectors). Other vectors (e. g., non-episomal mammalian vectors) can be integrated into the genome of a host cell upon introduction into the host cell, and thereby are replicated along with the host genome.

The vector according to the invention preferably also contains elements necessary to allow delivery, propagation and/or expression of any of the nucleic acid molecule(s) described herein within a host cell or subject. In particular, in the vector according to the invention, the nucleic acid molecule according to the invention is preferably operably linked to appropriate regulatory sequences. As used herein, the term "regulatory elements" or "regulatory sequence" refers to any element that allows, contributes or modulates the expression of nucleic acid molecule(s) in a given host cell or subject, including replication, duplication, transcription, splicing, translation, stability and/or transport of the nucleic acid(s) or its derivative (i.e. mRNA). It will be appreciated by those skilled in the art that the choice of the regulatory sequences can depend on such factors as the vector itself, the host cell or subject, the level of expression desired, etc.

Representative examples of such suitable plasmid vectors, used in the invention, include, without limitation, pBSK vector, pET, pDEST, pRSET vectors in prokaryotes; pYES in yeast; pDEST, pcDNA in eukaryotes.

Moreover, the nucleic acid molecules of the invention and the vectors of the invention comprising these molecules can be used for the transformation of a suitable host cell. The term "host cell", as used herein, is intended to refer to a cell into which a recombinant expression vector has been introduced in order to express the polypeptides or fragments of the invention. It should be understood that such terms are intended to refer not only to the particular subject cell but also to the progeny of such a cell. Because certain modifications may occur in succeeding generations due to either mutation or environmental influences, such progeny may not, in fact, be identical to the parent cell, but are still included within the scope of the term "host cell" as used herein. Non-limitative examples of suitable host cells in the context of the present invention include bacterial cells, such as *E. coli* (notably strain DH5alpha), yeast cells (notably *Saccharomyces cerevisiae*), mammal cells (notably HeLa, CHO, 3T3 cell lines).

Transformation can be performed by any known method for introducing polynucleotides into a cell host. Such methods are well known of those skilled in the art and include dextran-mediated transformation, calcium phosphate precipitation, polybrene-mediated transfection, protoplast fusion, electroporation, encapsulation of the polynucleotide into liposomes, biolistic injection and direct microinjection of DNA into nuclei.

The host cell may be co-transfected with two or more nucleic acid molecules or expression vectors, including the vector expressing the polypeptide or fragment of the invention.

Pharmaceutical Composition, Drug and Combination Product

The inventors demonstrated that the fragments of the present invention, preferably the fragments having amino acid sequences corresponding to SEQ ID NO: 2, 5 and 7 to 13 and 47, recognize and bind Pfg adhesion protein of *P. acnes*, thus inhibiting *P. acnes* adhesion to its target ligand (fibrinogen) and to host skin cells.

In another aspect, the present invention thus relates to a pharmaceutical composition comprising at least one compound selected from the fragment, the isolated nucleic acid molecule, the vector or the host cell according to the present invention, and a pharmaceutically acceptable vehicle.

As used herein, "pharmaceutically acceptable vehicle" includes any and all solvents, buffers, salt solutions, dispersion media, coatings, antibacterial and antifungal agents, isotonic and absorption delaying agents, and the like that are physiologically compatible. The type of carrier can be selected based upon the intended route of administration. In various embodiments, the carrier is suitable for intravenous, intraperitoneal, subcutaneous, intramuscular, topical, transdermal or oral administration. Pharmaceutically acceptable carriers include sterile aqueous solutions or dispersions and sterile powders for the extemporaneous preparation of sterile injectable solutions or dispersion. The use of media and agents for pharmaceutically active substances is well known in the art. A typical pharmaceutical composition for intravenous infusion could be made up to contain 250 ml of sterile Ringer's solution, and 100 mg of the combination. Actual methods for preparing parenterally administrable compounds will be known or apparent to those skilled in the art and are described in more detail in for example, Remington's Pharmaceutical Science, 17th ed., Mack Publishing Company, Easton, Pa. (1985), and the 18th and 19th editions thereof The compound in the composition preferably is formulated in an effective amount. An "effective amount" refers to an amount effective, at dosages and for periods of time necessary, to achieve the desired result, such as prevention or treatment of inflammatory skin disorders, particularly acne. A "therapeutically effective amount" means an amount sufficient to influence the therapeutic course of a particular disease state. A therapeutically effective amount is also one in which any toxic or detrimental effects of the agent are outweighed by the therapeutically beneficial effects.

It is understood that the administration routes, dosing schedules and optimal galenic forms can be determined according to the criteria generally taken into account when establishing a treatment suited to a patient such as, for example, the patient's age, the seriousness of his general state, his tolerance for the treatment and the side effects experienced.

For instance, the fragment, the isolated nucleic acid molecule, the vector or the host cell according to the present invention may be present in the pharmaceutical composition according to the invention in the ranges from 0.1 to 10% weight/weight (w/w), preferably from 0.5 to 2% w/w, more preferably from 0.5 to 4% w/w, even more preferably from 2 to 6% w/w.

According to another aspect, the invention relates to the isolated nucleic acid molecule, the vector, the host cell or the pharmaceutical composition according to the invention, for use as a medicament.

In a preferred embodiment, the isolated nucleic acid molecule, the vector, the host cell or the pharmaceutical composition according to the invention are used in the treatment and/or the prevention of acne.

The inventors have also shown that the isolated nucleic acid molecule, the vector, the host cell or the pharmaceutical composition according to the invention, may be used in the treatment and/or the prevention of other inflammatory diseases, preferably psoriasis.

The fragment, the isolated nucleic acid molecule, the vector, the host cell or the pharmaceutical composition according to the invention, may be used alone or in combination with other anti-inflammatory agents in order to enhance their therapeutic effect.

In another aspect, the present invention thus also relates to a combination product comprising:
at least one compound selected from the fragment, the isolated nucleic acid molecule the vector and the host cell according to the invention; and
another pharmaceutical agent, preferably used for the treatment and/or the prevention of skin inflammatory diseases selected from psoriasis and/or acne, preferably acne;
for simultaneous, separate or sequential use as a medicament.

Such other pharmaceutical agents may be selected from the group consisting of doxycycline, isotretinoin, tretinoin, adapalene, benzoyl peroxide, clindamycin and erythromycin.

EXAMPLES

Materials and Methods
Bacterial Strains and Conditions of Growth

*P. acnes* strain 6919 was obtained from the American Type Culture Collection (Manassas, Va.) and *P. acnes* RON and PIE were isolated from patient with joint infection. All strains were grown under anaerobic conditions in reinforced clostridial liquid and solid medium (RCM) (Difco Laboratories, Detroit, Mich.). *P. acnes* was transferred from the bacterial stock onto RCM agar plate and incubated for 5 days under anaerobic condition by using a GasPak™ EZ Anaerobic Container System (Becton Dickinson & Co, Sparks Md., USA). A single colonie was transferred into 100 ml RCM and grown as described above. Bacterial suspension was then store frozen at −80° C. in presence of 10% glycerol final. This stock was called « start stock» and used for all the experiments. For routine culture, 100 ml of RCM or RCM supplemented with 0.1% tween 80 (RCM+T80) were used and bacteria were harvested after 5 days at 37° C. by centrifugation at 7,000×g for 10 min at 4° C. Pellets were pooled and washed in about 30 ml of cold PBS and centrifuged again as described above. Finally, the bacterial pellet was suspended in PBS [1.5 mM $KH_2PO_4$, 2.7 mM $Na_2HPO_4.7H_2O$, 0.15 M NaCl (pH 7.4)] (1:10 from volume culture). Bacteria were also grown onto Columbia agar complemented with 5% sheep blood for 5-8 days at 37° C. under anaerobic conditions as described above. Bacteria were scrapped in PBS (3 ml of PBS per Petri dish) and used for surface protein extraction. For large quantity of culture, 200 ml of *P. acnes* 5 days-old RCM culture were used as inoculum for 2 liters of RCM previously equilibrated at 37° C. To ensure the anaerobic condition, the culture was extensively flushed with $N_2$ for 10 min and sealed. Every 2 h, 10 ml of culture were harvested to measure the absorbance at 600 nm and the pH, and the culture was flush with $N_2$ as described above. Bacteria were centrifuged at 7,000×g for 10 min and the pellet was resuspended in PBS. The total surface protein extract was obtained as described below.

Total Surface Protein Extraction

Surface proteins were heat extracted in PBS alone or in presence of 2% SDS at 60° C. for 20 min or in presence of 1% LiCl at 45° C. for 2 h (Shen 1993). Bacteria were removed by centrifugation at 16,000×g for 20 min at 4° C. Excess of SDS and LiCl were removed under dialysis against PBS. The resulting solution was called *P. acnes* heat extract (PANE) and subjected to ammonium sulfate precipitation at 80% of saturation for 1 h under stirring at 4° C. for concentration. Precipitated proteins were recovered after centrifugation at 22,000×g for 30 min at 4° C., then resuspended in PBS, and extensively dialyzed against PBS. This protein solution was called concentrated *P. acnes* heat extract (cPAHE). Protein concentration was determined by the method of Lowry using BSA as standard described by Peterson (Peterson 1983).

Biotinylation cPAHE, purified Pfg and commercial ECM ligands were adjusted to the concentration of 1 to 10 mg/ml in PBS and dialyzed against [74 mM sodium tetraborate, 60 mM boric acid (pH 8.8)] overnight at 4° C. Whole *P. acnes* bacteria were recovered in PBS as described above and the pellet was resuspended in the borate buffer. This operation was repeated twice. Proteins and whole bacteria were incubated using the extrinsic labeling reagent sulfo-N-hydroxysuccinimide (NHS)-biotin (Sigma) at ratio of 250 µg of NHS-biotin for 1 mg of protein for 4 h at 4° C. under end-over-end stirring. The reaction was stopped by adding 1 M $NH_4Cl$. Excess of biotin-NHS was removed by dialysis against PBS at 4° C. for proteins solutions and by centrifugation for whole bacteria. Biotinylated proteins preparations were stored at −80° C., and biotinylated bacteria were stored at +4° C. before use. Preparation of biotinylated bacteria were used no more than 5 days after preparations.

Binding Activity.

To characterize the interaction between *P. acnes* and ligands, we used biotinylated molecules in quantitative and qualitative assays. In a first set of assays, ECM ligands (fibrinogen, collagens I, IV, VI and VIII) were used as labelled proteins with biotin. In a second set of assays, *P. acnes* surface proteins (total extract and purified Pfg) were biotinylated. For quantitative analysis, unlabeled protein were diluted into 50 mM carbonate-bicarbonate, pH 9.6 buffer to yield a protein concentration ranging from 0.01 to 50 µg/ml, and then immobilized to 96-well polystyrene plates at 4° C. overnight. The wells were rinsed three times with 0.2 ml of PBS containing 0.05% Tween-20 (PBS-Tween). Biotinylated proteins (0.01 to 16 µg/ml in PBS-Tween) were added to the wells and incubated at room temperature for 1 h. The wells were rinsed three times with 0.2 ml of PBS-Tween. Peroxidase conjugated to streptavidin (0.5 µg/ml in PBS-Tween) was added and incubated for 30 min at room temperature. After washing, bound peroxidase was detected using the chromogenic peroxidase substrate ABTS. For qualitative analysis, unlabelled protein (10-75 µg per lane) were separated by SDS-PAGE and then transferred to nitrocellulose membranes (0.45 µm pore size), as described previously (Towbin, 1979). Membranes were then saturated overnight at 4° C. in PBS containing 5% BSA, 0.05% Tween-20 (PBT buffer). Binding activity was detected by incubating the membranes with 20 ml of PBT containing biotinylated proteins (0.1 µg/ml) for 2 h at room temperature followed by three washes with PBT. Bound biotinylated proteins were detected by incubating the membrane with peroxidase conjugated to streptavidin (0.5 µg/ml in PBT) for 1 h at room temperature. After washing, bound peroxidase activity was detected using 3,3'-diaminobenzidine in the presence of $CoCl_2$ and $H_2O_2$ (Harlow and Lane, 1988).

Two-Dimensional Electrophoresis

An 13-cm pH 10-3 immobilized pH gradient (IPG strip) (Amersham-Bioscience, Sweden) was rehydrated at 20° C. for 13 h with 250 µl of IEF solution (8 M urea-2% CHAPS (wt/vol)-0.5% IPG buffer pH 4-7 (vol/vol)-0.002% bromophenol blue) that contained 200 µg of proteins from cPAHE. Isoelectric focusing was conducted at 20° C. in four steps, 1 h at 200 V, 1 h at 500 V, 30 min at 8000 V in a gradient mode, and 3 h at 8000 V using the Ettan IPGphor system (Amersham-Pharmacia, Sweden). For the second dimension, the IPG strip was equilibrated for 15 min by rocking in a solution of 6 M urea-30% glycerol (wt/vol)-0.05 M Tris-HCl-2% SDS (wt/vol)-0.002% bromophenol blue-100 mM DTT and for 15 min in a solution of 6 M urea-30% glycerol (wt/vol)-0.05 M Tris-HCl-2% SDS (wt/vol)-0.002% bromophenol blue-400 mM iodoacetamide. The IPG strip was then apply onto a 12% SDS-PAGE gel. Typically 2 gels were run in parallel for 6 h at 70 mA current constant. Proteins were detected into one gel by silver staining without the glutaraldehyde step. The spot of interest was visualized using the BOA as described previously. The silver stained gels and the membranes were matched and the spots of interest were excised from the gel.

Peptide Mass Fingerprinting by Matrix-Assisted Laser Desorption Ionization (MALDI)-Time-of-Flight (ToF) Mass Spectrometry In-gel tryptic digestion of two-dimensional protein spots was carried out in 25 mM ammonium bicarbonate buffer (pH 8.0) containing 50% (vol/vol) acetonitrile prior to vacuum drying (Jonsson 2001). Rehydration was done with 50 mM ammonium bicarbonate buffer (pH 8.0) containing 0.02 g/l of sequencing-grade modified porcine trypsin (Promega, Madison, Wis.) and digestion was performed for 18 h at 37° C. and stopped by adding of 0.4% (vol/vol) trifluoroaceic acid. The recovered peptide solution was spotted on the matrix film and allowed to dry at room temperature. Sample deposits were rinsed with pure water and subsequently inserted in the MALDI mass spectrophotometer (Applied Biosystems, Voyager DE super STR) equipped with a 337-nm $N_2$ laser. Fast evaporation matrix films were produced as previously described (Vorm, 1994) by using a saturated solution of 4-hydroxy-α-cyanocinnamic acid (Sigma) in acetone. Internal mass calibration of all spectra was accomplished by using the porcine trypsin auto-digestion peptide. Peptide masses were searched against the SWISS-PROT and Genpept databases.

Pfg Purification cPAHE (90 mg in 16 ml) were centrifuged at 5,000×g for 10 min at room temperature to remove unsolubilized material and fractionated by anion-exchange chromatography performed onto a UNOsphere Q anion exchange column (2.5 by 10 cm) (BioRad) equilibrated in the buffer A [25 mM Tris (pH 8.0)] at a flow rate of 24 ml/h. Unbound proteins were washed with buffer A (24 ml), and bound proteins were eluted stepwise with 0 to 160 (28 ml), 160 to 200 mM (40 ml) with buffer A+2 M NaCl. The fractions (1.5 ml) containing Fg-binding activity were pooled, desalted by extensive dialysis at 4° C. against the buffer 0.1 M $NH_4HCO_3$, pH 8.0 and lyophilized. Final purification of Pfg was achieved by loading 3 mg of protein in a volume of 5 ml onto a Sephacryl S-300 HR column (1 by 120 cm) (GE Healthcare) equilibrated with 0.1 M $NH_4HCO_3$, pH 8.0 at a flow rate of 6 ml/h (1.5 ml/fraction) over a period of 24 h. The fractions (1.5 ml) containing Fg-binding activity were pooled and store at −20° C.

Fibrinogen Deglycosylation

To assess which part of the fibrinogen is recognized by P. acnes surface proteins, the glycanic part in order to preserve the integrity of the protein backbone has been removed enzymatically. Since it has been shown that the fibrinogen is a glycoprotein containing both, N- and O-linked glycans (Debeire 1985; Reid Townsend 1982; L'Hôte 1996), endoglycosidases, N-glycanase and O-glycanase for removing glycans were used. All the enzymes and reagent used were purchased from ProZyme (Prozyme, San Leandro, Calif.). Purified commercial human and bovine Fg (100 µg; Sigma) were denatured at 100° C. for 5 min the buffer containing [0.4% SDS, 200 mM β-mercaptoethanol, 50 mM sodium phosphate (pH 7.0)], cooled at room temperature and then 3% NP-40 was added. For removing N-linked glycans, 0.5 U of *Flavobacterium meningosepticum* recombinant in *Escherichia coli* PNGase F (N-Glycanase) were added and incubated for 24 h at 37° C., final volume 50 µl. For removing O-linked glycans, denaturated human fibrinogen was first incubated in presence of 0.25 U of *Vibrio cholerae* sialidase A, bovine testes ß-galactosidase, and jack bean meal β-N-acety-glucosaminidase for 3 h at 37° C. since monosaccharides must be removed until only the Galβ(1-3)GalNAc core remains attached to the protein. Then, 0.5 U of *Streptococcus pneumoniae* recombinant in *Escherichia coli* Endo-α-N-acety-galactosaminidase (O-glycanase) was added and incubated for 24 h at 37° C. Enzymatic reactions were stopped by mixing the sample with the electrophoresis sample buffer, followed by a denaturation at 100° C. for 3 min. N- and O-deglycosylated Fg were then tested for their ability to bind biotinylated Pfg using the binding assay described above. Deglycosylation reaction was monitored the mobility shifts of the fibrinogens before and after deglycosylation on SDS-PAGE after Coomassie blue-staining. Monitoring was also achieved by using RCA-I and jacalin plant lectins as described below.

Plasmid Constructions

Fragments of Bß-subunit of human fibrinogen were obtained by RT-PCR from total RNA extracted from human hepatoma cell line Hep-G2 cultured in modified Dulbecco's medium supplemented with 10% fetal calf serum. Briefly, Total RNA was isolated with TRIzol reagent (Invitrogen Ltd, Paisley, UK) according to the manufacturer's instructions and treated with DNAse I (Roche Molecular Biochemical). RNA concentration was determined by the $A_{260}$ value of the sample. Complementary DNA was generated from 2 µg total RNA using the oligo(dT) primer and 200 U of SuperScript™ II Reverse Transcriptase (Invitrogen Ltd., Paisley, UK) and then used as template for standard PCR reaction. Standard amplification was carried out using 0.5 U the high fidelity Platinum® Pfx DNA polymerase (Invitrogen Ltd., Paisley, UK) in 25 µl final volume with the cycling conditions set at 94° C. for 15 s, 50° C. for 30 s and 68° C. for 45 s for a total of 35 cycles. Primers amplified a 318, 441, 462 and 462 bp fragments of fibrinogen cDNA.

The specific pairs of primers were used as follow:

```
GCAGGAATTCTGATGAAAAGGATGGTTTCTTGG   (SEQ ID NO: 17)
and
GGCCGCTCGAGTACACAACACCCCCAGGTCTGG   (SEQ ID NO: 18)
for Fg1;

GCAGGAATTCTGGATGCTGGAGGCTGTCTTCAC   (SEQ ID NO: 19)
and
GGCCGCTCGACTAGACACCACAGGAATATTGCA   (SEQ ID NO: 20)
for Fg2;

GCAGGAATTCTGAAGTTAGAATCTGATGTCTCA   (SEQ ID NO: 21)
and
GGCCGCTCGAGTTTCATTCTGTACAGTGAATCC   (SEQ ID NO: 22)
for Fg3;

GCAGGAATTCTGCCCACAGAACTTTTGATAGAA   (SEQ ID NO: 23)
and
GGCCGCTCGAGTCTGTGGGAAGAAGGGCCTGAT   (SEQ ID NO: 24)
for Fg4.
```

Restrictions sites of EcoRI and XhoI were added to the sense- and antisense primers, respectively. Fibrinogen PCR fragments were purified and first inserted in the pBSK vector. After digestion of the fragments with EcoRI/XhoI, the fragments were inserted into pGEX-4T-2 digested with EcoRI and XhoI.

Expression and Purification of the GST-Fusion Proteins

The *E. coli* BL21DE3pLys strain was used to produce the different GST-Fibrinogen-fragment fusion proteins. Bacteria were grown over night in LB medium (10 ml) supplemented with 100 µg/ml of Ampicillin and 40 µg/ml of Chloramphenicol and were utilized to inoculate 1 l of LB medium. When the culture incubated at 30° C. reached an $OD_{650}$=0.7, the protein expression was induced by adding 0.5 mM Isopropyl α-D-thiogalactoside (IPTG) and the culture was extended for another 4 h. The culture was harvested by centrifugation at 5000×g for 10 min. The pellet was washed once in PBS and resuspended in a Lysis buffer TEN-T (20 mM TrisHCl pH:7.5, EDTA 0.5 mM, NaCl 150 mM, Triton X-100 1%) sonicated 30 sec by bursts over ice, and supplemented with DTT 2 mM, N-Lauryl Sarcosine 1.5%. The lysate was centrifuged 20 min at 20000×g and the supernatant discarded. The insoluble pellet fraction containing the GST-fusion protein was dissolved in TEN-T buffer+8 M Urea and the solution clarified by centrifugation 20 min at 20,000×g. Solubilized protein was loaded onto the Protino GST/4B column (MachereyEtNagel) and eluted using the buffer 50 mM Tris, 10 mM glutathione, pH 8.0. Fractions containing recombinant peptide (determined by sodium dodecyl sulfate-polyacrylamide gel electrophoresis) were pooled. In a final step, just before utilization, the supernatant was dialyzed against PBS to remove urea.

Cell Culture and Stimulation

The immortalized human keratinocyte cell line HaCaT, fibroblast MRC5 were grown in Dulbecco's modified Eagle's medium-Glutamax-I (DMEM) with 1 mM sodium pyruvate. The immortalized human monocytic cell line ThP1 was grown in Roswell Park Memorial Institute 1640 Medium-Glutamax-I (RPMI). DMEM and RPMI were supplemented with 0.1% and 10% heat-inactivated fetal calf serum (Invitrogen), and antibiotic/antimycotic solution (10 U/ml Pencillin, 10 µg/ml Streptomycin, 0.25 µg/ml Amphoterin) at 37° C. in humidified atmosphere containing 5% $CO_2$ as described (Life Technologie). Primary human keratinocytes (NHDK) and fibroblast (HDF) were grown in the KGM-Gold and in FGM-2 Bullet Kit as described by the manufacturer, respectively (Lonza). The immortalized cell lines were routinely tested to assess the absence of *Mycoplasma* infection.

For experiences of stimulation with *P. acnes*, cells were incubated with the *P. acnes* suspension adjusted at the appropriate concentration, pre-treated for 1 h at 37° C. or not with fibrinogen recombinant peptides Fg1 and Fg2 at the concentrations 0.87, 1.75, 3.5 or 7 µM for the desired period of time at 37° C. in 5% $CO_2$.

For experiences of stimulation with LTA (lipoteichoic acid), PGN (peptidoglycanne) or LPS (lipopolysaccharides), cells were pre-treated or not with fibrinogen recombinant peptides Fg1 and Fg2 at the concentrations 7, 3.5 or 1.75 µM for 24 h at 37° C. in 5% $CO_2$ and then stimulated with LTA or PGN or LPS at the final concentration of 10 µg/ml for 18 h at 37° C.

For experiences using an in vitro model of psoriasis, cutaneous primary human keratinocytes (NHDK) were grown in culture medium for 24 hours. Cells were then treated or not (negative control) by peptide Fg1.1.1 at the concentrations of 1.52, 3.05, 6.1 and 12.2 µM or the reference (JAK Inhibitor I at 10 µM; positive control) and pre-incubated for 2 or 24 hours. Following this pre-incubation, the medium was removed and replaced with culture medium containing or not Fg1.1.1 at the concentrations of 1.52, 3.05, 6.1 and 12.2 µM or the JAK inhibitor at the concentration of 10 µM and pro-inflammatory mixture (combination of IL-17+OSM+TNF-α, each 3 or 5 ng/ml) and the cells were incubated for 48 or 72 hours.

Adhesion Assay

The bacterial suspension was adjusted at 600 nm to the desired concentration, pretreated with peptides Fg1 and Fg2 at the final concentration ranging from 0.87 to 7 µM for 1 h at 37° C. and deposited on the previously saturated cells with a solution of PBS SVF 2% for 2 h. After incubation for 1 h at 37° C., unbound bacteria are removed by 3 washes with PBS and fixed bacteria are detected by a streptavidin-peroxidase solution of 0.5 µg/ml for 30 min. After 3 washes, the detected bacteria are revealed by the substrate ABTS (2,2'-azinobis [3-ethylbenzthiazoline-6-sulfonic acid]-diammonium salt) for 30 min and read at 410 nm.

Measurement of ROS Production by Spectrofluorimetric Analysis

All cells lines ($5 \cdot 10^4$ to $10^5$ cells/well) were seeded in 96-well plates (Corning Costar, Brumath, France) and treated as previously described. After stimulation, cells were washed three times in PBS and incubated with 100 µl per wells of 5 µM DHE (for determination of $O_2^{\bullet-}$) or 5 µM $H_2$-DCFDA (for determination of $H_2O_2$) for 30 min as described previously and fluorescence intensity was recorded every hour over a period of 5 h. Fluorescence excitation/emission maxima were for DHE: 480/610 nm and for $H_2$-DCFDA: 507/525 nm. At the end of the experiment, the number of adherent cells was evaluated by the crystal violet assay as described below. $O_2^{\bullet-}$, and $H_2O_2$ were assayed by spectrofluorimetry on a Fusion spectrofluorimeter (PackardBell, Paris, France). Levels of ROS were calculated in each sample as follows: reactive oxygen species rate (arbitrary units/min/$10^6$ cells)=(fluorescence intensity [arbitrary units] at T5h—fluorescence intensity [arbitrary units] at To/300 minutes/number of adherent cells as measured by the crystal violet assay, and were expressed as arbitrary unit (A.U.).

Cell Viability Assays

Crystal violet staining was used to determine the number of adherent cells in 96-well plates. Briefly, after incubation with the test compound, the culture medium was discarded and the cells were incubated with a 0.05% crystal violet solution (Sigma) for 30 min at room temperature. After washing with PBS, 100% methanol was added, and the absorbance was measured spectrophotometrically at 540 nm on an ELISA multiwell reader. The MTT (1-(4,5-dimethylthiazol-2-yl)-3,5-diphenylformazan) assay was performed to test cell viability in 96-well plates. The cells were incubated with a 0.2% MTT solution in cell culture medium for 4 h at 37° C. The MTT solution was then discarded and DMSO added to solubilize the MTT-formazan crystals produced in living cells. After thorough mixing, the absorbance was measured at 540 nm.

ELISA

Human IL-1ß, IL-8, IL-12, hBD-2, and TNF-α protein concentration was measured in the supernatants of stimulated cells using various ELISA Set kits (Ready-Set-Go kit from eBioscience for acne experiments, and for psoriasis experiments the Duo set IL-8 kit from R&D Systems and the BD-2 Human Development (hBD-2) from Peprotech) according to the manufacturer's instructions. We used serial dilutions of recombinant human IL-1ß, IL-8, IL-12 and TNF-α for standard curve. The optical density was determined at 450 nm at a wavelength correction of 540 nm.

Statistical Analysis

The statistical significance of differences between data from experimental groups was analyzed by paired Student's-test. A level of P 0.05 was accepted as significant. Statistical significance is indicated by * (P 0.05),  (P 0.01), and * (P 0.001), respectively.

Results

Identification of *P. acnes* Cell Surface Proteins with Eukaryotic Ligands

Figure 1:
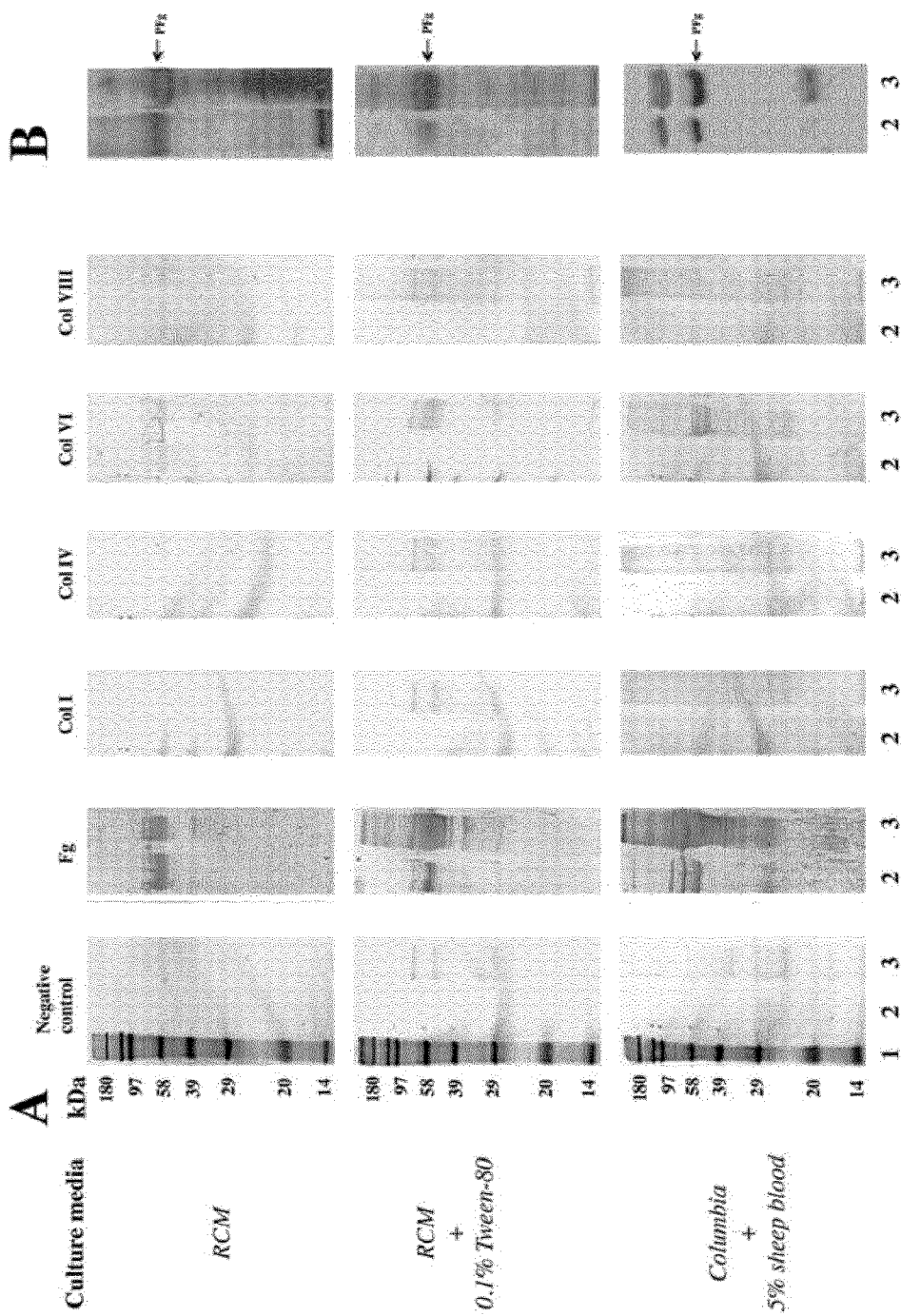
FIG. 1: Identification of a 58-kDa P. acnes surface protein recognized by fibrinogen. P. acnes 6919 strain was grown at 37° C. under anaerobic conditions on RCM, RCM supplemented with 0.1% Tween-80 and columbia supplemented with 5% sheep blood. (A) P. acnes surface proteins (75 µg) were heat extracted at 60° C. in PBS (lane 2) and at 45° C. in 1M LiCl (lane 3), and separated onto 12.5% SDS-PAGE, transferred onto nitrocellulose membrane and incubated with biotinylated fibrinogen, collagens I, IV, VI and VIII (0.1 µg/ml) for 2 h at room temperature. Control experiments were done by using HRP-streptavidine alone. Lanes 1: Molecular weight standards.
Figure 2A:
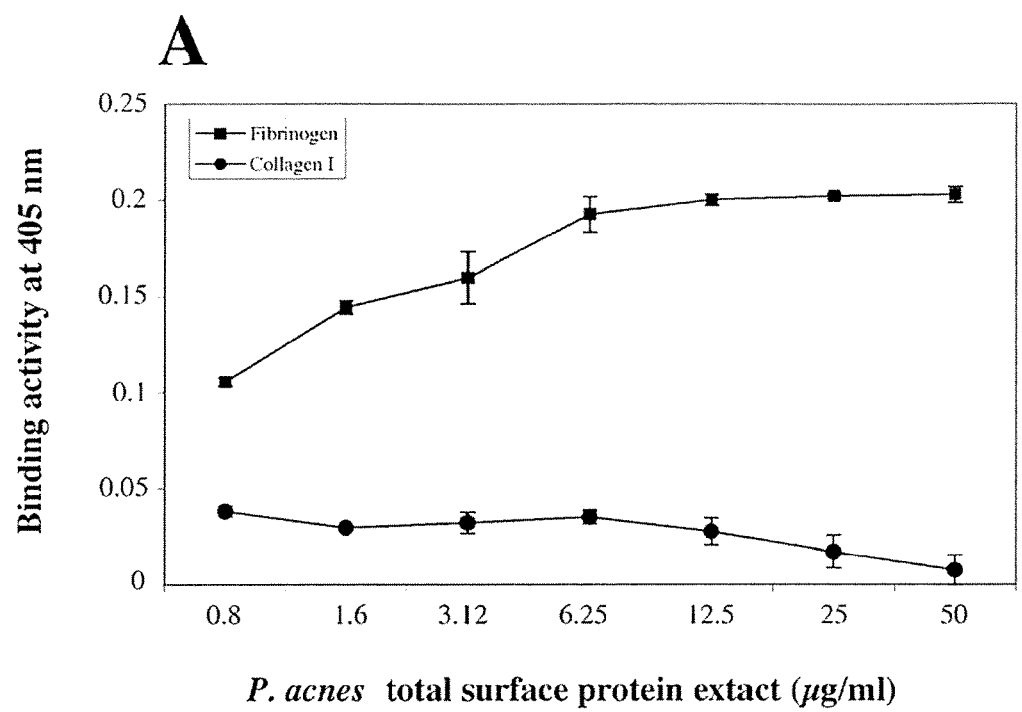
FIG. 2: Binding of P. acnes surface protein to purified human fibrinogen. (A) P. acnes surface proteins (0.8 to 50 µg/ml) were immobilized onto a 96-well polystyrene plate and probed with biotinylated fibrinogen (0.1 µg/ml) for 2 h at room temperature. (B) P. acnes surface proteins (25 µg/ml) were immobilized onto a 96-well polystyrene plate and probed with various concentrations of biotinylated fibrinogen ranging from 0.1 to 16 µg/ml for 2 h at room temperature. Bound biotinylated fibrinogen were detected with HRP-streptavidine as described in Materials and Methods.
Figure 2B:
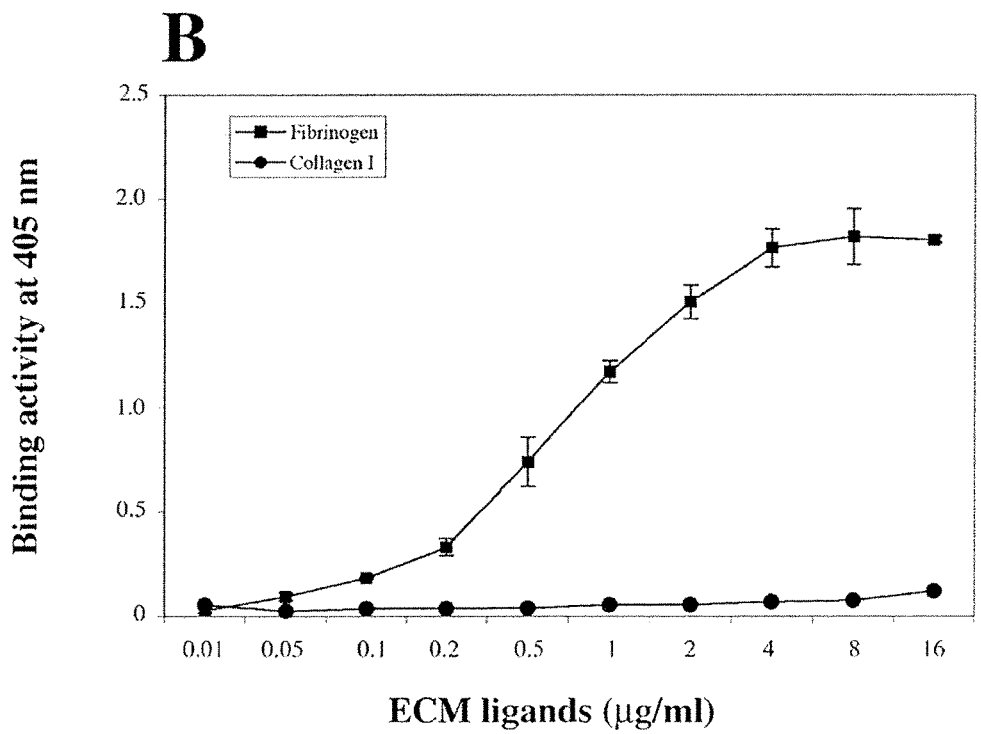

In order to identify *P. acnes* surface protein recognized by ECM ligands, we used the most commons ECM proteins recognize by skin related bacteria like collagens and fibrinogen. *P. acnes* strain was grown onto three different media in order to allow the bacteria to express its putative surface proteins which were extracted by heating the bacterial suspension in presence or not of lithium chloride. To identify surface proteins, *P. acnes* total heat protein extracts were electrophoretically separated and detected by silver staining (FIG. 1B). Several bands ranging from 14 to 100 kDa were detected with one protein of an apparent molecular mass of 58-kDa representing approximately >90% of the total protein extract (FIG. 1B, lane 2). No major differences were found between the RCM and RCM 0.1% Tween 20 media, however more proteins appears to be extracted in presence of lithium rather than the heat extraction alone. When *P. acnes* is grown on to solid media enriched with blood, the 58-kDa is present in both extracts with also a protein band at about 90-kDa and another one at about 20-kDa only present in the lithium heat extract (FIG. 1B, lane 3). Putative *P. acnes* surface adhesin were subsequently identified by Western blotting with biotinylated ligands (FIG. 1A). We found that the 58-kDa protein was recognized by biotinylated fibrinogen (FIG. 1A, lane 2) in both, heat extract and lithium heat extract, independently of the growing media used. No recognition was found with collagens (FIG. 1, lane 2). Very faint and non-reproductive recognition were obtained with the collagens VI and were not considered as specific. It is interesting to note that the intensity of recognition is higher in the lithium extract suggesting a better recovery with this method. Also, growing *P. acnes* on different media did not affect dramatically the expression of surface proteins recognized. According to these results, *P. acnes* was grown on RCM media and to heat extract surface proteins in presence of lithium. To confirm these results, *P. acnes* total surface protein were immobilized onto polystyrene plate and probed with biotinylated Fg and Collagen I (FIG. 2). Firstly several concentrations of protein extract were tested and were shown a binding activity for fibrinogen reaching a plateau at about 6.25 µg/ml protein per well, while no binding activity was detected for collagen I. To verify this result, 25 µg/ml of protein were immobilized per well and tested with various quantity of biotinylated Fg and Collagen I (FIG. 2B). It has been shown a strong binding activity with the fibrinogen, reaching a plateau, suggesting a possible saturation of recognized sites. No binding activity was detected with collagen I indicating a specific interaction between fibrinogen and the *P. acnes* protein extract. These results are in accordance with the qualitative results display previously. The 58-kDa protein has not yet been described therefore it was further proceed with its characterization. Because 58-kDa is a fibrinogen binding protein extracted from the surface of *P. acnes* it was named as PFg.

Characterization of Pfg

Figure 3:
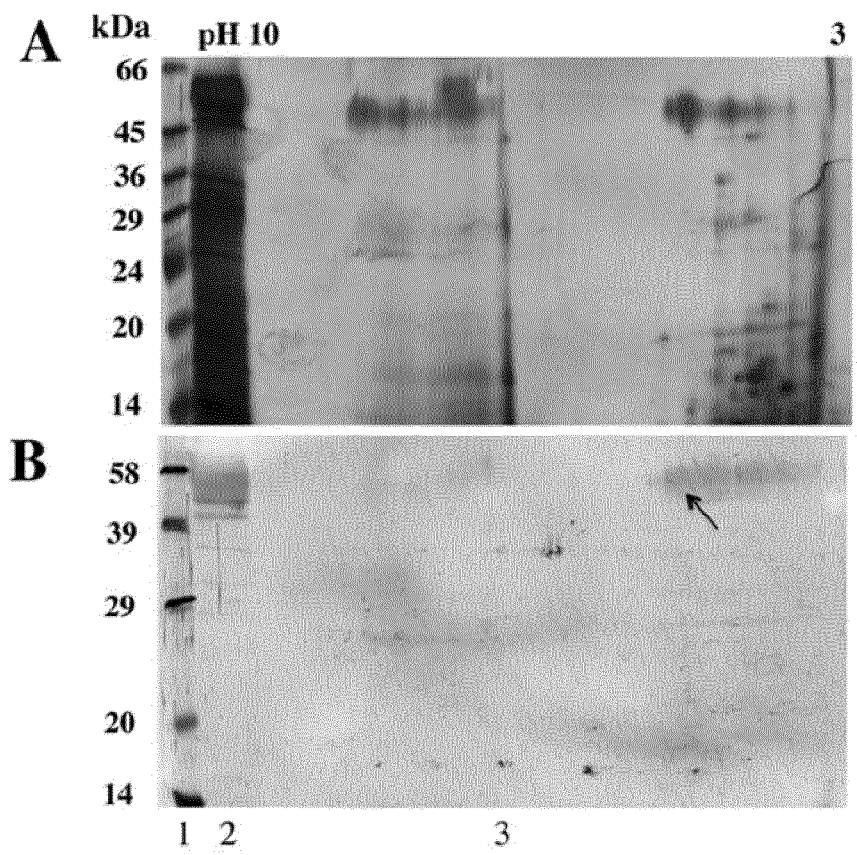
FIG. 3: Identification of Pfg. cPAHE (200 µg) were separated by 2D-electrophoresis. (A) Proteins were detected by silver staining. (B) Fibrinogen binding activity was determined with biotinylated fibrinogen by using the western ligand blot assay as described in Material and Methods. Lane 1, molecular weight standard; lane 2, sample separated only by 10% SDS-PAGE (1 DE) (50 µg of protein); lane 3, sample after 2DE as described in Materials and Methods. The arrow indicates the spot excised for identification by MALDI-ToF. (C) MALDI-ToF spectra obtained for spot of interest. Monoisotopic peptides masses were used to search protein databases to match and subsequently identify protein spot.
Figure 3:
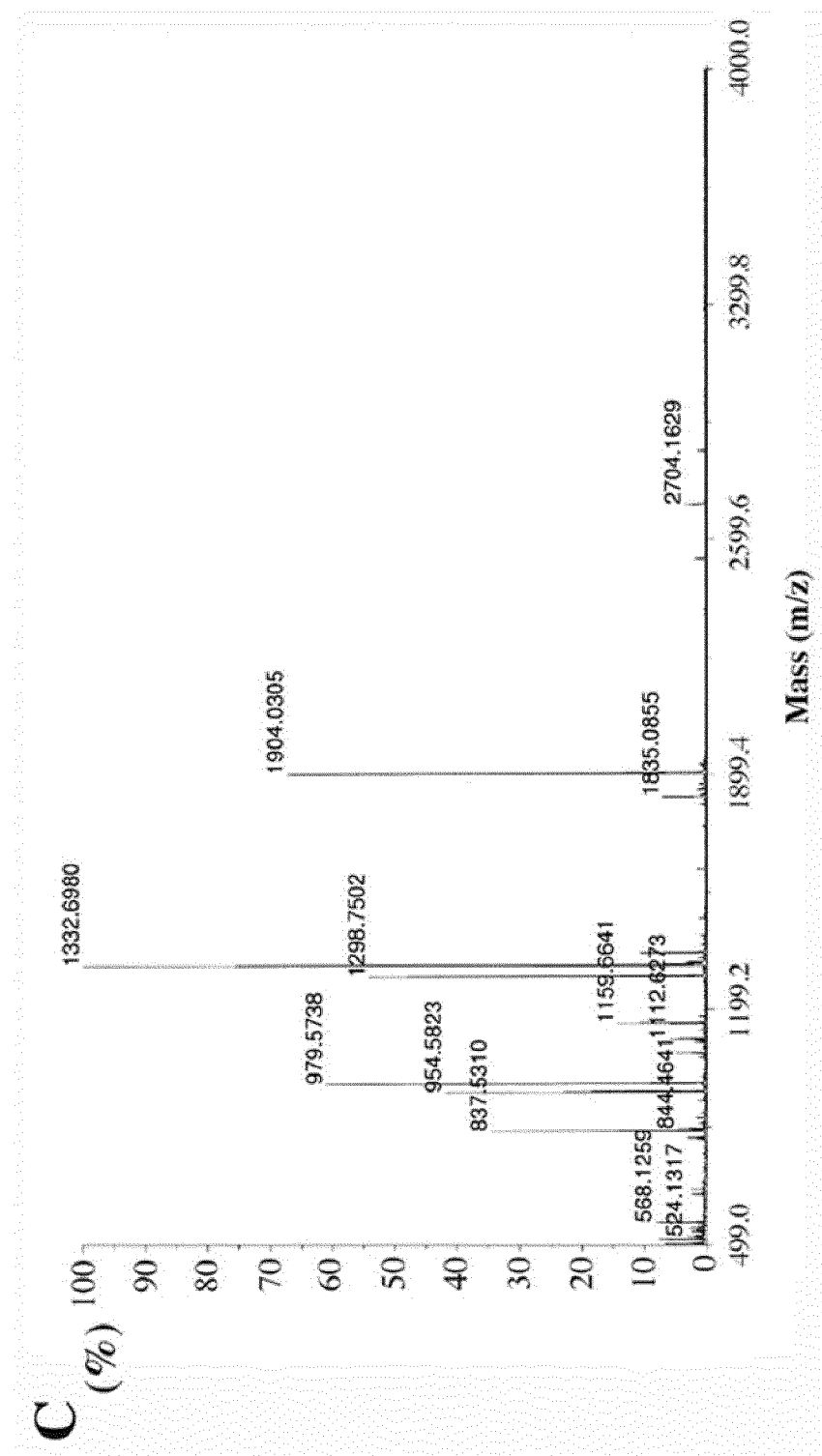

*P. acnes* surface extract was separated by 2-D gel electrophoresis. The first dimension was an IEF covering a broad pI range from 10 to 3. The second dimension was run on 12.5% SDS-PAGE, after which the proteins were detected by silver staining (FIG. 3A). Approximately 50 protein spots were observed after separation (FIG. 3A). To localize the spots corresponding to Pfg, a second gel was run in parallel and subjected to the Western ligand blot assay using biotinylated fibrinogen (FIG. 3B). Pfg appeared under 2-3 major spots (FIG. 3B, lane 3) and were matched with the spots in the silver stained gel (FIG. 3A, lane 3). The presence of several spots, all recognized by fibrinogen, suggest that Pfg would be glycosylated and therefore separated under several isoelectric points during the first dimension. The protein spot of interest was excised and characterized by MALDI-ToF of peptide mixtures after in-gel digestion. FIG. 3C shows a MALDI mass spectrum of a tryptic peptide mixture produced from the protein spot arrowed in FIG. 3A. Twenty two experimentally obtained tryptic peptide masses were found to match predicted peptide masses to within 0.1 Da, covering 57% of the amino acid sequence. Protein sequence database searching identified the protein as the product of gene of *P. acnes* hypothetical protein, putative adhesion or S-layer protein YP_056792 (Table 3) (GeneID 2933198, locus tag PPA2127) (Bruggemann 2004). The PPA2127 gene product is a 405-amino-acid hypothetical protein with a repetitive proline- and threonine-rich region at the C terminus (proline-threonine repetitive protein [PTRP]). Amino acid sequence analysis of PTRP showed the presence of 16 tandem repeats of motif Pro-Thr or Pro-Lys in the C-terminal region from positions 324 to 355. The theoretical molecular mass of the protein is of 41.7 kDa. Protein sequence analysis revealed the presence of a LPXTG motif at the position 400 at the C-terminus corresponding to a cell-anchoring motif possible site for a sortase and arguing in favor of a surface protein present on the *P. acnes* membrane.

TABLE 3

Measured and calculated molecular masses for tryptic peptides[a].

| Mass (Da)[b] | | | | |
|---|---|---|---|---|
| Measured | Calculated | Difference | Position | Sequence |
| 503.27 | 503.28 | −0.01 | 249-253 | AGIDK (SEQ ID NO: 25) |
| 813.50 | 813.51 | −0.01 | 65-73 | AAIAGALVK (SEQ ID NO: 26) |
| 818.42 | 818.42 | 0.00 | 300-306 | TAEQLEK (SEQ ID NO: 27) |
| 837.53 | 837.53 | 0.00 | 242-248 | IVTHLVR (SEQ ID NO: 28) |
| 928.55 | 928.54 | 0.01 | 124-133 | AAAAVDLGIK (SEQ ID NO: 29) |
| 954.58 | 954.57 | 0.01 | 254-262 | SLAVQIAPR (SEQ ID NO: 30) |
| 979.57 | 979.56 | 0.01 | 214-222 | AAIEHIIGR (SEQ ID NO: 31) |
| 1069.63 | 1069.62 | 0.01 | 270-279 | EPLLALNTAK (SEQ ID NO: 32) |

TABLE 3-continued

Measured and calculated molecular masses for tryptic peptides[a].

| Mass (Da)[b] | | | | |
|---|---|---|---|---|
| Measured | Calculated | Difference | Position | Sequence |
| 1084.60 | 1084.58 | 0.02 | 287-296 | QIVDVITADK (SEQ ID NO: 33) |
| 1101.62 | 1101.61 | 0.01 | 287-296 | QIVDVITADK (SEQ ID NO: 34) |
| 1107.67 | 1107.66 | 0.01 | 213-222 | KAAIEHIIGR (SEQ ID NO: 35) |
| 1112.62 | 1112.62 | 0.00 | 307-316 | ELPALDDLVK (SEQ ID NO: 36) |
| 1159.66 | 1159.65 | 0.01 | 95-104 | EGVLLINHHK (SEQ ID NO: 37) |
| 1282.75 | 1282.74 | 0.01 | 195-207 | AEIAAQAALLVGR (SEQ ID NO: 38) |
| 1332.69 | 1332.69 | 0.00 | 74-87 | AGFSSADAVALAPR (SEQ ID NO: 39) |
| 1341.73 | 1341.73 | 0.00 | 152-165 | DAVVANLVAAGVDK (SEQ ID NO: 40) |
| 1469.84 | 1469.83 | 0.01 | 152-166 | DAVVANLVAAGVDKK (SEQ ID NO: 41) |
| 1644.93 | 1644.90 | 0.03 | 74-90 | AGFSSADAVALAPRIAK (SEQ ID NO: 42) |
| 1810.00 | 1810.02 | -0.02 | 134-151 | ATLAATIIPNALHSAAFK (SEQ ID NO: 43) |
| 1834.08 | 1834.08 | 0.00 | 170-189 | ATAVAIAATALNPALGPIAK (SEQ ID NO: 44) |
| 1903.02 | 1903.02 | 0.00 | 223-241 | SFDAAVATAIVSSPILNAR (SEQ ID NO: 45) |
| 3284.49 | 3284.54 | -0.05 | 373-405 | SGGHSQGGSGTHYIHHGVAPVLTHSSDLPSTGF (SEQ ID NO: 46) |

[a]These peptides which identified the 58 kDa protein BAND, cover 231 of 405 residues, corresponding to 57% sequence coverage.
[b]Mono-isotopic, masses.

Pfg Purification

Figure 4:
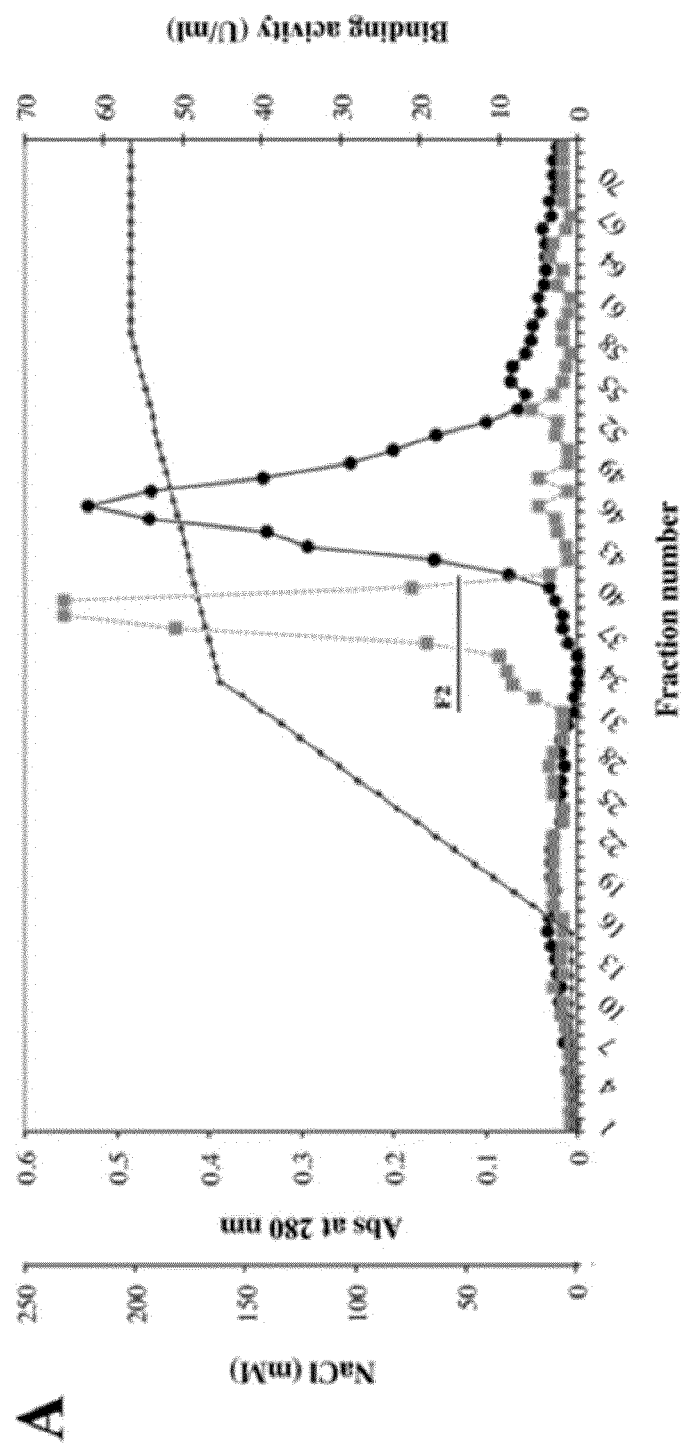
FIG. 4: Purification of Pfg. P. acnes surface protein were extracted by 1% LiCl at 42° C. for 2 h and then concentrated by ammonium sulfate precipitation at 80% of saturation. (A) cPAHE (85 mg) was loaded onto a UNOsphere Q column at 24 ml/h. Proteins equilibrated in 25 mM Tris, pH 8.0 were eluted with linear gradients of 0 to 160 mM for 60 min and 160 to 200 mM NaCl, 25 mM Tris, pH 8.0 for 90 min (●). Pooled fractions containing Pfg were dessalted and equilibrated in 0.1 M $NH_4HCO_3$, pH 8.0. (B) Proteins were fractionated by gel filtration chromatography onto a Sephacryl HR 5300 column at 6 ml/h. Void volume (Vo) was determined with thyroglobulin (669 kDa), and the elution positions for bovine-globulin (158 kDa), chicken ovalbumin (44 kDa), equine myoglobin (17 kDa) and vit. B12 (1.3 kDa) are indicated by arrows. Protein concentration was monitored at 280 nm (●). Fibrinogen binding activity (■) was determined with biotinylated fibrinogen as described in Materials and Methods. Horizontal lines labeled F2, F2.2 indicate the pooled fractions containing fibrinogen binding activity. (C) Proteins were separated by 10% SDS-PAGE and detected by Coomassie blue staining. (D) After electrophoretic separation, proteins were transferred to nitrocellulose membrane and fibrinogen binding activity was detected with biotinylated fibrinogen. Lanes 1a/b contain unstained and biotinylated molecular mass markers, respectively. Lane 2: P. acnes surface lithium total protein extract (10 µg). Lane 3: concentrated surface protein extract (10 µg). Lanes 4 and 5: 10 µg of pooled F2 and F2.2 fractions, respectively.
Figure 4:
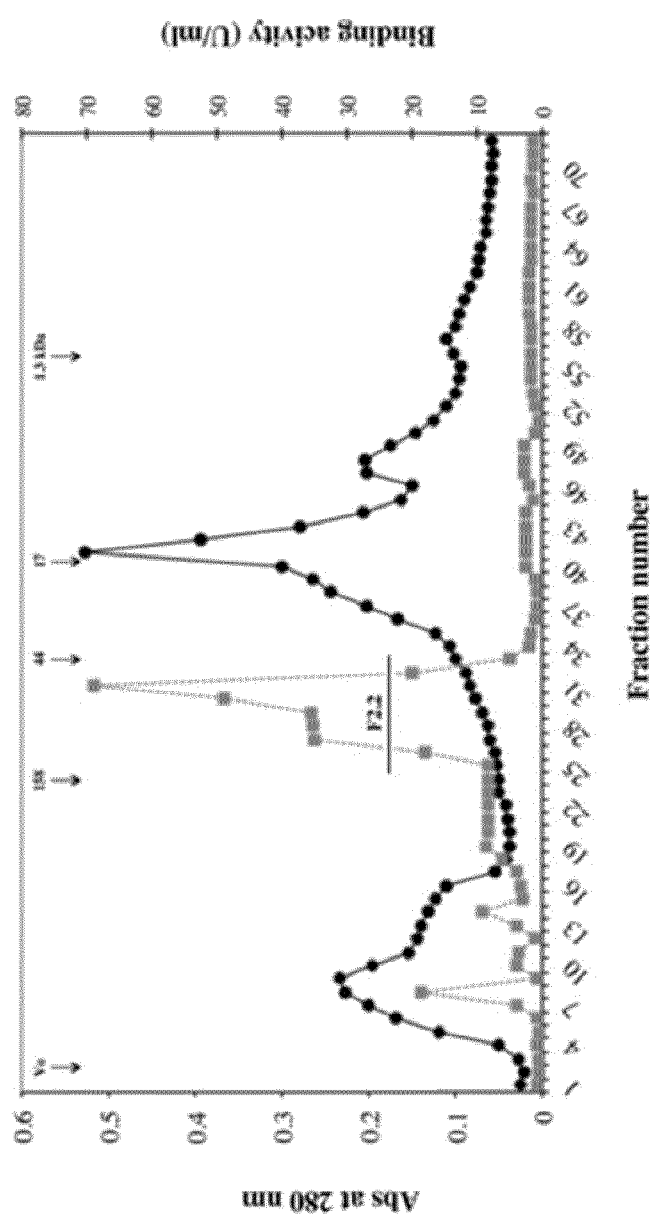
Figure 4:
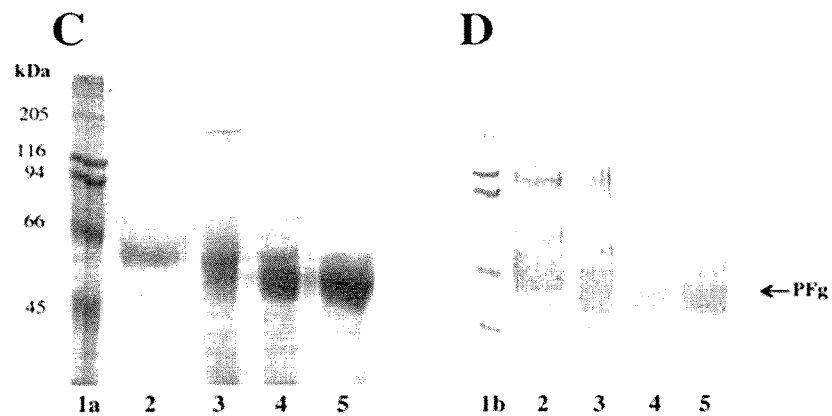

The results of a typical Pfg purification are summarized in Table 4. Salt precipitation of the large volume of *P. acnes* lithium extract resulted in the concentration of the protein and a small increase in the specific activity (1.45-fold of fibrinogen binding activity per unit of protein) of the resulting concentrated extract (Table 4 and FIG. 4C, D lane 3). The concentrated *P. acnes* surface protein was fractionated onto a anion exchange column (FIG. 4A). A large amount of protein contaminant was removed during this step, starting at the concentration of 180 mM NaCl. Fractions containing the fibrinogen binding activity were eluted at the NaCl concentration starting at 160 mM (FIG. 4A). This fraction contains a large proportion of Pfg along with few faints proteins contaminants (FIGS. 4C and D, lane 4). Final purification of Pfg was achieved by Sephacryl high resolution gel filtration during which all the protein contaminants were completely removed (FIGS. 4B and C, D, lane 5). The amount of pure Pfg obtained after this step was 0.23 mg, with a specific activity of 1840 U/mg (Table 4).

TABLE 4

Purification of Pfg.

| Purification step | Protein (mg) | Total units (U) | Specific Activity (U/mg) | PFg recovery (%) |
|---|---|---|---|---|
| PAHE | 1343 | 390000 | 290 | / |
| cPAHE | 378 | 160000 | 423 | 100 |
| Anion exchange | 2.9 | 3000 | 1034 | 1.87 |
| Gel filtration | 0.2 | 368 | 1840 | 0.23 |

Pfg Binding Specificity

Figure 5:
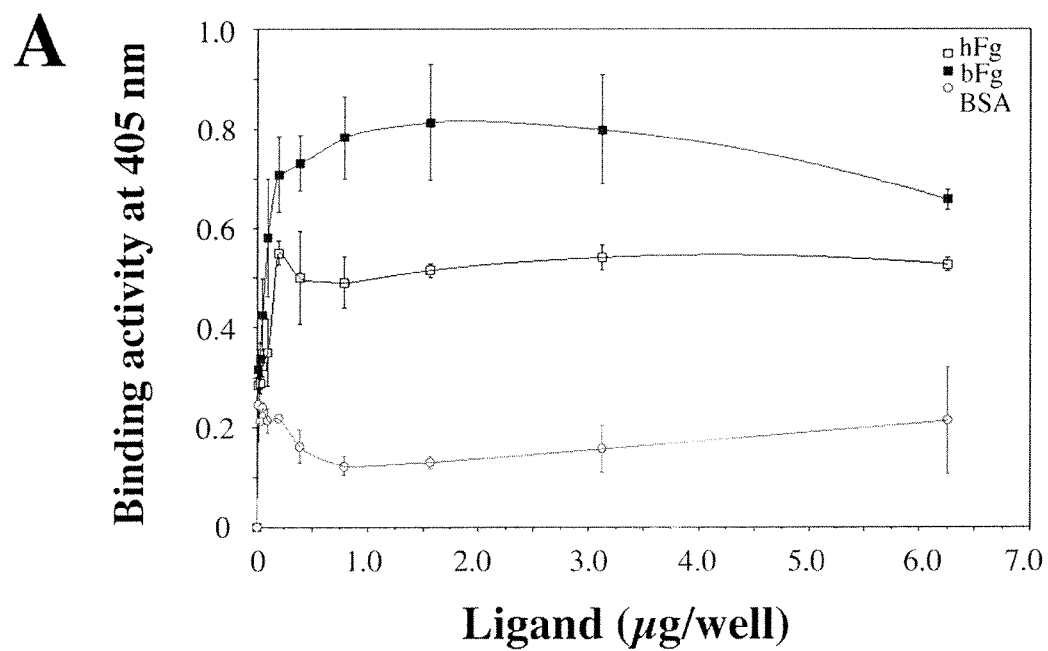
FIG. 5: Binding of P. acnes surface proteins to fibrinogen. (A) Various quantities of human fibrinogen (hFg) and bovine fibrinogen (bFg) were immobilized onto a 96-well polystyrene plate at 4° C. for 18 h and incubated with biotinylated Pfg at 0.1 µg/ml for 2 h at 23° C. Bovine serum albumin (BSA) was used as negative control. Bound material was detected by using the HRP-streptavidin conjugate. Peroxidase activity was measured by using the ABTS substrate at 405 nm. Proteins (10 μg per lane) were separated by 10% SDS-PAGE and detected by (B) Commassie blue staining, and transferred to nitrocellulose membrane and incubated with (C) HRP-streptavidine alone, and (D) biotinylated Pfg (0.1 μg/ml). Lanes 1: molecular weight standards. Lane 2: BSA. Lane 3: hFg. Lane 4: bFg.
Figure 5:
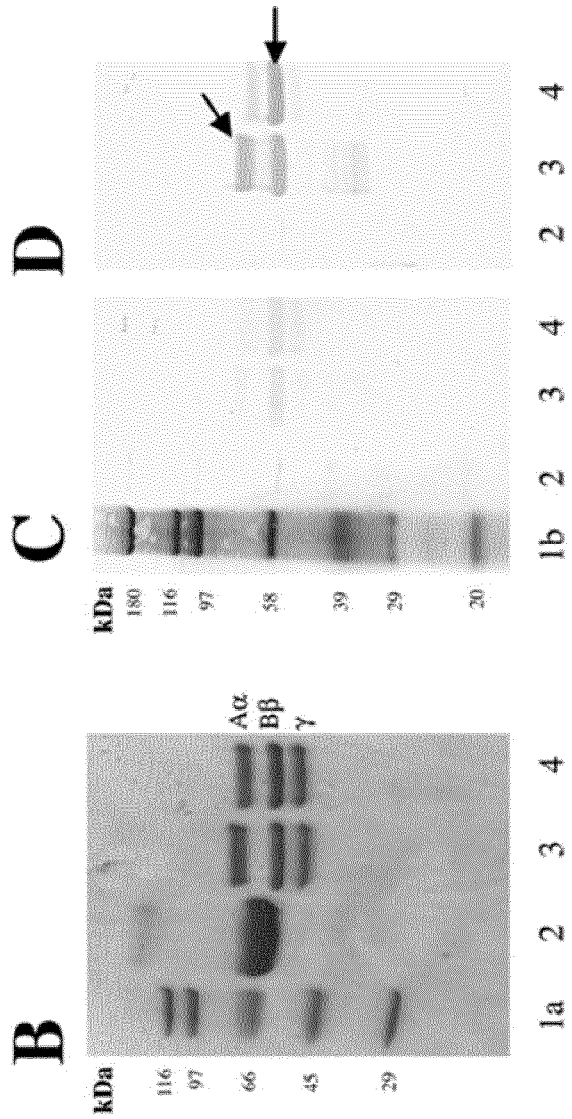
Figure 6:
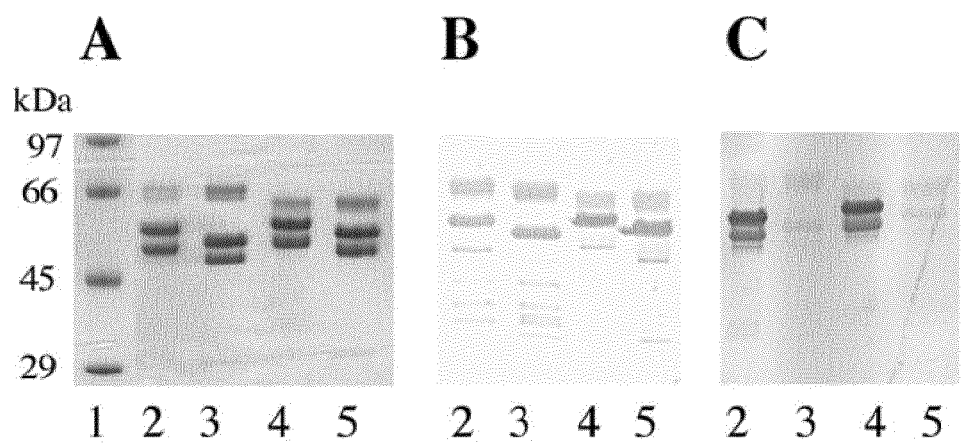
FIG. 6: Pfg recognition on N-deglycosylated fibrinogen. Purified human fibrinogen (hFg) and bovine fibrinogen (bFg) were subjected to treatment with N-glycosidase F (PNGAse F) as described in Materials and Methods. Untreated (lanes 2 and 4) and treated (lanes 3 and 5) samples (10 μg of protein per lane) were separated onto 10% SDS-PAGE and then transferred onto nitrocellulose membrane. (A) Proteins were detected by Coomassie blue staining. (B) Binding activity with biotinylated Pfg (0.1 μg/ml). (C) Biotinylated RCA-I lectin binding activity was used as deglycosylation control. Lanes 1: molecular weight standards.
Figure 7:
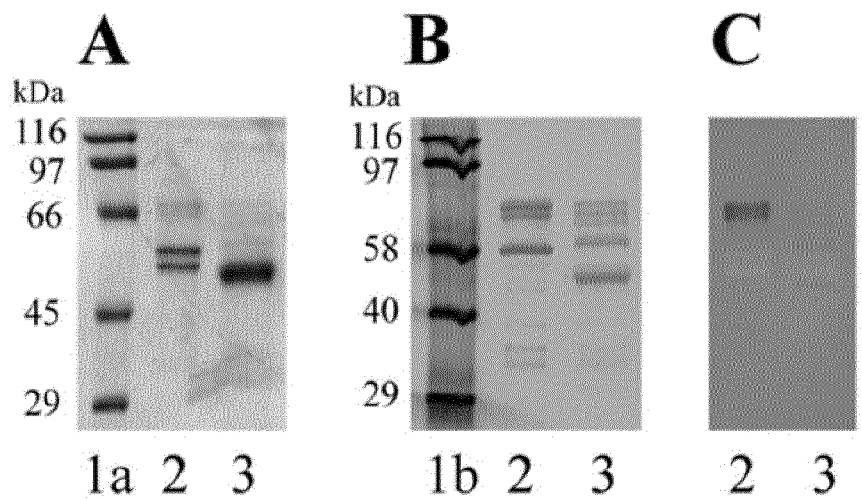
FIG. 7: Pfg recognition on O-deglycosylated fibrinogen. Purified human fibrinogen was subjected to treatment with O-glycosidase as described in Materials and Methods. Untreated (lane 2) and treated (lane 3) samples (10 μg of protein per lane) were separated onto 10% SDS-PAGE and then transferred onto nitrocellulose membrane. (A) Proteins were detected by Coomassie blue staining. (B) Binding activity with biotinylated Pfg (0.1 μg/ml). (C) Biotinylated Jacalin lectin binding activity was used as deglycosylation control. Lanes 1a and 1b corresponds to the molecular weight standards.

Since it was shown that Pfg is recognized by fibrinogen, this ECM ligand was used to analyze the nature of this interaction. First it was analyzed the ability of fibrinogen to be recognized by purified Pfg (FIG. 5). Human and bovine Fg (hFg, bFg) were immobilized to polysterene plate and the binding activity of biotinylated Pfg was measured. It was shown that the binding of Pfg to hFg and bFg is dose-dependent with a higher affinity for hFg. Bovine serum albumin used as negative control showing no binding activity (FIG. 5A). In order to determine which subunit of Fg is recognized by Pfg, Fg was electrophoretically separated and the binding assay was performed (FIG. 5B, C, D). It has been shown that hFg (FIG. 5D, lane 3) and bFg (FIG. 5D, lane 4) are recognized by Pfg. Moreover, it appears that the Bß subunit is strongly recognized in both hFg and bFg, while only the Aα subunit is recognized in the hFg. No recognition was observed for the γ subunit as well as for serum albumin used as control (FIG. 5D, lane 2). These results are in accordance with the results obtained with immobilized fibrinogen and demonstrated the specific recognition of Pfg to Fg. It has been shown that fibrinogen is a glycoprotein containing both N- and O-linked glycans (Debeire 1985; Reid Townsend 1982; L'Hôte 1996). To demonstrate which part of the glycoprotein was involved in the recognition by P. acnes surface proteins, purified fibrinogen was treated with PNGase F and O-glycosidase to specifically remove the N- and O-linked glycans from the protein backbone, respectively, and was tested for its ability to be recognize by P. acnes surface protein extract (FIGS. 6 and 7). After removing the N-linked glycans, the fibrinogen was still strongly recognized by Pfg (FIG. 6B, lanes 3 and 5). In parallel, deglycosylation was assessed by visualization of a shift in the mobility after electrophoresis separation and Coomassie blue staining (FIG. 6A, lanes 3 and 5) and also by using the RCA-I plant lectin able to recognize ß-linked galactosyl residues in terminal position (FIG. 6C) (Green, 1987). We showed that the deglycosylated Fg was no longer recognized by the RCA-I lectin (FIG. 6C, lanes 3 and 5). Same results were obtained after removing the O-linked glycans (FIG. 7B, lane 3) where deglycosylation controls shown that the enzymatic treatment removed all carbohydrates as detected the mobility shift (FIG. 7A, lane 3) and by jacalin plant lectin which is recognizing specifically Galß (1-3) residues on O-linked glycans (Tachibana 2006) (FIG. 7C, lane 3). These results indicate that the protein backbone of fibrinogen was involved in the recognition process by P. acnes surface protein.

Delineation of Bß Human Fibrinogen Sequence Recognized by Pfg

Figure 8:
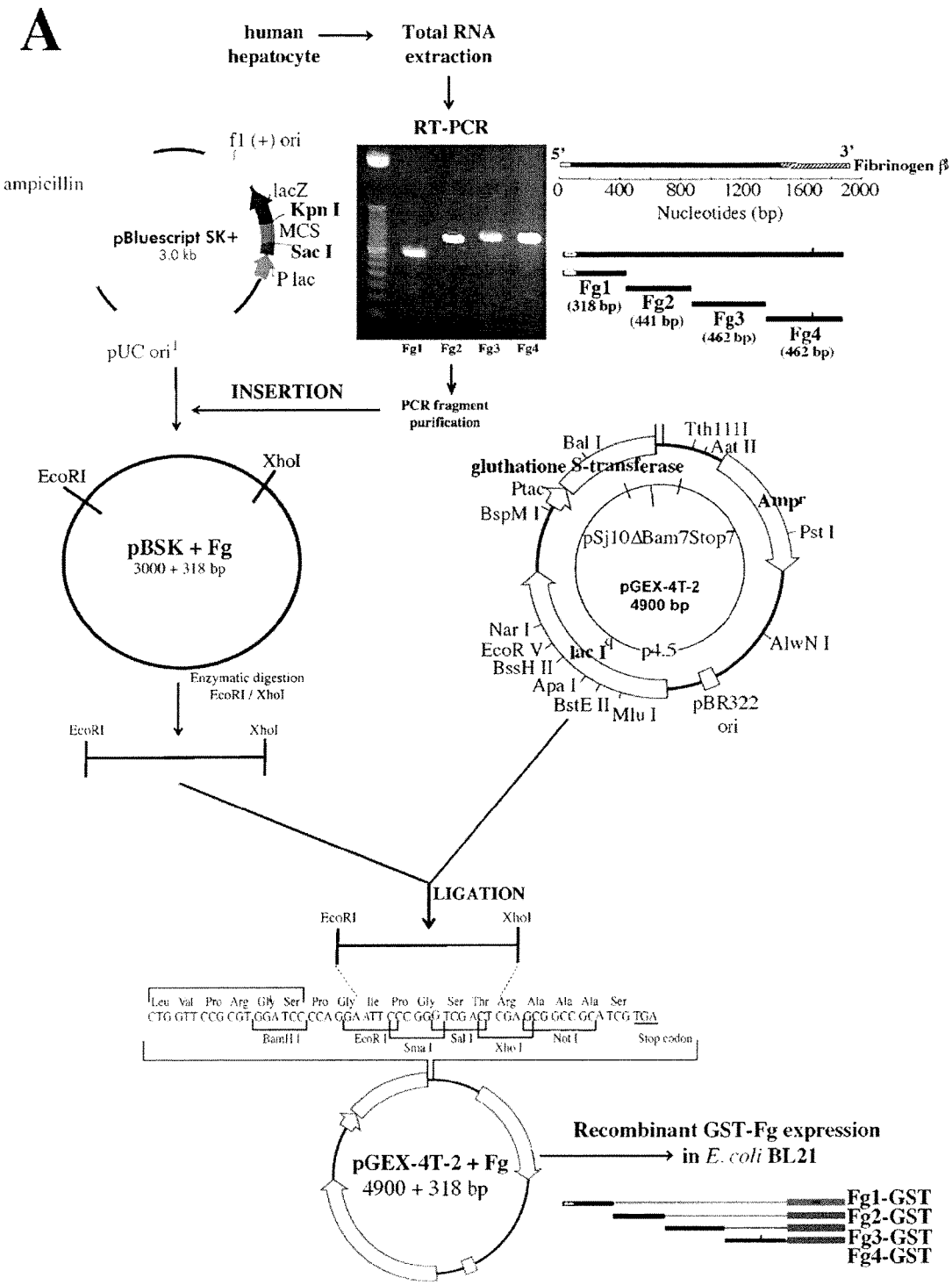
FIG. 8: Cloning of Bß human fibrinogen fragments and binding with Pfg. (A) Cloning and expression of recombinant human Bß fibrinogen fragments Fg1, Fg2, Fg3 and Fg4. Fibrinogen fragments were obtained by RT-PCR and expression plasmids were constructed as described in Materials and Methods. (B) GST-fused proteins were expressed in $E.$ $coli$, fractionated by 12.5% SDS-PAGE, and detected by Coomassie blue staining (B), and incubated with biotinylated Pfg (0.1 μg/ml) as described in Materials and Methods (C).
Figure 8:
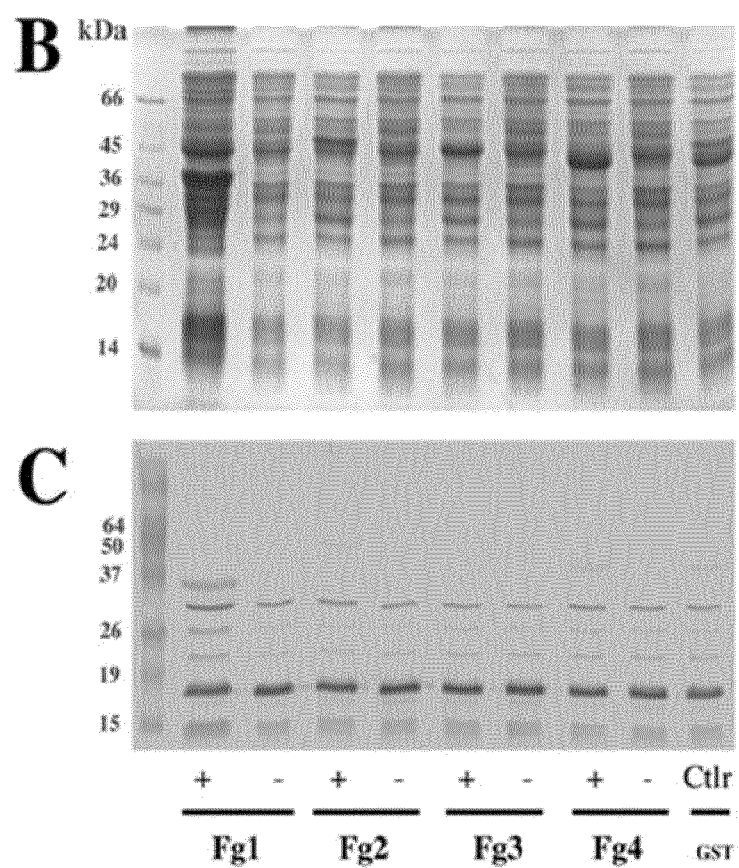

The Bß subunit of the human fibrinogen was arbitraly divided into 4 equal sequences (Fg1, Fg2, Fg3, Fg4) which were obtained by RT-PCR from human hepatocytes. The amplicons, containing the restriction sites for EcoRI and XhoI, were purified and subsequently cloned into the plasmid pBSK for production of the Fgs inserts which were cloned into the pGEX-4F-2 expression plasmid (FIG. 8A). Recombinants E. coli clones were subjected to IPTG induction and the total protein were analyzed by electrophoresis. Recombinant proteins of apparent molecular mass of 37- and 43 kDa for Fg1 and Fg2, Fg3, Fg4, respectively were overexpressed after induction (FIG. 8B). Contact with biotinylated Pfg have shown that only Fg1 was recognized (FIG. 8C).

Fibrinogen-Derived Peptide Inhibits the Interaction Between Pfg and Fibrinogen

Figure 9:
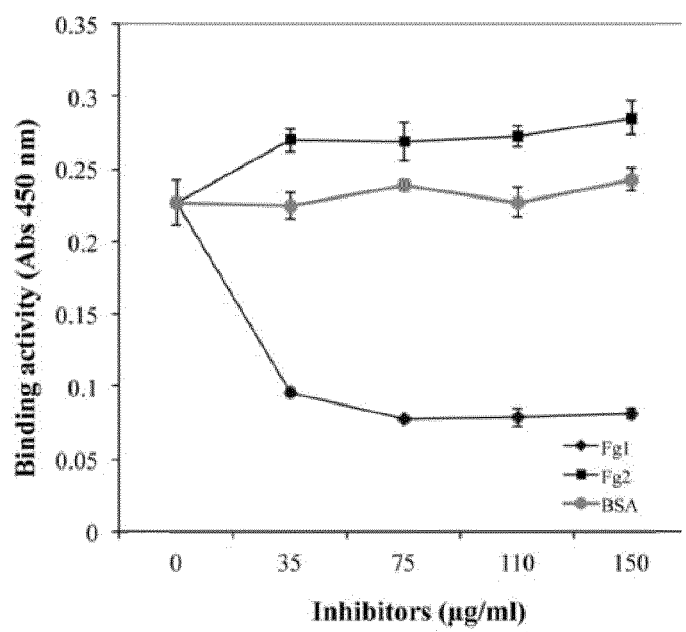
FIG. 9: Dose-dependent inhibition of biotinylated Pfg binding to fibrinogen by fibrinogen-derived peptide. Biotinylated PFg (0.4 mg) was pretreated with increasing amount of recombinant peptides Fg1 (♦), Fg2 (■) or BSA as control (●) for 1 h at 37° C., and the binding activity to coated fibrinogen on polystyrene plate (25 μg per well) was evaluated. Results are expressed as mean±SD. Each point was done in quadruplet.

Since it has been shown that only Fg1 was able to recognize Pfg, biotinylated Pfg was pre-treated with various concentrations of purified Fg1 and tested its ability to recognize immobilized fibrinogen. Fg2 and BSA were used as neative controls (FIG. 9). It has been shown that Fg1 dramatically decreased the recognition between Pfg and human fibrinogen while Fg2 and BSA did not.

These results show that the interaction between Pfg and the fibrinogen involves the protein backbone of the fibrinogen. Thus, the use of a recombinant peptide from the Bß subunit of the human fibrinogen allows inhibiting the interaction between Pfg and the fibrinogen.

Evaluation of Fg1 Anti-Adhesive Effect on Different Strains of P. acnes

Figure 10:
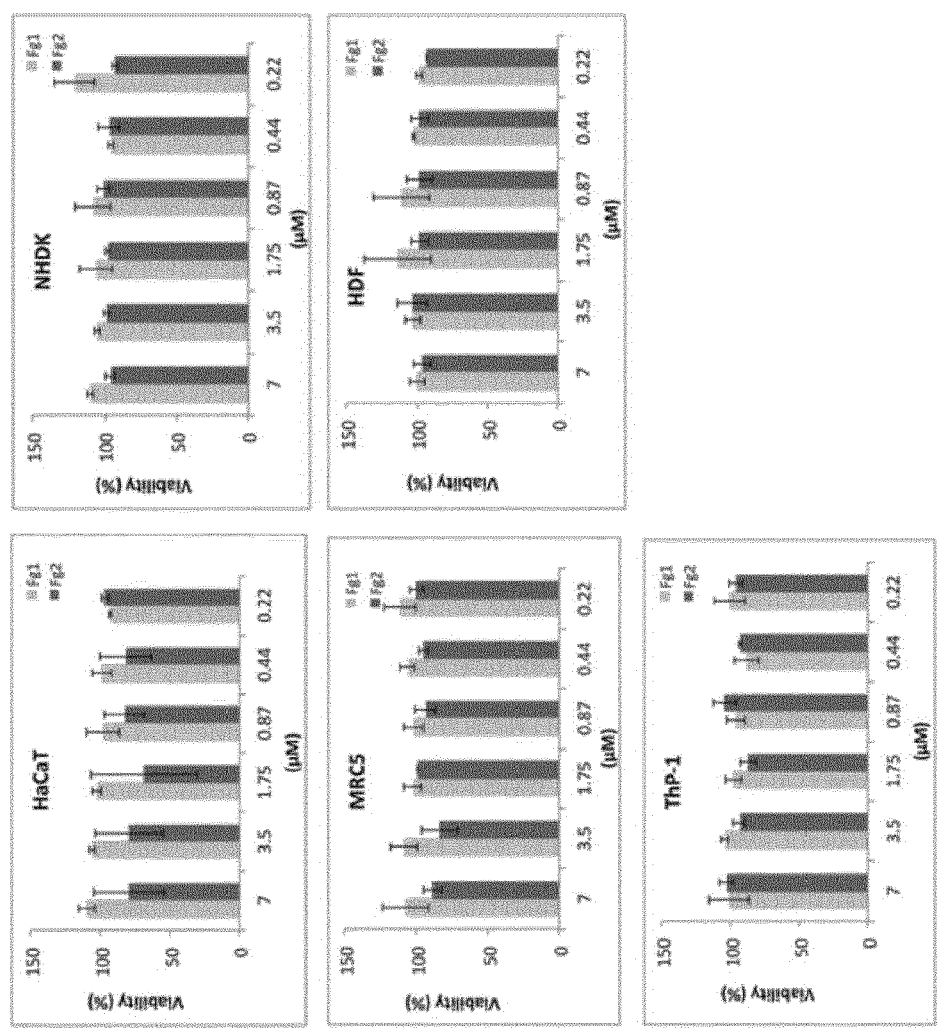
FIG. 10: Evaluation of cell viability after treatment with the Fg1 and Fg2 recombinant peptides. Human immortalized and primary keratinocyte cell lines HaCaT and NHDK; immortalized monocytes cell line ThP1, and immortalized and primary fibroblast cell lines MRC5 and HDF were incubated with Fg1 and Fg2 recombinant peptides with concentrations ranging from 0.22 to 7 mM for 18 h at 37° C. Cell viability was assessed using the MTT assay as described in Materials and Methods.

Whole P. acnes bacteria are labelled by biotinylation, pre-treated or not with the peptides and contacted with the various cell lines. After removal of the unfixed bacteria, the adhesion activity was measured spectrophotometrically by using the streptavidin-peroxidase conjugate and a chromogenic substrate. All lots of Fg1 Fg2 products and peptides, were tested in cytotoxicity in 5 cell lines used in this invention It has been shown that Fg1 and Fg2 exhibit no cytotoxic activity on all cell lines (FIG. 10).

Figure 11:
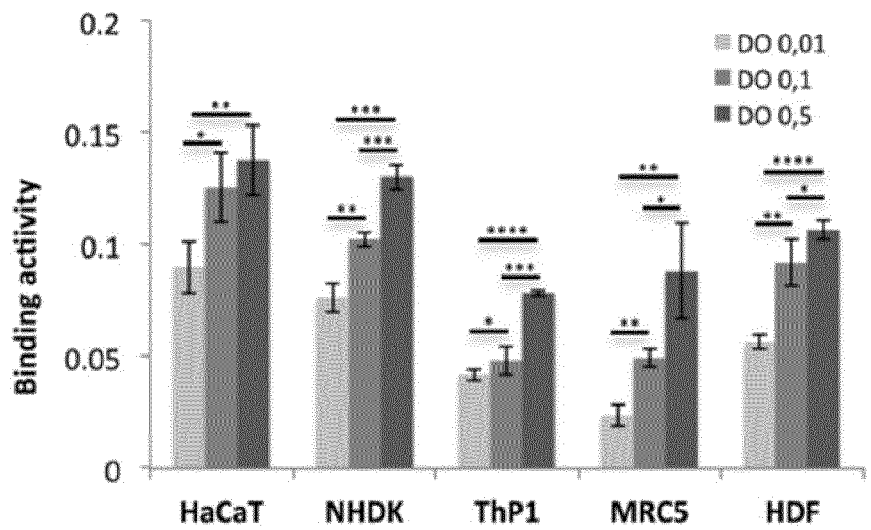
FIG. 11: Dose-dependency of binding activity of $P.$ $acnes$ RON strain on various cells lines. Biotinylated $P.$ $acnes$ RON strain at concentrations adjusted to 0.01, 0.1 and 0.5 of absorbance at 600 nm was incubated 1 h at 37° C. with the human immortalized and primary keratinocyte cell lines HaCaT and NHDK; with the immortalized monocytes cell line ThP1, and with the immortalized and primary fibroblast cell lines MRC5 and HDF. After removal of unbound bacteria, adhesion activity was detected at 410 nm. Data are means±S.D. of three separate experiments. Statistical significance is indicated by * (P<0.05),  (P<0.01), * (P<0.001), and **** (P<0.0001), respectively.
Figure 12:
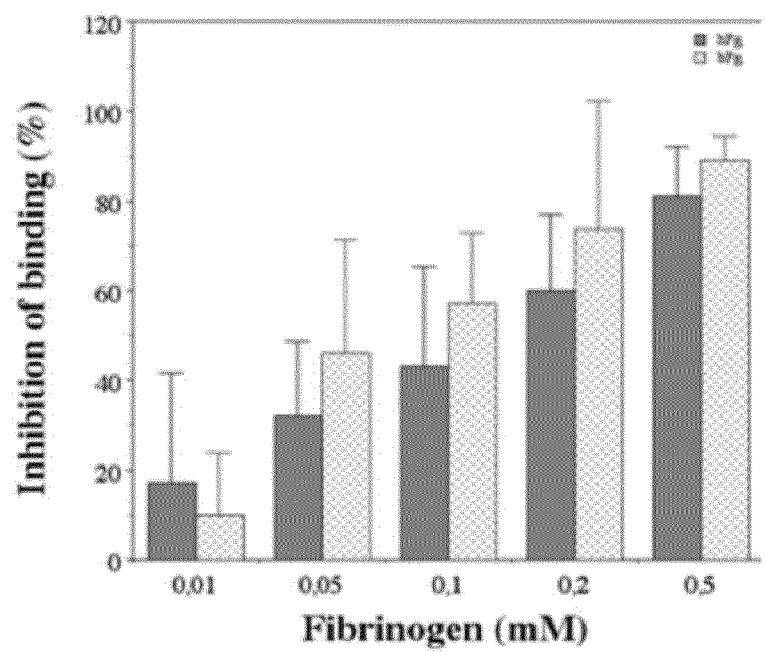
FIG. 12: Dose-dependent inhibition of $P.$ $acnes$ binding to keratinocytes. Biotinylated $P.$ $acnes$ 6919 strain at concentrations adjusted to 0.1 of absorbance at 600 nm was pre-treated with whole human (dark gray bar) and bovine (light gray bar) fibrinogen at the concentrations ranging from 0.01 to 0.5 mM and incubated 1 h at 37° C. with the human HaCaT keratinocyte cell line. After removal of unbound bacteria, adhesion activity was detected at 410 nm. Data are means±S.D. of three separate experiments. Statistical significance is indicated by * (P<0.05),  (P<0.01), * (P<0.001), and **** (P<0.0001), respectively.
Figure 13:
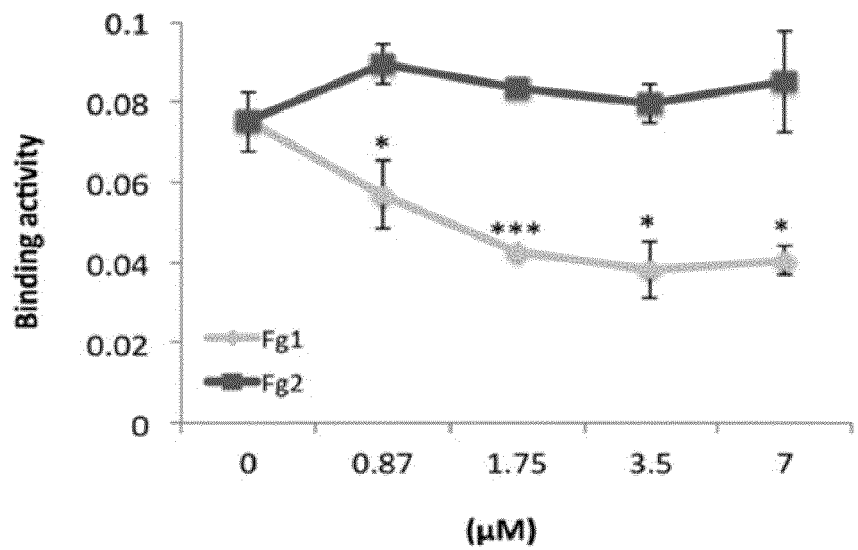
FIG. 13: Dose-dependent inhibition of $P.$ $acnes$ RON binding to monocytes cell line. Biotinylated $P.$ $acnes$ RON strain at concentrations adjusted to 0.1 of absorbance at 600 nm was pre-treated with the recombinant peptides Fg1 and Fg2 and incubated 1 h at 37° C. with the human immortalized monocytes cell line ThP1. After removal of unbound bacteria, adhesion activity was detected at 410 nm. Data are means±S.D. of three separate experiments. Statistical significance is indicated by * (P<0.05),  (P<0.01), * (P<0.001), and **** (P<0.0001), respectively.

The ability of P. acnes strains 6919, RON and PIE was tested at 3 concentrations to adhere to various cells lines. It has been shown that the strains of P. acnes tested bound to the three kind of cell lines tested (keratinocytes, monocytes and fibroblast) with a maximum adhesion strength found for keratinocytes (FIG. 11). Knowing that P. acnes is able to recognize fibrinogen, it was used human and bovine whole fibrinogen to compete the interaction between the bacteria and the target cell. It has been shown that increasing amount of both, human and bovine fibrinogen, are able to inhibit the adhesion of P. acnes to keratinocytes (FIG. 12). Then, the ability Fg1 to inhibit the adhesion of bacteria and RON PIE was evaluated on the 3 main types cell. It has been shown that the Fg1 peptide, inhibits the adhesion of RON strain in a dose-dependent manner on keratinocytes (NHDK), monocytes (THP-1), and fibroblasts (HDF). In parallel Fg2 peptide, used as a negative control shows no anti-adhesive activity (FIG. 13). Same results were obtained with the 6919 and PIE P. acnes strains.

Thus, it has been demonstrated that P. acnes strains are able to adhere to different target cells with a higher affinity for keratinocytes. Entire fibrinogen is able to compete the adhesion between the bacteria and the keratinocytes. When using the Fg1 recombinant peptide from the Bß subunit of fibrinogen, the adhesion of the whole bacteria to the target cells was significantly decreased.

Evaluation of the Anti-Inflammatory Activity of Fg1 in Cells Stimulated with P. acnes To assess the efficacy of Fg1 recombinant peptide, the production of $O_2^{\circ-}$ and $H_2O_2$ by HaCaT cells NHDK, THP-1, MRC5 and HDF stimulated by pretreated P. acnes strains 6919, RON and PIE was measured. The amount of ROS produced was compared to that produced by the stimulated cells with untreated bacteria. Production baseline was obtained by measuring ROS on unstimulated cells. The production of IL-1ß, IL-8, IL-12 and TNF-α was also measured in all conditions cited above. The measurement of the production of ROS is performed by spectrofluorimetry in the presence of specific fluorochromes directly on the monolayer cell. Measurement of cytokine production was performed in parallel on the cell culture supernatant.

Two sets of experiments were implemented: 1) The cells were stimulated (18 h at 37° C.) by P. acnes strains previously pretreated with Fg1 and Fg2 peptides at the final concentrations ranging from 0.87 to 7 µM for 1 h at 37° C.; and 2) The cells were pretreated first with Fg1 and Fg2 peptides at the final concentrations ranging from 0.87 to 7 µM for 24 h at 37° C. and stimulated (18 h at 37° C.) by P. acnes strains.

Figure 14:
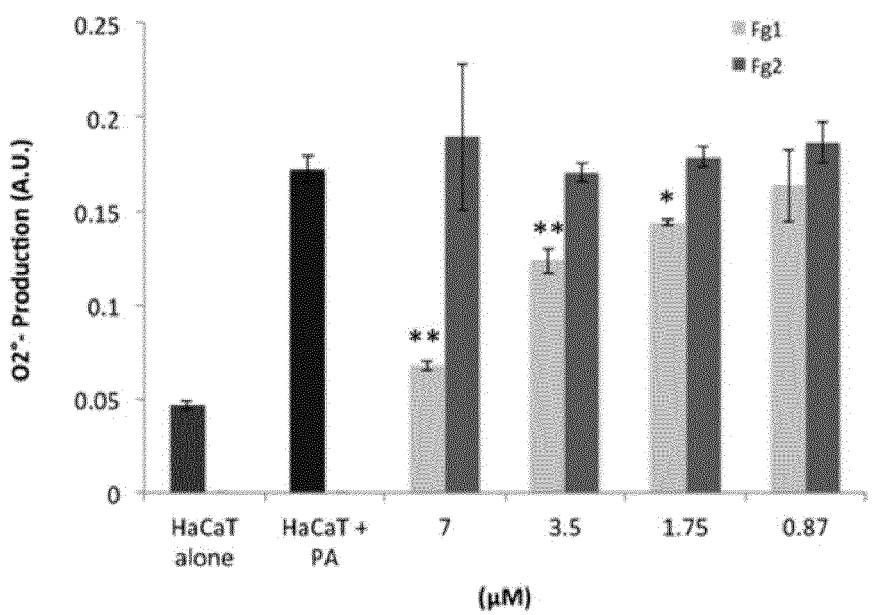
FIG. 14: Dose-dependent inhibition of $O_2^{\circ-}$ production by keratinocytes stimulated by $P.$ $acnes$ pre-treated by recombinant peptide. HaCaT cell were incubated for 18 h with $P.$ $acnes$ PIE strain at a concentration adjusted to 0.2 of absorbance at 600 nm (blue bar) and with $P.$ $acnes$ pretreated with recombinant peptide Fg1 (light gray bar) and Fg2 (dark gray bar). Measurement of superoxide anion production was realized by spectrofluorometry as described in Materials and Methods. Control experiment was done on unstimulated HaCaT cell (red bar). Data are means±S.D. of three separate experiments. Statistical significance is indicated by * (P<0.05),  (P<0.01), * (P<0.001), and **** (P<0.0001), respectively.

It has been shown that the production of $O_2^{\circ-}$ is important in all cell lines tested when stimulated by all three strains of P. acnes, these results represent controls experiments. In contrast, pretreatment of P. acnes strains by Fg1 peptide inhibits the production of $O_2^{\circ-}$ in a dose-dependent manner on the five cell lines and the three strains tested. Same kind of results was obtained for the production of $H_2O_2$ in both sets of experiments (Table 5). FIG. 14 corresponds to the results obtained with the *P. acnes* PIE strain on the keratinocyte HaCaT cell line and is representative of the results obtained with all *P. acnes* and tested cells lines.

Figure 15:
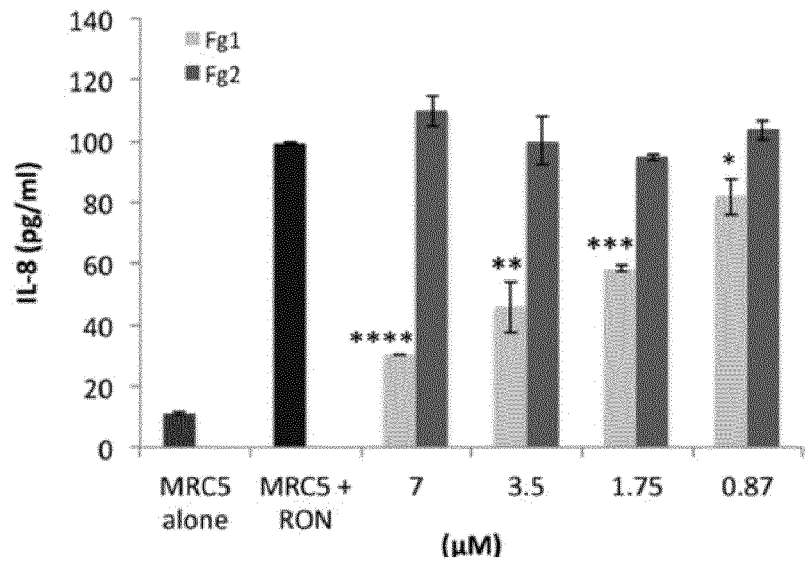
FIG. 15: Dose-dependent inhibition of IL-8 production by fibroblast stimulated by $P.$ $acnes$ pre-treated by recombinant peptide. MRC5 cells were incubated for 18 h with $P.$ $acnes$ RON strain at a concentration adjusted to 0.2 of absorbance at 600 nm (blue bar) and with $P.$ $acnes$ pretreated with recombinant peptide Fg1 (light gray bar) and Fg2 (dark gray bar). IL-8 concentration was measured by ELISA as described in Materials and Methods. Control experiment was done on unstimulated HaCaT cell (red bar). Data are means±S.D. of three separate experiments. Statistical significance is indicated by * (P<0.05),  (P<0.01), * (P<0.001), and **** (P<0.0001), respectively.

It has been shown that the production of IL-1ß is effective only for monocytes. Fg1 has no effect on the production of IL-1ß, whatever the strain of *P. acnes* used (Table 5). TNF-α production is effective for the monocytes and fibroblasts, whereas it is more random in keratinocytes. A Fg1 dose-response effect on the decrease of the production of TNF-α by monocytes and fibroblasts for the 3 bacterial tested strains were shown. The production of IL-12 was very low or non-existent for all the bacterial strains and cell lines tested proving to be a poor marker of inflammation in this model (Table 5). The production of IL-8 is important for keratinocytes (HaCaT and primary) and fibroblasts (MRC5 and primary) when stimulated by three strains of *P. acnes* (6919, RON and PEI). No production of IL-8 are monocytes. A Fg1 dose-response effect on the decrease of the production of IL-8 in keratinocytes and fibroblasts to the 3 bacterial tested strains was shown. Representative results are shown in FIG. 15 and concern the production of IL-8 obtained on the MRC5 cell line with the *P. acnes* RON strain.

TABLE 5

Overall of results of the evaluation of the anti-inflammatory activity of Fg1

| Inflammatory molecule production | *P. acnes* strain | Set of experiment | Nature of the test | Cell line | | | | |
|---|---|---|---|---|---|---|---|---|
| | | | | Keratinocyte | | Fibroblast | | Monocyte |
| | | | | HaCaT | NHDK | MRC5 | HDF | ThP1 |
| Superoxide anion ($O_2^{\circ -}$) | 6919 | I | Control | pos | pos | pos | pos | pos |
| | | | Inhibition | pos | pos | pos | pos | pos |
| | | II | Control | nt | pos | nt | pos | pos |
| | | | Inhibition | nt | pos | nt | pos | pos |
| | RON | I | Control | pos | pos | pos | pos | pos |
| | | | Inhibition | pos | pos | pos | pos | pos |
| | | II | Control | nt | pos | nt | pos | pos |
| | | | Inhibition | nt | pos | nt | pos | pos |
| | PIE | I | Control | pos | pos | pos | pos | pos |
| | | | Inhibition | pos | pos | pos | pos | pos |
| | | II | Control | nt | pos | nt | pos | pos |
| | | | Inhibition | nt | pos | nt | pos | pos |
| Hydrogen peroxide ($H_2O_2$) | 6919 | I | Control | pos | pos | pos | pos | pos |
| | | | Inhibition | pos | pos | pos | pos | pos |
| | | II | Control | nt | pos | nt | pos | pos |
| | | | Inhibition | nt | pos | nt | pos | pos |
| | RON | I | Control | pos | pos | pos | pos | pos |
| | | | Inhibition | pos | pos | pos | pos | pos |
| | | II | Control | nt | pos | nt | pos | pos |
| | | | Inhibition | nt | pos | nt | pos | pos |
| | PIE | I | Control | pos | pos | pos | pos | pos |
| | | | Inhibition | pos | pos | pos | pos | pos |
| | | II | Control | nt | pos | nt | pos | pos |
| | | | Inhibition | nt | pos | nt | pos | pos |
| Interleukine 1 beta (IL-1β) | 6919 | I | Control | na | pos | na | na | pos |
| | | | Inhibition | na | pos | na | na | NO |
| | | II | Control | na | na | na | na | pos |
| | | | Inhibition | na | na | na | na | NO |
| | RON | I | Control | na | na | na | na | pos |
| | | | Inhibition | na | na | na | na | NO |
| | | II | Control | na | na | na | na | pos |
| | | | Inhibition | na | na | na | na | NO |
| | PIE | I | Control | na | na | na | na | pos |
| | | | Inhibition | na | na | na | na | NO |
| | | II | Control | na | na | na | na | pos |
| | | | Inhibition | na | na | na | na | NO |
| Interleukine 8 (IL-8) | 6919 | I | Control | pos | pos | pos | pos | na |
| | | | Inhibition | pos | pos | pos | pos | na |
| | | II | Control | pos | pos | pos | pos | na |
| | | | Inhibition | pos | pos | pos | pos | na |
| | RON | I | Control | pos | pos | pos | pos | low |
| | | | Inhibition | pos | pos | pos | pos | na |
| | | II | Control | pos | pos | pos | pos | na |
| | | | Inhibition | pos | pos | pos | pos | na |
| | PIE | I | Control | pos | pos | pos | pos | low |
| | | | Inhibition | pos | pos | pos | pos | na |
| | | II | Control | pos | pos | pos | pos | na |
| | | | Inhibition | pos | pos | pos | pos | na |
| Interleukine TNF alpha (TNF-α) | 6919 | I | Control | na | na | pos | pos | pos |
| | | | Inhibition | na | na | pos | pos | pos |
| | | II | Control | na | na | pos | pos | pos |
| | | | Inhibition | na | na | pos | pos | pos |
| | RON | I | Control | na | low | pos | pos | pos |
| | | | Inhibition | na | na | pos | pos | pos |
| | | II | Control | na | na | pos | pos | pos |
| | | | Inhibition | na | na | pos | pos | pos |

TABLE 5-continued

Overall of results of the evaluation of the anti-inflammatory activity of Fg1

| Inflammatory molecule production | P. acnes strain | Set of experiment | Nature of the test | Cell line | | | | |
|---|---|---|---|---|---|---|---|---|
| | | | | Keratinocyte | | Fibroblast | | Monocyte |
| | | | | HaCaT | NHDK | MRC5 | HDF | ThP1 |
| Interleukine 12 (IL-12) | | PIE | I | Control | na | na | pos | pos | pos |
| | | | | Inhibition | na | na | pos | pos | pos |
| | | | II | Control | na | na | pos | pos | pos |
| | | | | Inhibition | na | na | pos | pos | pos |
| | 6919 | I | Control | na | na | na | na | low |
| | | | | Inhibition | na | na | na | na | pos |
| | | II | Control | na | na | na | na | na |
| | | | Inhibition | na | na | na | na | na |
| | RON | I | Control | na | pos | na | na | na |
| | | | Inhibition | na | pos | na | na | na |
| | | II | Control | na | na | na | na | na |
| | | | Inhibition | na | na | na | na | na |
| | PIE | I | Control | na | low | low | na | na |
| | | | Inhibition | na | na | na | na | na |
| | | II | Control | na | na | na | na | na |
| | | | Inhibition | na | na | na | na | na | na: non applicable;
nt: not tested
Control pos: production of inflammatory molecules in unstimulated and P. acnes stimulated cell is negative and positive, respectively.
Control low: production of inflammatory molecules in unstimulated and P. acnes stimulated cell is negative and weak, respectively.
Inhibition pos: Fg1 decrease the production of inflammatory molecule in a dose-dependent manner
Inhibition NO: Fg1 has no effect on the production of inflammatory molecule
I: Set of experiment where the bacteria are first pretreated.
II: set of experiments where the cells are first pretreated Evaluation of the Anti-Inflammatory Activity of Small Peptides Generated from Fg1

Figure 16:
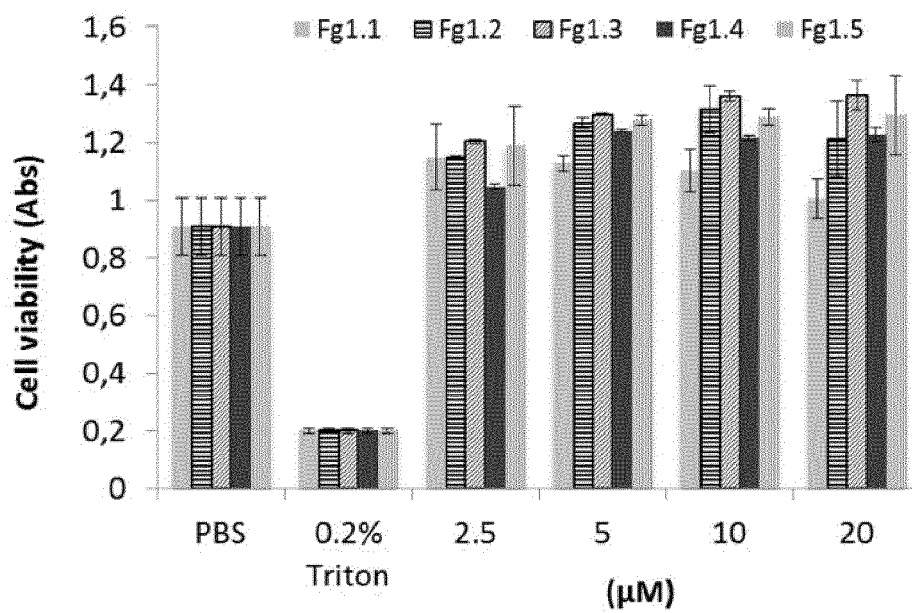
FIG. 16: Evaluation of cell viability after treatment with small Fg1-generated peptides on keratinocytes. HaCaT cell were incubated for 24 h with small peptides Fg1.1 (light gray bar), Fg1.2 (horizontal line bar), Fg1.3 (hatched bar), Fg1.4 (dark gray bar), Fg1.5 (dotted bar) at concentrations ranging from 2.5 to 20 μM. Measurement of cytotoxicity was determined by the MTT assay as described in Materials and Methods. Controls experiments were done with HaCaT cell incubated with PBS (corresponding to viable cells); and with 0.2% triton X100 (corresponding to dead cells). Data are means±S.D. of three separate experiments.

The Fg1 amino acid sequence containing 106 residues was divided into 3 non overlapping small sequences containing between 30 to 36 amino acid residues (small Fg1-related peptides; Fg1.1, Fg1.2, and Fg1.3). To avoid loss of putative activity in the cutting areas, two sequences overlapping with the 2 cutting areas were generated from this cutting site (Fg1.4 and Fg1.5) (FIG. 16).

Firstly, the cytotoxicity of all small Fg1-related peptides was assessed and it was shown shown that all small peptides tested were not toxic for cells in the range of 2.5 to 20 µM. FIG. 1 shown the results obtained on the immortalized keratinocyte HaCaT cell line. Same results were obtained on the immortalized-monocyte ThP1 and -fibroblast MRC5 cell lines.

To assess the efficacy of the small Fg1-related peptide, the production of $H_2O_2$ by several cell lines (HaCaT, NHDK, THP-1, MRC5 and HDF) stimulated by three P. acnes strains 6919, RON and PIE was measured, in presence or not with the small peptides. The amount of $H_2O_2$ produced is compared to that produced by the stimulated cells with untreated bacteria. Production baseline is obtained by measuring $H_2O_2$ on unstimulated cells. The measurement of the production of $H_2O_2$ is performed by spectrofluorimetry in the presence of specific fluorochromes directly on the monolayer cell.

Two sets of experiments have been implemented:
I) The cells are stimulated (18 h at 37° C.) by P. acnes strains previously pretreated with Fg1.1, Fg1.2, Fg1.3, Fg1.4, and Fg1.5 small peptides at the final concentrations ranging from 2.5 to 20 µM for 1 h at 37° C.;
II) The cells are pretreated first with the five small peptides at the final concentrations ranging from 2.5 to 20 µM for 24 h at 37° C. and stimulated (18 h at 37° C.) by P. acnes strains.

Figure 17:
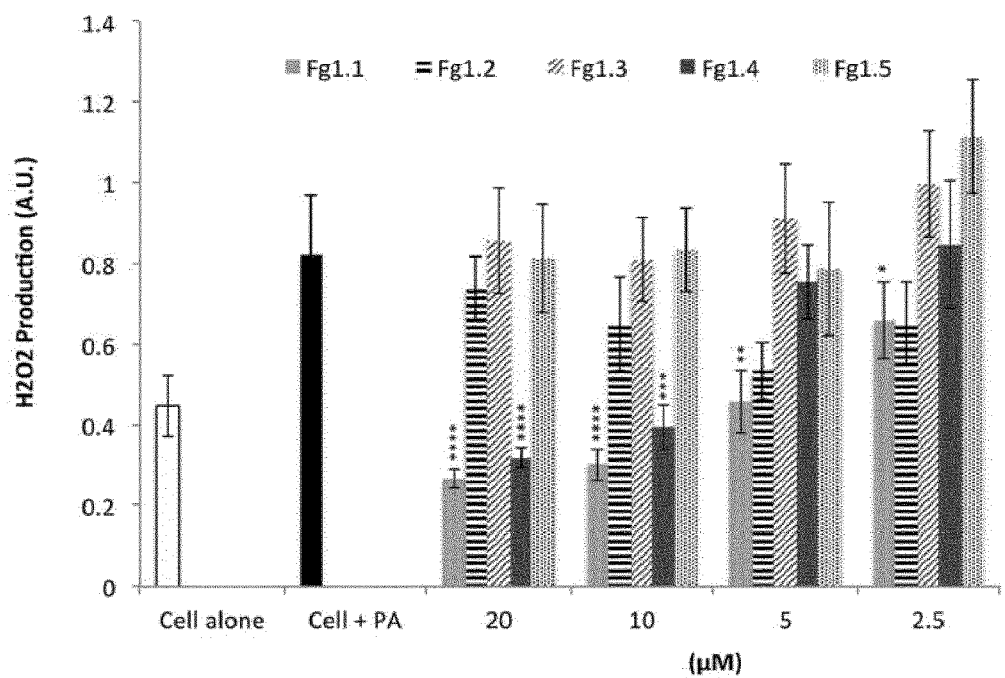
FIG. 17: Dose-dependent inhibition of $H_2O_2$ production by fibroblast pre-treated by small Fg1-generated peptides and stimulated by $P.$ $acnes$. MRC5 cell were incubated for 24 h with small peptides Fg1.1 (light gray bar), Fg1.2 (horizontal line bar), Fg1.3 (hatched bar), Fg1.4 (dark gray bar), Fg1.5 (dotted bar) at concentrations ranging from 2.5 to 20 µM. Measurement of hydrogen peroxide production was realized by spectrofluorometry as described in Materials and Methods. Controls experiments were done with unstimulated MRC5 cell (white bar) and MRC5 stimulated with *P. acnes* (black bar). Data are means±S.D. of three separate experiments. Statistical significance is indicated by * (P<0.05),  (P<0.01), * (P<0.001), and **** (P< 0.0001), respectively.

It has been shown that the production of $H_2O_2$ is adequate in all cell lines tested when stimulated by all three strains of P. acnes, these results represent control experiments. In contrast, pretreatment of P. acnes strains by the Fg1.1 and the Fg1.4 small peptide inhibits the production of $H_2O_2$ in a dose-dependent manner on the five cell lines and the three strains tested while the small peptides Fg1.2, Fg1.3 and Fg1.5 did not. FIG. 17 corresponds to the results obtained with the P. acnes RON strain on the fibroblast MRC5 cell line and are representative of the results obtained with all P. acnes and cells lines tested (Table 6).

TABLE 6

Overall of results of the evaluation of the anti-inflammatory activity of small Fg1-generated peptides.

| Inflammatory molecule production | P. acnes strain | Set of experiment | Nature of the test | Cell line | | | | |
|---|---|---|---|---|---|---|---|---|
| | | | | Keratinocyte | | Fibroblast | | Monocyte |
| | | | | HaCaT | NHDK | MRC5 | HDF | ThP1 |
| Hydrogen peroxide ($H_2O_2$) | 6919 | I | Control | pos | nt | pos | nt | pos |
| | | | Inhibition | pos | nt | pos | nt | pos |

TABLE 6-continued

Overall of results of the evaluation of the anti-inflammatory activity of small Fg1-generated peptides.

| Inflammatory molecule production | P. acnes strain | Set of experiment | Nature of the test | Cell line | | | | |
|---|---|---|---|---|---|---|---|---|
| | | | | Keratinocyte | | Fibroblast | | Monocyte |
| | | | | HaCaT | NHDK | MRC5 | HDF | ThP1 |
| | | II | Control | pos | pos | pos | pos | pos |
| | | | Inhibition | pos | pos | pos | pos | pos |
| | RON | I | Control | pos | nt | pos | nt | pos |
| | | | Inhibition | pos | nt | pos | nt | pos |
| | | II | Control | nt | pos | nt | pos | pos |
| | | | Inhibition | nt | pos | nt | pos | pos |
| | PIE | I | Control | pos | nt | pos | nt | pos |
| | | | Inhibition | pos | nt | pos | nt | pos |
| | | II | Control | pos | pos | pos | pos | pos |
| | | | Inhibition | pos | pos | pos | pos | pos | nt: not tested
Control pos: production of $H_2O_2$ in unstimulated and P. acnes stimulated cell is negative and positive, respectively.
Inhibition pos: Fg1.1 and Fg1.4 decrease the production of H2O2 in a dose-dependent manner
I: Set of experiment where the bacteria are first pretreated.
II: set of experiments where the cells are first pretreated Anti-Inflammatory Properties of Fg1 Fragment in the Absence of P. acnes To assess more generally the anti-inflammatory properties of Fg1 and Fg2 fragments, the production of $H_2O_2$ by several cell lines (NHDK, THP-1, and HDF) stimulated by LTA (lipoteichoic acid, LPS (lipopolysaccharide) and PGN (peptidoglycanne) was measured, in presence or not of Fg1 or Fg2.

Results obtained for NHDK cells stimulated by LTA are presented in FIG. 18, and show that Fg1 but not Fg2 significantly decreases production of $H_2O_2$ by LTA-stimulated NHDK cells. Similar results were obtained on primary fibroblast (HDF) and monocytes (ThP1) cells stimulated with LTA, LPS and PGN.

The production of IL-8 was also measured NHDK cells stimulated by LTA, LPS and PGN, in presence or not of Fg1 or Fg2. Results obtained for NHDK cells stimulated by PGN are presented in FIG. 19, and show that Fg1 but not Fg2 significantly decreases production of IL-8 by PGN-stimulated NHDK cells. Similar results were obtained on NHDK cells stimulated by LTA and LPS.

These results illustrate that Fg1 also has anti-inflammatory properties on keratinocytes, independently of the presence of P. acnes.

Evaluation of the Anti-Inflammatory Activity of Small Peptides Generated from Fg1.1

The anti-inflammatory activity of small fragments Fg1.1.1, Fg1.1.2, Fg1.1.3, Fg1.1.4 and Fg1.1.6 was assessed.

The inventors first assessed the cytotoxicity of all small Fg1.1-generated peptides and shown that all peptides tested were not toxic for cells in the range of 2.5 to 20 µM. FIG. 20 shows results obtained on immortalized keratinocyte HaCaT cell line. Similar results were obtained on immortalized fibroblast MRC5 cell line.

FIG. 21 shows the same experiment made using the diluent used to dissolve the peptides (vehicle) at the same concentrations. Stock solutions were made in: PBS for Fg1.1.4, 60% DMSO/PBS for Fg1.1.1 and Fg1.1.3, 100% DMSO for Fg1.1.2.

These results clearly show that the small fragments of the inventions having sequences up to 20 amino acids, preferably up to 15 amino acids have no toxic effect on keratinocytes.

The inventors then assessed the capacity of small fragments Fg1.1.1, Fg1.1.2, Fg1.1.3, Fg1.1.4 and Fg1.1.6 to reduce the inflammatory response of cells after P. acnes stimulation. The production of IL-8 by cell lines (HaCaT and MRC5) stimulated by P. acnes 6919 strain was measured. The amount of IL-8 was compared to that produced by the stimulated cells with untreated bacteria. Production baseline was obtained by measuring IL-8 on unstimulated cells. The measurement of IL-8 production was performed by an ELISA assay. Two sets of experiments which consist of I) the P. acnes strain is first pre-treated by the peptides at final concentrations ranging from 2.5 to 20 µM (see FIG. 22) and; II) the cells are first pre-treated by the peptides as described above and then stimulated by P. acnes (see FIG. 23) were performed. In this case, the lower is the IL-8 secretion level, the higher is the anti-inflammatory capacity of the tested fragment.

Results show that the production of IL-8 is adequate in all cell lines when stimulated by P. acnes. However, when the P. acnes strain is pre-treated with the Fg1.1.1 peptide, the production of IL-8 decreases in a dose-dependent manner. While some inhibition of IL-8 production is observed with other small fragments, the effect is less pronounced that with Fg1.1.1. FIG. 22 corresponds to the results obtained with pre-treated bacteria on HaCaT cells. Similar results have been obtained on fibroblast MRC5 cells, as well as when cell lines were first pre-treated (FIG. 23).

In Vivo Evaluation of the Anti-Inflammatory Activity of Small Peptide Fg1.1.1

According to previous results showing in vitro efficacy of the Fg1.1.1 peptide on the anti-inflammatory response, the inventors tested its capacity to inhibit the inflammatory reaction induced by P. acnes in an in vivo model of inflammation.

This model is based on the capacity of mouse ears to react while P. acnes is intradermally injected. The inflammatory reaction was evaluated each day over a period of 4 days after P. acnes injection by measuring the thickness of the ears, the redness as well as the presence of a desquamation and/or small pustules. At the end of the experiment, final measurement of inflammation was realized and photographic pictures of ears were taken. Then, mice were euthanized and ears as well as ears-related ganglions were removed. Ears were immediately fixed in a formalin-containing buffer for a future histological analysis. The ears-related ganglion were placed in appropriate cell culture media on ice and processed immediately to extract lymphocytes. All lymphocyte suspensions were counted and adjusted to obtain $2.10^5$ cell per well in a 96-well plate beforehand coated with anti-CD3 (2 µg/ml) and anti-CD28 (2.5 µg/ml) antibodies. After 72 h of growth, the proliferation rate was measured based on a redox indicator related to cellular metabolism (UptiBlue).

The experimental design consisted of 5 groups containing 8 mice each. 1) PBS corresponds to the non-treated group injected with PBS. 2) PA+Vehicle TOPIC corresponds to *P. acnes* injected in ears treated with vaseline alone. 3) PA+Peptide TOPIC corresponds to *P. acnes* injected in ears treated with 5% Fg1.1.1 peptide mixed in vaseline. 4) *P. acnes* strain ($OD_{620nm}$=1.5) was pre-treated for 1 h at 37° C. with Fg1.1.1 peptide (140 µM) (PA+Peptide INJECT group) or 5) with the vehicle alone (1% DMSO final in PBS) (PA+Vehicle INJECT group) and then intradermally injected in ears of mice (approximately $2.0^7$ CFU/20 µl) to induce inflammation.

The preparation of the 5% Fg1.1.1 peptide gel consisted of extemporaneously gently mixing 15 mg of peptide with 300 mg of vaseline for 1 min at room temperature (21° C.) and then directly applied to the mouse ears.

Results show that the Fg1.1.1 peptide is able to decrease the ear inflammation in topical application (FIG. 24, FIG. 26 #6) as well as on pre-treated bacteria (FIG. 25, FIG. 26 #5) compared to the not treated ears. Histological analysis revealed a lowest number of infiltrated immune cells when the Fg1.1.1 was applied (FIG. 27 #5 and 6), as well as a reduced level of lymphocyte activation (FIG. 28).

The abilities of big fragment Fg1 (106 amino acids) and small fragment Fg1.1.1 (15 amino acid) to inhibit IL-8 secretion were compared and represented on FIG. 29 which shows the normalized percentage of inhibition of IL-8 production from Immortalized keratinocytes (HaCaT), fibroblast (MRCS), monocytes (ThP1) cell lines and primary keratinocytes (NHDK), fibroblast (HDF) cell lines were grown at 37° C. under 5% $CO_2$ in DMEM with 10% SVF, RPMI with 10% SVF, KGM-Gold, FGM medium, respectively; and seeded at $5·10^4$ to $10^5$ cells/well in the presence of variable concentrations of peptides Fg1 or Fg1.1.1.

In this case, the higher is the inhibition, the higher is the anti-inflammatory capacity of the tested fragment. FIG. 29 shows also that the percentage of inhibition of IL-8 production is higher when the cells are treated with small fragment Fg1.1.1 having 15 amino acids than with big fragment Fg1 having 211 amino acids.

Anti-Inflammatory Properties of Fg1.1.1 in a Model of Psoriasis

Psoriasis is a chronic inflammatory disease mediated by Th17 lymphocytes infiltration that initiate pathophysiological responses of epidermal keratinocytes. In this context, keratinocytes are targets for numerous cytokines contributing to the regulation of their biological properties by contributing to the inflammatory response. This keratinocyte response is characterized by a variation in their differentiation and migration capabilities as well as secretion of cytokines, chemokines and antimicrobial peptides, among them IL-8, hBD-2, S100A7, IL-12RA2 are good markers.

Immortalized keratinocytes HaCaT cell were seeded in 96-well plates at $10^5$ cells/well (Corning Costar, Brumath, France) and stimulated with *P. acnes* 6919 strain ($O.D._{620\ nm}$=0.3) pretreated 1 h at 37° C. with the Fg1 and Fg1.1.1 peptides at the concentrations of 2.5, 5 and 10 µM for 18 h at 37° C. under 5% $CO_2$. Then, culture supernatant was removed and the IL-8 concentration was measured by ELISA assay (eBioscience).

To assess Fg1.1.1 anti-inflammatory activity on psoriasis, we used an in vitro model of normal human epidermal keratinocytes (NHEK) stimulated by a pro-inflammatory mixture reproducing a type phenotype "psoriasis" (combination of IL-17+OSM+TNF-α). We therefore evaluated Fg1.1.1 ability to inhibit the release of Il-8 and of ß-defensin-2 protein (hBD-2) by the keratinocytes stimulated in this condition.

Fg1.1.1 Activity on Il-8 Production (FIG. 30):

FIG. 30 shows that in basal conditions, normal human epidermal keratinocytes (NHEK) released a small amount of Il-8 (Cell alone). This release was greatly increased by the treatment with the combination of 3 cytokines (Stimulated cells). The reference Jak Inhibitor I (positive control) strongly inhibited the stimulating effect of this association (67% inhibition).

Under the experimental conditions of this study, Fg1.1.1, tested at 6.1 and 12.2 µM significantly inhibited the release of Il-8 by NHEK with a concentration-dependent effect (25% and 49% inhibition). At lower concentrations (1.25 and 3.05 µM), a smaller effect was observed.

Fg1.1.1 Activity on hBD-2 Production (FIG. 31):

FIG. 31 shows that in basal conditions, normal human epidermal keratinocytes released a very small amount of ß-defensin-2 protein (hBD-2) (Cell alone). This release was greatly increased by the treatment with the combination of Il-17, TNF-α and OSM (Stimulated cells). The reference Jak Inhibitor I (positive control) strongly inhibited the stimulating effect of this association (80% inhibition).

Under the experimental conditions of this study, Fg1.1.1 tested at 12.2 µM significantly inhibited the release of hBD-2 by NHEK. Moreover, Fg1.1.1 had no effect on cell viability at all concentrations tested.

When using an in vitro model of psoriasis, we have shown that the Fg1.1.1 peptide was able to inhibit the IL-8 and the hBD-2 molecules production in a dose dependent manner without any cytotoxicity. Moreover, the inhibition of IL-8 chemokine production was stronger than the hBD-2 antimicrobial peptide production in the range of concentrations tested, suggesting that higher dosage would abolish both anti-inflammatory molecules production. Thus, Fg1.1.1 peptide is a good candidate to decrease psoriasis-like inflammation.

REFERENCES

Brüggemann, H., A. Henne, F. Hoster, H. Liesegang, A. Wiezer, A. Strittmatter, S. Hujer, P. Dlirre, G. Gottschalk. 2004. The complete genome sequence of *Propionibacterium acnes*, a commensal of human skin. Science. 305: 671-673.

Debeire, P., J. Montreuil, E. Moczar, H. Van Halbeek, J. F. G. Vliegenthart. 1985. Primary structure of two major glycans of bovine fibrinogen. Eur. J. Biochem. 151:607-611.

Dawson, A., Dellavalle R., 2013, Acne vulgaris, BMJ; 346:f2634.

Graham G. M., M. D. Farrar, J. E. Cruse-Sawyer, K. T. Holland, E. Ingham. 2004. Proinflammatory cytokine production by human keratinocytes stimulated with *Propionibacterium acnes* and *P. acnes* GroEL. Br. J. Dermatol. 150:421-428.

Grange, P. A., C. Chereau, J. Raingeaud, C. Nicco, B. Weill, N. Dupin, F. Batteux. 2009a. Production of superoxide anions by keratinocytes initiates *P. acnes*-induced inflammation of the skin. PLoS Pathog. 5(7): e1000527. doi: 10.1371/journal.ppat.1000527.

Grange, P. A., J. Raingeaud, V. Calvez, N. Dupin. 2009b. Nicotinamide inhibits *Propionibacterium acnes*-induced IL-8 production in keratinocytes through the NF-kappaB and MAPK pathways. J Dermatol. Sci. 56:106-112.

Green, E. D., R. M. Brodbeck, J. U. Baenziger. 1987. Lectin affinity high-performance liquid chromatography. Interactions of N-glycanase-released oligosaccharides with *Ricinus communis* agglutinin I and *Ricinus communis* agglutinin II. J. Biol. Chem. 262:12030-12039.

Grice, E. A., H. H. Kong, S. Conlan, C. B. Deming, J. Davis, A. C. Young, G. G. Bouffard, R. W. Blakesley, P. R. Murray, E. D. Green, M. L. Turner, J. A. Segre. 2009. Topographical and temporal diversity of the human skin microbiome. Science 324:1190-1192.

Gristina, A. G., P. Naylor, Q. Myrvik. 1988. Infections from biomaterials and implants: a race for the surface. Med. Prog. Technol. 14:205-224.

Kang, S., S. Cho, J. H. Chung, C. Hammerberg, G. J. Fisher, J. J. Voorhees. 2005. Inflammation and extracellular matrix degradation mediated by activated transcription factors nuclear factor-B and activator protein-1 in inflammatory acne lesions in vivo. Am. J. Pathol. 166:1691-1699.

Kistowska, M., S. Gehrke, D. Jankovic, K. Kerl, A. Fettelschoss, L. Feldmeyer, G. Fenini, A. Kolios, A. Navarini, R. Ganceviciene, J. Schauber, E. Contassot, L. E. French. 2014 IL-1☐ drives inflammatory responses to *Propionibacterium acnes* in vitro and in vivo. J. Invest. Dermatol. 134:677-685.

L'Hôte, C., S. Berger, Y. Karamanos. 1996. O-glycosylation of fibrinogen from different mammalian species as revealed by the binding of *Escherichia coli* biotinylated lectins. Thromb. Haemost. 76:710-714.

Nagy, I., A. Pivarcsi, A. Koreck, M. Széll, E. Urbán, and L. Kemény. 2005. Distinct strains of *Propionibacterium acnes* induce selective human-defensin-2 and interleukin-8 expression in human keratinocytes through Toll-like receptors. J. Invest. Dermatol. 124:931-938.

Patti, J. M., M. Höök. 1994. Microbial adhesins recognizing extracellular matrix macromolecules. Curr. Opin. Cell. Biol. 6:752-758.

Peterson, G. L. 1983. Determination of total protein. Methods Enzymol. 91:95-119.

Qin, M., A. Pirouz, Kim M.-H, S. R. Krutzik, H. J. Garban, J. Kim. 2014 *Propionibacterium acnes* induces IL-1 secretion via the NLRP3 inflammasome in human monocytes. J. Invest. Dermatol. 134:381-388.

Romero-Steiner, S., T. Witek, E. Balish. 1990. Adherence of skin bacteria to human epithelial cells. J. Clin. Microbiol. 28:27-31.

Shen, W., A. Ljungh. 1993. Collagen binding to *Escherichia coli* strain NG7C. Curr. Microbiol. 27:311-316.

Tachibana, K., S. Nakamura, H. Wang, H. Iwasaki, K. Tachibana, K. Maebara, L. Cheng, J. Hirabayashi, and H. Narimastu. 2006. Elucidation of binding specificity of jacalin toward O-glycosylated peptides: quantitative analysis by frontal affinity chromatography. Glycobiology 16:46-53.

Trivedi, N. R., K. L. Gilliland, W. Zhao, W. Liu, D. M. Thiboutot. 2006. Gene array expression profiling in acne lesions reveals marked upregulation of genes involved in inflammation and matrix remodeling. J. Invest. Dermatol. 126:1071-1079.

Townsend, R. R., R., E. Hilliker, Y.-T. Li, R. A. Laine, W. R. Bell, Y. C. Lee. 1982. Carbohydrate structure of human fibrinogen. Use of 300-MHz $^1$H-NMR to characterize glycosidase-treated glycopeptides. J. Biol. Chem 257: 9704-9710.

Yu, J.-L., R. Mansson, J.-I. Flock, A. Ljungh. 1997 Fibronectin binding by *Propionibacterium acnes*. FEMS Immun. Med. Microbiol. 19:247-253.

Vorm, O., M. Mann. 1994. Improved mass accuracy in matrix-assisted laser desorption/ionization time-of-flight mass spectrometry of peptides. J. Am. Soc. Mass. Spectrom. 5:955-958.

The invention claimed is:

1. A method for treating and/or preventing a skin inflammatory disease comprising administering to a subject in need thereof an isolated polypeptide comprising an amino acid sequence with at least 80% identity with SEQ ID NO:1 after optimal global alignment or a fragment thereof comprising an amino acid sequence with at least 80% identity with any one of SEQ ID NOs:2, 5, 7, 8, 9, 10, 11, 12, 13, and 47 after optimal global alignment.

2. The method according to claim 1, wherein said polypeptide is selected from SEQ ID NOs:2, 5, 7, 8, 9, 10, 11, 12, 13, and 47 or a polypeptide with at least 80% identity with one of SEQ ID NOs: 2, 5, 7, 8, 9, 10, 11, 12, 13, and 47 after optimal global alignment.

3. The method according to claim 1, wherein the skin inflammatory diseases is acne.

4. The method according to claim 1, wherein said isolated polypeptide or fragment thereof inhibits the interaction with fibrinogen of at least one microbial protein involved in bacterial adhesion to a host cell.

5. The method according to claim 1, wherein the skin inflammatory disease is psoriasis.

6. The method according to claim 1, wherein said isolated polypeptide or fragment thereof inhibits the interaction with fibrinogen of at least one microbial protein involved in bacterial adhesion to a host cell, wherein the bacteria is *P. acnes*, and wherein the fibrinogen is human fibrinogen.

* * * * *